(12) United States Patent
Holland et al.

(10) Patent No.: US 8,710,223 B2
(45) Date of Patent: Apr. 29, 2014

(54) PROTEIN KINASE C INHIBITORS AND USES THEREOF

(75) Inventors: Sacha Holland, San Francisco, CA (US); Rao Kolluri, Foster City, CA (US); Salvador Alvarez, Fremont, CA (US); Matthew Duncton, San Bruno, CA (US); Rajinder Singh, Belmont, CA (US); Jing Zhang, Foster City, CA (US); Esteban Masuda, Menlo Park, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 186 days.

(21) Appl. No.: 13/188,222

(22) Filed: Jul. 21, 2011

(65) Prior Publication Data

US 2012/0022092 A1   Jan. 26, 2012

Related U.S. Application Data

(60) Provisional application No. 61/366,464, filed on Jul. 21, 2010.

(51) Int. Cl.
*C07D 401/14* (2006.01)

(52) U.S. Cl.
USPC ........................................................ 544/324

(58) Field of Classification Search
USPC .................. 544/323, 324; 514/275
See application file for complete search history.

(56) References Cited

U.S. PATENT DOCUMENTS

| | | | |
|---|---|---|---|
| 7,517,886 B2 | 4/2009 | Singh et al. | |
| 7,557,210 B2 | 7/2009 | Singh et al. | |
| 8,178,671 B2 | 5/2012 | Singh et al. | |
| 8,377,924 B2 * | 2/2013 | Singh et al. | 514/217.04 |

FOREIGN PATENT DOCUMENTS

| | | |
|---|---|---|
| WO | WO2006133426 A2 | 12/2006 |
| WO | WO2009012421 A1 | 1/2009 |
| WO | 2010083207 | 7/2010 |
| WO | 2010083240 | 7/2010 |
| WO | 2010090875 | 8/2010 |
| WO | 2011068898 | 6/2011 |

OTHER PUBLICATIONS

Layzer, Degenerative Diseases of the Nervous System, Cecil Textbook of Medicine, 20th Edition, vol. 2, pp. 2050-2057 (1996).*
Damasio, Alzheimer's Disease and Related Dementias, Cecil Textbook of Medicine, 20th Edition, vol. 2, pp. 1992-1996 (1996).*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Hayashi et al., Protein Kinase C theta (PKCe): A key role in T cell life and death, Pharmacological Research 55 (2007), pp. 537-544.*
Duncton et al. (2010) "Dibutyl 2-(trifluoromethyl)cyclopropylboronate as a useful (trifluoromethyl)cyclopropyl donor: application to antagonists of TRPV1" Tetrahedron Lett 51(7):1009-1011.
Newton, A.C., (1995), "Protein Kinase C: Structure, Function, and Regulation", J. Biol. Chem., 270(48): 28495-28498.
Mondiano, J.F., et al.,(1991), "Protein Kinase C Regulates Both Production and Secretion of Interlukin 2", J. Biol. Chem., 266(16): 10552-10561.
Abboushi, N., et al., (2004), "Ceramide Inhibits IL-2 Production by Preventing Protein Kinase C-Dependent NF-Kinase C • Regulation", J. Immunol., 173: 3193-3200.
Hoyer, K.K., et al., (2008), "Interleukin-2 in the development and control of inflammatory disease", Immunol. Rev., 266: 19-28.

* cited by examiner

*Primary Examiner* — Deepak Rao
(74) *Attorney, Agent, or Firm* — Rudy J. Ng; Carol L. Francis; Bozicevic, Field & Francis LLP

(57) ABSTRACT

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions comprising these compounds, methods of using these compounds in the treatment of various diseases and disorders, processes for preparing these compounds and intermediates useful in these processes.

2 Claims, No Drawings

SEQUENCE LISTING

```
<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 1

Arg Phe Ala Arg Lys Gly Ser Leu Arg Gln Lys Asn Val
 1               5                   10
```

PROTEIN KINASE C INHIBITORS AND USES THEREOF

CROSS-REFERENCE TO RELATED APPLICATIONS

This application claims the priority benefit under 35 U.S.C. §119(e) of pending U.S. application 61/366,464, filed Jul. 21, 2010, which is hereby incorporated herein by reference in its entirety.

BACKGROUND

Protein kinase C ("PKC") is a key enzyme in signal transduction involved in a variety of cellular functions, including cell growth, regulation of gene expression, and ion channel activity. The PKC family of isozymes includes at least 11 different protein kinases that can be divided into at least three subfamilies based on their homology and sensitivity to activators. Each isozyme includes a number of homologous ("conserved" or "C") domains interspersed with isozyme-unique ("variable" or "V") domains. Members of the "classical" or "cPKC" subfamily, PKC $\alpha$, $\beta_i$, $\beta_{ii}$ and $\gamma$, contain four homologous domains (C1, C2, C3 and C4) and require calcium, phosphatidylserine, and diacylglycerol or phorbol esters for activation. Members of the "novel" or "nPKC" subfamily, PKC $\delta$, $\epsilon$, $\eta$ and $\theta$, lack the C2 homologous domain and do not require calcium for activation. Finally, members of the "atypical" or "aPKC" subfamily, PKC $\zeta$ and $\lambda/i$, lack both the C2 and one-half of the C1 homologous domains and are insensitive to diacylglycerol, phorbol esters and calcium.

SUMMARY

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions comprising these compounds, methods of using these compounds in the treatment of various diseases and disorders, processes for preparing these compounds and intermediates useful in these processes.

Exemplary chemical structures are provided throughout the disclosure. By way of example, such compounds are represented by the following formula:

(I)

wherein $R^5$ is selected from haloalkyl, alkoxy, substituted alkoxy, cyano, halogen, acyl, aminoacyl, and nitro;

$Y^1$ and $Y^2$ are independently selected from hydrogen, alkyl, and acyl;

$R^1$ is selected from hydrogen, alkyl, and substituted alkyl;

$R^a$ and $R^b$ are independently selected from hydrogen and alkyl;

$R^c$ and $R^d$ are independently selected from hydrogen and alkyl;

$R^{6a}$ is selected from hydrogen, alkyl, substituted alkyl, cyano, halogen, acyl, aminoacyl, nitro, cycloalkyl, and substituted cycloalkyl;

$R^{6b}$ is selected from hydrogen, alkyl, substituted alkyl, cyano, halogen, acyl, aminoacyl, nitro, cycloalkyl, and substituted cycloalkyl;

$R^{7b}$ is selected from hydrogen, alkyl, substituted alkyl, cyano, halogen, acyl, aminoacyl, nitro, cycloalkyl, and substituted cycloalkyl;

$R^8$ is selected from hydrogen, $C_{2-10}$ alkyl, substituted alkyl, cyano, halogen, acyl, aminoacyl, nitro, cycloalkyl, and substituted cycloalkyl;

$R^{7x}$ is selected from hydrogen, alkyl, haloalkyl, cycloalkyl, and substituted cycloalkyl;

wherein at least one of $R^{6a}$, $R^{6b}$, $R^{7b}$, and $R^8$ is not hydrogen;

wherein if $R^8$ is fluoro, then $R^{7b}$ is not hydrogen; and wherein if $R^8$ is fluoro, then $R^{7b}$ is not hydrogen; and wherein if $R^{7b}$ is cyclopropyl, then at least one of $R^{6a}$, $R^{6b}$, $R^8$, and $R^{7x}$ is not hydrogen; and wherein if $R^8$ is cyclopropyl, then at least one of $R^{6a}$, $R^{6b}$, $R^{7b}$, and $R^{7x}$ is not hydrogen;

or a salt or stereoisomer thereof.

DETAILED DESCRIPTION

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions comprising these compounds, methods of using these compounds in the treatment of various diseases and disorders, processes for preparing these compounds and intermediates useful in these processes.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is specifically contemplated. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978.

The nomenclature used herein to name the subject compounds is illustrated in the Examples herein. This nomenclature has generally been derived using the commercially-available AutoNom software (MDL, San Leandro, Calif.).

TERMS

The following terms have the following meanings unless otherwise indicated. Any undefined terms have their art recognized meanings.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—$C(CH_3)_2CH_2CH_2$—), (—$C(CH_3)_2CH_2C(O)$—), (—$C(CH_3)_2CH_2C(O)NH$—), (—$CH(CH_3)CH_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, NR$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, herein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic, provided that the point of attachment is through an atom of the aromatic aryl group. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO₂-alkyl, —SO₂-substituted alkyl, —SO₂-aryl, —SO₂-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH₂.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N₃.

"Carboxyl," "carboxy" or "carboxylate" refers to —CO₂H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO₂-alkyl, —SO₂-substituted alkyl, —SO₂-aryl and —SO₂-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO₂-alkyl, —SO₂-substituted alkyl, —SO₂-aryl and —SO₂-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen, and sulfur within the ring. Such heteroaryl groups can have a single ring (e.g., pyridinyl, imidazolyl or furyl) or multiple condensed rings (e.g., indolizinyl, quinolinyl, benzimidazolyl or benzothienyl), wherein the condensed rings may or may not be aromatic and/or contain a heteroatom, provided that the point of attachment is through an atom of the aromatic heteroaryl group. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO₂-alkyl, —SO₂-substituted alkyl, —SO₂-aryl and —SO₂-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cylcoalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cylcoalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means e.g. that one of the counter ions for such divalent alkali earth ions can be an ionized form of a compound of the invention and the other a typical counter ion such as chloride, or two ionized compounds of the invention can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^7$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (e.g., salts having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when the hydrogen of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human animals, especially mammals.

The term "treating" or "treatment" as used herein means the treating or treatment of a disease or medical condition in a patient, such as a mammal (particularly a human) that includes: (a) preventing the disease or medical condition from occurring, i.e., prophylactic treatment of a patient; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient.

Representative Embodiments

The following substituents and values are intended to provide representative examples of various aspects and embodiments. These representative values are intended to further define and illustrate such aspects and embodiments and are not intended to exclude other embodiments or to limit the scope of this invention. In this regard, the representation that a particular value or substituent is preferred is not intended in any way to exclude other values or substituents from this invention unless specifically indicated.

These compounds may contain one or more chiral centers and therefore, the embodiments are directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions unless otherwise indicated, provided that the desired utility of the composition as a whole is not eliminated by the presence of such other isomers.

The compositions of the present disclosure include compounds of Formulae I-V, shown below. Pharmaceutical compositions and methods of the present disclosure also contemplate compounds of Formulae I-V.

Formula I

In one of its composition aspects, the present embodiments provide a compound of formula (I):

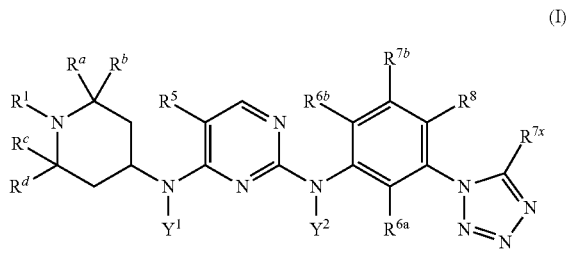

wherein $R^5$ is selected from haloalkyl, alkoxy, substituted alkoxy, cyano, halogen, acyl, aminoacyl, and nitro;

$Y^1$ and $Y^2$ are independently selected from hydrogen, alkyl, and acyl;

$R^1$ is selected from hydrogen, alkyl, and substituted alkyl;

$R^a$ and $R^b$ are independently selected from hydrogen and alkyl;

$R^c$ and $R^d$ are independently selected from hydrogen and alkyl;

$R^{6a}$ is selected from hydrogen, alkyl, substituted alkyl, cyano, halogen, acyl, aminoacyl, nitro, cycloalkyl, and substituted cycloalkyl;

$R^{6b}$ is selected from hydrogen, alkyl, substituted alkyl, cyano, halogen, acyl, aminoacyl, nitro, cycloalkyl, and substituted cycloalkyl;

$R^{7b}$ is selected from hydrogen, alkyl, substituted alkyl, cyano, halogen, acyl, aminoacyl, nitro, cycloalkyl, and substituted cycloalkyl;

$R^8$ is selected from hydrogen, $C_{2-10}$ alkyl, substituted alkyl, cyano, halogen, acyl, aminoacyl, nitro, cycloalkyl, and substituted cycloalkyl;

$R^{7x}$ is selected from hydrogen, alkyl, haloalkyl, cycloalkyl, and substituted cycloalkyl;

wherein at least one of $R^{6a}$, $R^{6b}$, $R^{7b}$, and $R^8$ is not hydrogen;

wherein if $R^8$ is fluoro, then $R^{7b}$ is not hydrogen; and wherein if $R^{7b}$ is cyclopropyl, then at least one of $R^{6a}$, $R^{6b}$, $R^8$, and $R^{7x}$ is not hydrogen; and wherein if $R^8$ is cyclopropyl, then at least one of $R^{6a}$, $R^{6b}$, $R^{7b}$, and $R^{7x}$ is not hydrogen;

or a salt or stereoisomer thereof.

Formula II

In one of its composition aspects, the present embodiments provide a compound of formula (II):

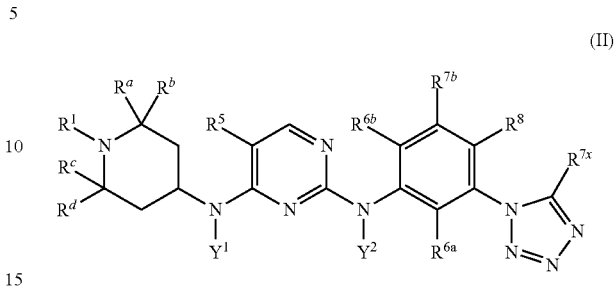

wherein $R^5$ is selected from haloalkyl, alkoxy, substituted alkoxy, cyano, halogen, acyl, aminoacyl, and nitro;

$Y^1$ and $Y^2$ are independently selected from hydrogen, alkyl, and acyl;

$R^1$ is selected from hydrogen, alkyl, and substituted alkyl;

$R^a$ and $R^b$ are independently selected from hydrogen and alkyl;

$R^c$ and $R^d$ are independently selected from hydrogen and alkyl;

$R^{6a}$ is selected from hydrogen, alkyl, substituted alkyl, cyano, halogen, acyl, aminoacyl, nitro, cycloalkyl, and substituted cycloalkyl;

$R^{6b}$ is selected from hydrogen, alkyl, substituted alkyl, cyano, halogen, acyl, aminoacyl, nitro, cycloalkyl, and substituted cycloalkyl;

$R^{7b}$ is selected from hydrogen, alkyl, substituted alkyl, cyano, halogen, acyl, aminoacyl, nitro, cycloalkyl, and substituted cycloalkyl;

$R^8$ is selected from hydrogen, $C_{2-10}$ alkyl, substituted alkyl, cyano, halogen, acyl, aminoacyl, nitro, cycloalkyl, and substituted cycloalkyl;

$R^{7x}$ is selected from hydrogen, alkyl, haloalkyl, cycloalkyl, and substituted cycloalkyl;

wherein at least one of $R^{6a}$ and $R^{6b}$ is not hydrogen;

or a salt or stereoisomer thereof.

Formula III

In one of its composition aspects, the present embodiments provide a compound of formula (III):

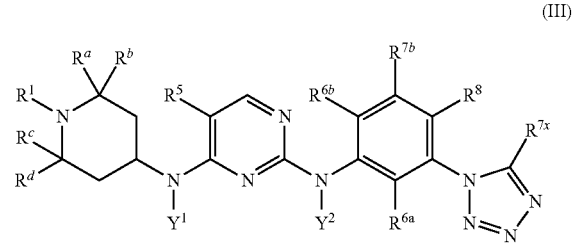

wherein $R^5$ is selected from haloalkyl, alkoxy, substituted alkoxy, cyano, halogen, acyl, aminoacyl, and nitro;

$Y^1$ and $Y^2$ are independently selected from hydrogen, alkyl, and acyl;

$R^1$ is selected from hydrogen, alkyl, and substituted alkyl;

$R^a$ and $R^b$ are independently selected from hydrogen and alkyl;

$R^c$ and $R^d$ are independently selected from hydrogen and alkyl;

$R^{6a}$ is selected from hydrogen, alkyl, substituted alkyl, cyano, halogen, acyl, aminoacyl, nitro, cycloalkyl, and substituted cycloalkyl;

$R^{6b}$ is selected from hydrogen, alkyl, substituted alkyl, cyano, halogen, acyl, aminoacyl, nitro, cycloalkyl, and substituted cycloalkyl;

$R^{7b}$ is selected from hydrogen, alkyl, substituted alkyl, cyano, halogen, acyl, aminoacyl, nitro, cycloalkyl, and substituted cycloalkyl;

$R^8$ is selected from hydrogen, $C_{2-10}$ alkyl, substituted alkyl, cyano, halogen, acyl, aminoacyl, nitro, cycloalkyl, and substituted cycloalkyl;

$R^{7x}$ is selected from hydrogen, alkyl, haloalkyl, alkyl, and substituted cycloalkyl;

wherein at least one of $R^{6a}$, $R^{6b}$, $R^{7b}$, and $R^8$ is halogen; and wherein at least one of $R^{6a}$, $R^{6b}$, $R^{7b}$, and $R^8$ is cycloalkyl, alkyl, or $C_{2-10}$ alkyl;

or a salt or stereoisomer thereof.

Formula IV

In one of its composition aspects, the present embodiments provide a compound of formula (IV):

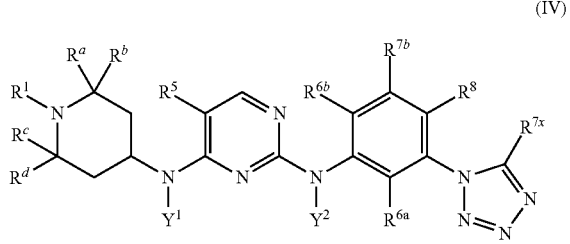

(IV)

wherein $R^5$ is selected from haloalkyl, alkoxy, substituted alkoxy, cyano, halogen, acyl, aminoacyl, and nitro;

$Y^1$ and $Y^2$ are independently selected from hydrogen, alkyl, and acyl;

$R^1$ is selected from hydrogen, alkyl, and substituted alkyl;

$R^a$ and $R^b$ are independently selected from hydrogen and alkyl;

$R^c$ and $R^d$ are independently selected from hydrogen and alkyl;

$R^{6a}$ is selected from hydrogen, alkyl, substituted alkyl, cyano, halogen, acyl, aminoacyl, nitro, cycloalkyl, and substituted cycloalkyl;

$R^{6b}$ is selected from hydrogen, alkyl, substituted alkyl, cyano, halogen, acyl, aminoacyl, nitro, cycloalkyl, and substituted cycloalkyl;

$R^{7b}$ is selected from hydrogen, alkyl, substituted alkyl, cyano, halogen, acyl, aminoacyl, nitro, cycloalkyl, and substituted cycloalkyl;

$R^8$ is selected from hydrogen, $C_{2-10}$ alkyl, substituted alkyl, cyano, halogen, acyl, aminoacyl, nitro, cycloalkyl, and substituted cycloalkyl;

$R^{7x}$ is selected from hydrogen, alkyl, haloalkyl, cycloalkyl, and substituted cycloalkyl;

wherein at least one of $R^{6a}$, $R^{6b}$, $R^{7b}$, and $R^8$ is $C_{2-10}$ alkyl;

or a salt or stereoisomer thereof.

Formula V

In one of its composition aspects, the present embodiments provide a compound of formula (V):

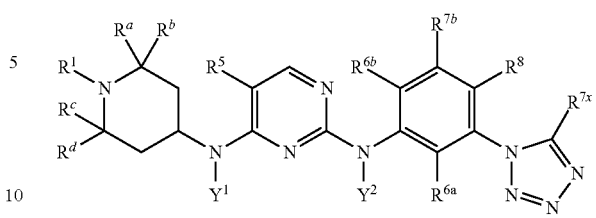

(V)

wherein $R^5$ is selected from haloalkyl, alkoxy, substituted alkoxy, cyano, halogen, acyl, aminoacyl, and nitro;

$Y^1$ and $Y^2$ are independently selected from hydrogen, alkyl, and acyl;

$R^1$ is selected from hydrogen, alkyl, and substituted alkyl;

$R^a$ and $R^b$ are independently selected from hydrogen and alkyl;

$R^c$ and $R^d$ are independently selected from hydrogen and alkyl;

$R^{6a}$ is selected from hydrogen, alkyl, substituted alkyl, cyano, halogen, acyl, aminoacyl, nitro, cycloalkyl, and substituted cycloalkyl;

$R^{6b}$ is selected from hydrogen, alkyl, substituted alkyl, cyano, halogen, acyl, aminoacyl, nitro, cycloalkyl, and substituted cycloalkyl;

$R^{7b}$ is selected from hydrogen, alkyl, substituted alkyl, cyano, halogen, acyl, aminoacyl, nitro, cycloalkyl, and substituted cycloalkyl;

$R^8$ is selected from hydrogen, $C_{2-10}$ alkyl, substituted alkyl, cyano, halogen, acyl, aminoacyl, nitro, cycloalkyl, and substituted cycloalkyl;

$R^{7x}$ is haloalkyl;

or a salt or stereoisomer thereof.

In formulae I-V, $R^5$ can be selected from haloalkyl, alkoxy, substituted alkoxy, cyano, halogen, acyl, aminoacyl, and nitro. In certain instances, $R^5$ is haloalkyl. In certain instances, $R^5$ is alkoxy or substituted alkoxy. In certain instances, $R^5$ is cyano. In certain instances, $R^5$ is halogen. In certain instances, $R^5$ is fluoro, chloro, bromo, or iodo. In certain instances, $R^5$ is fluoro. In certain instances, $R^5$ is acyl or acylamino. In certain instances, $R^5$ is —$CONH_2$. In certain instances, $R^5$ is nitro.

In formulae I-V, $Y^1$ and $Y^2$ can independently be selected from hydrogen, alkyl, and acyl. In certain instances, $Y^1$ is hydrogen. In certain instances, $Y^1$ is alkyl. In certain instances, $Y^1$ is acyl. In certain instances, $Y^2$ is hydrogen. In certain instances, $Y^2$ is alkyl. In certain instances, $Y^2$ is acyl.

In formulae I-V, $R^1$ can be selected from hydrogen, alkyl, and substituted alkyl. In certain instances, $R^1$ is hydrogen or alkyl. In certain instances, $R^1$ is hydrogen. In certain instances, $R^1$ is alkyl. In certain instances, $R^1$ is methyl.

In formulae I-V, $R^a$ and $R^b$ can be independently selected from hydrogen and alkyl. In certain instances, $R^a$ and $R^b$ are both alkyl. In certain instances, $R^a$ and $R^b$ are both methyl. In certain instances, at least one of $R^a$ and $R^b$ is alkyl.

In formulae I-V, $R^c$ and $R^d$ can be independently selected from hydrogen and alkyl. In certain instances, $R^c$ and $R^d$ are both alkyl. In certain instances, $R^c$ and $R^d$ are both methyl. In certain instances, at least one of $R^c$ and $R^d$ is alkyl.

In formulae I-V, in certain instances, at least one of $R^{6a}$, $R^{6b}$, $R^{7b}$, and $R^8$ is selected from $C_{2-10}$ alkyl, halogen, and cycloalkyl.

In formulae I-V, $R^{6a}$ can be selected from hydrogen, alkyl, substituted alkyl, cyano, halogen, acyl, aminoacyl, nitro, cycloalkyl, and substituted cycloalkyl. In certain instance, $R^{6a}$ is hydrogen, alkyl, halogen, or cycloalkyl.

In formulae I-V, in certain instances, $R^{6a}$ is hydrogen. In certain instances, $R^{6a}$ is alkyl. In certain instances, $R^{6a}$ is ethyl, propyl, isopropyl, butyl, sec-butyl, or isobutyl. In certain instances, $R^{6a}$ is isopropyl. In certain instances, $R^{6a}$ is halogen. In certain instances, $R^{6a}$ is fluoro, chloro, bromo, or iodo. In certain instances, $R^{6a}$ is fluoro. In certain instances, $R^{6a}$ is cycloalkyl. In certain instances, $R^{6a}$ is cyclopropyl.

In formulae I-V, in certain instances, $R^{6a}$ is substituted alkyl. In certain instances, $R^{6a}$ is substituted cycloalkyl. In certain instances, $R^{6a}$ is cyano, acyl, aminoacyl, or nitro.

In formulae I-V, $R^{6b}$ can be selected from hydrogen, alkyl, substituted alkyl, cyano, halogen, acyl, aminoacyl, nitro, cycloalkyl, and substituted cycloalkyl. In certain instance, $R^{6b}$ is hydrogen, alkyl, halogen, or cycloalkyl.

In formulae I-V, in certain instances, $R^{6b}$ is hydrogen. In certain instances, $R^{6b}$ is alkyl. In certain instances, $R^{6b}$ is ethyl, propyl, isopropyl, butyl, sec-butyl, or isobutyl. In certain instances, $R^{6b}$ is isopropyl. In certain instances, $R^{6b}$ is halogen. In certain instances, $R^{6b}$ is fluoro, chloro, bromo, or iodo. In certain instances, $R^{6b}$ is fluoro. In certain instances, $R^{6b}$ is cycloalkyl. In certain instances, $R^{6b}$ is cyclopropyl.

In formulae I-V, in certain instances, $R^{6b}$ is substituted alkyl. In certain instances, $R^{6b}$ is substituted cycloalkyl. In certain instances, $R^{6b}$ is cyano, acyl, aminoacyl, or nitro.

In formulae I-V, $R^{7b}$ can be selected from hydrogen, alkyl, substituted alkyl, cyano, halogen, acyl, aminoacyl, nitro, cycloalkyl, and substituted cycloalkyl. In certain instance, $R^{7b}$ is hydrogen, alkyl, halogen, or cycloalkyl.

In formulae I-V, in certain instances, $R^{7b}$ is hydrogen. In certain instances, $R^{7b}$ is alkyl. In certain instances, $R^{7b}$ is ethyl, propyl, isopropyl, butyl, sec-butyl, or isobutyl. In certain instances, $R^{7b}$ is isopropyl. In certain instances, $R^{7b}$ is halogen. In certain instances, $R^{7b}$ is fluoro, chloro, bromo, or iodo. In certain instances, $R^{7b}$ is fluoro. In certain instances, $R^{7b}$ is cycloalkyl. In certain instances, $R^{7b}$ is cyclopropyl.

In formulae I-V, in certain instances, $R^{7b}$ is substituted alkyl. In certain instances, $R^{7b}$ is substituted cycloalkyl. In certain instances, $R^{7b}$ is cyano, acyl, aminoacyl, or nitro.

In formulae I-V, $R^8$ can be selected from hydrogen, $C_{2-10}$ alkyl, substituted alkyl, cyano, halogen, acyl, aminoacyl, nitro, cycloalkyl, and substituted cycloalkyl. In certain instance, $R^8$ is hydrogen, $C_{2-10}$ alkyl, halogen, cycloalkyl, or substituted cycloalkyl.

In formulae I-V, in certain instances, $R^8$ is hydrogen. In certain instances, $R^8$ is $C_{2-10}$ alkyl. In certain instances, $R^8$ is ethyl, propyl, isopropyl, butyl, sec-butyl, or isobutyl. In certain instances, $R^8$ is isopropyl. In certain instances, $R^8$ is halogen. In certain instances, $R^8$ is fluoro, chloro, bromo, or iodo. In certain instances, $R^8$ is fluoro. In certain instances, $R^8$ is cycloalkyl. In certain instances, $R^8$ is cyclopropyl. In certain instances, $R^8$ is substituted cycloalkyl. In certain instances, $R^8$ is substituted cycloalkyl, wherein the substituent is haloalkyl. In certain instances, $R^8$ is substituted cyclopropyl. In certain instances, $R^8$ is substituted cyclopropyl, wherein the substituent is haloalkyl. Examples of haloalkyl substituents on a cycloalkyl ring include trifluoromethyl, difluoromethyl, and fluoromethyl.

In formulae I-V, in certain instances, $R^8$ is substituted alkyl. In certain instances, $R^8$ is cyano, acyl, aminoacyl, or nitro.

In formulae I-IV, $R^{7x}$ can be selected from hydrogen, alkyl, haloalkyl, cycloalkyl, and substituted cycloalkyl. In certain instances, $R^{7x}$ is hydrogen. In certain instances, $R^{7x}$ is alkyl. In certain instances, $R^{7x}$ is methyl, ethyl, propyl, or isopropyl. In certain instances, $R^{7x}$ is methyl. In certain instances, $R^{7x}$ is ethyl. In certain instances, $R^{7x}$ is propyl. In certain instances, $R^{7x}$ is isopropyl. In certain instances, $R^{7x}$ is haloalkyl. In certain instances, $R^{7x}$ is trifluoromethyl or fluoromethyl. In certain instances, $R^{7x}$ is trifluoromethyl. In certain instances, $R^{7x}$ is fluoromethyl. In certain instances, $R^{7x}$ is cycloalkyl. In certain instances, $R^{7x}$ is substituted cycloalkyl. In certain instances, $R^{7x}$ is cyclopropyl.

In formula I:
at least one of $R^{6a}$, $R^{6b}$, $R^{7b}$, and $R^8$ is not hydrogen;
if $R^8$ is fluoro, then $R^{7b}$ is not hydrogen;
if $R^{7b}$ is cyclopropyl, then at least one of $R^{6a}$, $R^{6b}$, $R^8$, and $R^{7x}$ is not hydrogen; and
if $R^8$ is cyclopropyl, then at least one of $R^{6a}$, $R^{6b}$, $R^{7b}$, and $R^{7x}$ is not hydrogen.

In formula II, at least one of $R^{6a}$ and $R^{6b}$ is not hydrogen. In certain instances, in formulae I and II, at least one of $R^{6a}$ and $R^{6b}$ is halogen. In certain instances, at least one of $R^{6a}$ and $R^{6b}$ is fluoro, chloro, bromo, or iodo. In certain instances, at least one of $R^{6a}$ and $R^{6b}$ is fluoro. In certain instances of formulae I and II, one of $R^{6a}$ and $R^{6b}$ is fluoro and the other is hydrogen.

In certain instances, in formulae I and II, at least one of $R^{6a}$ and $R^{6b}$ is $C_{2-10}$ alkyl. In certain instances, at least one of $R^{6a}$ and $R^{6b}$ is ethyl, propyl, isopropyl, butyl, sec-butyl, or isobutyl. In certain instances, at least one of $R^{6a}$ and $R^{6b}$ is isopropyl. In certain instances, at least one of $R^{6a}$ and $R^{6b}$ is cycloalkyl. In certain instances, at least one of $R^{6a}$ and $R^{6b}$ is cyclopropyl. In certain instances, at least one of $R^{6a}$ and $R^{6b}$ is substituted alkyl. In certain instances, at least one of $R^{6a}$ and $R^{6b}$ is substituted cycloalkyl. In certain instances, at least one of $R^{6a}$ and $R^{6b}$ is cyano, acyl, aminoacyl, or nitro.

In formula III, at least one of $R^{6a}$, $R^{6b}$, $R^{7b}$, and $R^8$ is halogen and at least one of $R^{6a}$, $R^{6b}$, $R^{7b}$, and $R^8$ is cycloalkyl or $C_{2-10}$ alkyl. In certain instances, in formulae I and III, at least one of $R^{6a}$, $R^{6b}$, $R^{7b}$, and $R^8$ is halogen and at least one of $R^{6a}$, $R^{6b}$, $R^{7b}$, and $R^8$ is cycloalkyl. In certain instances, at least one of $R^{6a}$, $R^{6b}$, $R^{7b}$, and $R^8$ is halogen and at least one of $R^{6a}$, $R^{6b}$, $R^{7b}$ and $R^8$ is $C_{2-10}$ alkyl. In certain instances of formula III, at least one of $R^{6a}$ and $R^{6b}$ is fluoro and the other is hydrogen.

In certain instances, in formulae I and III, at least one of $R^{6a}$, $R^{6b}$, $R^{7b}$, and $R^8$ is fluoro and at least one of $R^{6a}$, $R^{6b}$, $R^{7b}$, and $R^8$ is cycloalkyl. In certain instances, at least one of $R^{6a}$, $R^{6b}$, $R^{7b}$, and $R^8$ is fluoro and at least one of $R^{6a}$, $R^{6b}$, $R^{7b}$, and $R^8$ is cyclopropyl. In certain instances, at least one of $R^{6a}$, $R^{6b}$, $R^{7b}$, and $R^8$ is fluoro and at least one of $R^{6a}$, $R^{6b}$, $R^{7b}$, and $R^8$ is $C_{2-10}$ alkyl. In certain instances, at least one of $R^{6a}$, $R^{6b}$, $R^{7b}$, and $R^8$ is fluoro and at least one of $R^{6a}$, $R^{6b}$, $R^{7b}$, and $R^8$ is ethyl, propyl, isopropyl, butyl, sec-butyl, or isobutyl. In certain instances, at least one of $R^{6a}$, $R^{6b}$, $R^{7b}$, and $R^8$ is fluoro and at least one of $R^{6a}$, $R^{6b}$, $R^{7b}$, and $R^8$ is isopropyl.

In certain instances, in formulae I and III, at least one of $R^{6a}$, $R^{6b}$, $R^{7b}$, and $R^8$ is halogen and at least one of $R^{6a}$, $R^{6b}$, $R^{7b}$, and $R^8$ is cyclopropyl. In certain instances, at least one of $R^{6a}$, $R^{6b}$, $R^{7b}$, and $R^8$ is halogen and at least one of $R^{6a}$, $R^{6b}$, $R^{7b}$, and $R^8$ is ethyl, propyl, isopropyl, butyl, sec-butyl, or isobutyl. In certain instances, at least one of $R^{6a}$, $R^{6b}$, $R^{7b}$, and $R^8$ is halogen and at least one of $R^{6a}$, $R^{6b}$, $R^{7b}$, and $R^8$ is isopropyl.

In formula IV, at least one of $R^{6a}$, $R^{6b}$, $R^{7b}$, and $R^8$ is $C_{2-10}$ alkyl. In certain instances, in formulae I and IV, at least one of $R^{6a}$, $R^{6b}$, $R^{7b}$, and $R^8$ is ethyl, propyl, isopropyl, butyl, sec-butyl, or isobutyl. In certain instances, at least one of $R^{6a}$, $R^{6b}$, $R^{7b}$, and $R^8$ is isopropyl.

Particular compounds of interest are illustrated in the following table.

TABLE 1

| cmpd | R¹ | Rᵃ/Rᵇ | Rᶜ/Rᵉ | Y | R⁵ | R⁶ᵃ | R⁶ᵇ | R⁷ᵇ | R⁸ | R⁷ˣ |
|---|---|---|---|---|---|---|---|---|---|---|
| I-1 | —H | —CH₃/—CH₃ | —CH₃/—CH₃ | —H | —F | —H | —F | —H | cyclopropyl | —H |
| I-2 | —H | —CH₃/—CH₃ | —CH₃/—CH₃ | —H | —CN | —H | —F | —H | cyclopropyl | —H |
| I-3 | —H | —CH₃/—CH₃ | —CH₃/—CH₃ | —H | —CONH₂ | —H | —F | —H | cyclopropyl | —H |
| I-4 | —H | —CH₃/—CH₃ | —CH₃/—CH₃ | —H | —CN | —H | —H | —F | cyclopropyl | —H |
| I-5 | —H | —CH₃/—CH₃ | —CH₃/—CH₃ | —H | —F | —H | —H | —F | cyclopropyl | —H |
| I-6 | —H | —CH₃/—CH₃ | —CH₃/—CH₃ | —H | —CN | —H | —H | cyclopropyl | —F | —H |
| I-7 | —H | —CH₃/—CH₃ | —CH₃/—CH₃ | —H | —F | —H | —H | cyclopropyl | —F | —H |
| I-8 | —H | —CH₃/—CH₃ | —CH₃/—CH₃ | —H | —CN | —H | —F | —H | isopropyl | —H |
| I-9 | —H | —CH₃/—CH₃ | —CH₃/—CH₃ | —H | —F | —H | —H | —H | isopropyl | —H |
| I-10 | —H | —CH₃/—CH₃ | —CH₃/—CH₃ | —H | —CONH₂ | —H | —H | —H | isopropyl | —H |
| I-11 | —H | —CH₃/—CH₃ | —CH₃/—CH₃ | —H | —CN | —H | —H | —H | isopropyl | —H |
| I-12 | —H | —CH₃/—CH₃ | —CH₃/—CH₃ | —H | —F | —H | —F | —H | cyclopropyl | —H |
| I-13 | —H | —CH₃/—CH₃ | —CH₃/—CH₃ | —H | —F | —H | —F | —H | —H | —H |

TABLE 1-continued

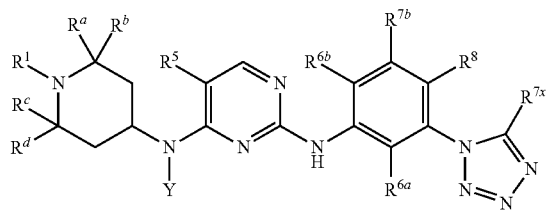

| cmpd | R¹ | Rᵃ/Rᵇ | Rᶜ/Rᵉ | Y | R⁵ | R⁶ᵃ | R⁶ᵇ | R⁷ᵇ | R⁸ | R⁷ˣ |
|---|---|---|---|---|---|---|---|---|---|---|
| I-14 | —CH₃ | —CH₃/—CH₃ | —CH₃/—CH₃ | —H | —F | —H | —F | —H | —H | —H |
| I-15 | —H | —CH₃/—CH₃ | —CH₃/—CH₃ | —H | —F | —H | —H | —H | cyclopropyl | —CF₃ |
| I-16 | —H | —CH₃/—CH₃ | —CH₃/—CH₃ | —H | —F | —H | —F | —H | cyclopropyl | isopropyl |
| I-17 | —H | —CH₃/—CH₃ | —CH₃/—CH₃ | —H | —F | —H | —F | —H | cyclopropyl | cyclopropyl |
| I-18 | —H | —CH₃/—CH₃ | —CH₃/—CH₃ | —H | —F | —H | —F | —H | cyclopropyl | —CH₃ |
| I-19 | —H | —CH₃/—CH₃ | —CH₃/—CH₃ | —H | —F | —H | —F | —H | cyclopropyl | —CF₃ |
| I-20 | —H | —CH₃/—CH₃ | —CH₃/—CH₃ | —H | —F | —H | —F | —H | cyclopropyl | —CH₂F |
| I-21 | —H | —CH₃/—CH₃ | —CH₃/—CH₃ | —H | —F | —H | —F | —H | cyclopropyl-CF₃ | —H |

Particular compounds of interest, and salts or solvates or stereoisomers thereof, include:

I-1: N2-(4-cyclopropyl-2-fluoro-5-tetrazol-1-yl-phenyl)-5-fluoro-N4-(2,2,6,6-tetramethyl-piperidin-4-yl)-pyrimidine-2,4-diamine;

I-2: 2-(4-cyclopropyl-2-fluoro-5-tetrazol-1-yl-phenylamino)-4-(2,2,6,6-tetramethyl-piperidin-4-ylamino)-pyrimidine-5-carbonitrile;

I-3: 2-(4-cyclopropyl-2-fluoro-5-tetrazol-1-yl-phenylamino)-4-(2,2,6,6-tetramethyl-piperidin-4-ylamino)-pyrimidine-5-carboxylic acid amide;

I-4: 2-(4-cyclopropyl-3-fluoro-5-tetrazol-1-yl-phenylamino)-4-(2,2,6,6-tetramethyl-piperidin-4-ylamino)-pyrimidine-5-carbonitrile;

I-5: N2-(4-cyclopropyl-3-fluoro-5-tetrazol-1-yl-phenyl)-5-fluoro-N4-(2,2,6,6-tetramethyl-piperidin-4-yl)-pyrimidine-2,4-diamine;

I-6: 2-(3-cyclopropyl-4-fluoro-5-tetrazol-1-yl-phenylamino)-4-(2,2,6,6-tetramethyl-piperidin-4-ylamino)-pyrimidine-5-carbonitrile;

I-7: N2-(3-cyclopropyl-4-fluoro-5-tetrazol-1-yl-phenyl)-5-fluoro-N4-(2,2,6,6-tetramethyl-piperidin-4-yl)-pyrimidine-2,4-diamine;

I-8: 2-(2-fluoro-4-isopropyl-5-tetrazol-1-yl-phenylamino)-4-(2,2,6,6-tetramethyl-piperidin-4-ylamino)-pyrimidine-5-carbonitrile;

I-9: 5-fluoro-N2-(4-isopropyl-3-tetrazol-1-yl-phenyl)-N4-(2,2,6,6-tetramethyl-piperidin-4-yl)-pyrimidine-2,4-diamine;

I-10: 2-(4-isopropyl-3-tetrazol-1-yl-phenylamino)-4-(2,2,6,6-tetramethyl-piperidin-4-ylamino)-pyrimidine-5-carboxylic acid amide;

I-11: 2-(4-isopropyl-3-tetrazol-1-yl-phenylamino)-4-(2,2,6,6-tetramethyl-piperidin-4-ylamino)-pyrimidine-5-carbonitrile;

I-12: N2-(4-cyclopropyl-2-fluoro-5-tetrazol-1-yl-phenyl)-5-fluoro-N4-(2,2,6,6-tetramethyl-piperidin-4-yl)-pyrimidine-2,4-diamine;

I-13: 5-fluoro-N2-(2-fluoro-5-tetrazol-1-yl-phenyl)-N4-(2,2,6,6-tetramethyl-piperidin-4-yl)-pyrimidine-2,4-diamine;

I-14: 5-fluoro-N2-(2-fluoro-5-tetrazol-1-yl-phenyl)-N4-(1,2,2,6,6-pentamethyl-piperidin-4-yl)-pyrimidine-2,4-diamine; and I-15: N2-[4-cyclopropyl-3-(5-trifluoromethyl-tetrazol-1-yl)-phenyl]-5-fluoro-N4-(2,2,6,6-tetramethyl-piperidin-4-yl)-pyrimidine-2,4-diamine; or a solvate, prodrug, or a pharmaceutically acceptable salt thereof.

Particular compounds of interest, and salts or solvates or stereoisomers thereof, include:

I-16: N2-(4-cyclopropyl-2-fluoro-5-(5-isopropyl-1H-tetrazol-1-yl)phenyl)-5-fluoro-N4-(2,2,6,6-tetramethylpiperidin-4-yl)pyrimidine-2,4-diamine;

I-17: N2-(4-cyclopropyl-5-(5-cyclopropyl-1H-tetrazol-1-yl)-2-fluorophenyl)-5-fluoro-N4-(2,2,6,6-tetramethylpiperidin-4-yl)pyrimidine-2,4-diamine;

I-18: N2-(4-cyclopropyl-2-fluoro-5-(5-methyl-1H-tetrazol-1-yl)phenyl)-5-fluoro-N4-(2,2,6,6-tetramethylpiperidin-4-yl)pyrimidine-2,4-diamine;

I-19: N2-(4-cyclopropyl-2-fluoro-5-(5-(trifluoromethyl)-1H-tetrazol-1-yl)phenyl)-5-fluoro-N4-(2,2,6,6-tetramethylpiperidin-4-yl)pyrimidine-2,4-diamine;

I-20: N2-(4-cyclopropyl-2-fluoro-5-(5-(fluoromethyl)-1H-tetrazol-1-yl)phenyl)-5-fluoro-N4-(2,2,6,6-tetramethylpiperidin-4-yl)pyrimidine-2,4-diamine; and I-21: trans-5-fluoro-N2-(2-fluoro-5-(1H-tetrazol-1-yl)-4-(2-(trifluoromethyl)cyclopropyl)phenyl)-N4-(2,2,6,6-tetramethylpiperidin-4-yl)pyrimidine-2,4-diamine;

or a solvate, prodrug, or a pharmaceutically acceptable salt thereof.

Particular compounds of interest, and salts or solvates or stereoisomers thereof, include:

I-1: N2-(4-cyclopropyl-2-fluoro-5-tetrazol-1-yl-phenyl)-5-fluoro-N4-(2,2,6,6-tetramethyl-piperidin-4-yl)-pyrimidine-2,4-diamine;

I-2: 2-(4-cyclopropyl-2-fluoro-5-tetrazol-1-yl-phenylamino)-4-(2,2,6,6-tetramethyl-piperidin-4-ylamino)-pyrimidine-5-carbonitrile;

I-3: 2-(4-cyclopropyl-2-fluoro-5-tetrazol-1-yl-phenylamino)-4-(2,2,6,6-tetramethyl-piperidin-4-ylamino)-pyrimidine-5-carboxylic acid amide;

I-4: 2-(4-cyclopropyl-3-fluoro-5-tetrazol-1-yl-phenylamino)-4-(2,2,6,6-tetramethyl-piperidin-4-ylamino)-pyrimidine-5-carbonitrile;

I-5: N2-(4-cyclopropyl-3-fluoro-5-tetrazol-1-yl-phenyl)-5-fluoro-N4-(2,2,6,6-tetramethyl-piperidin-4-yl)-pyrimidine-2,4-diamine;

I-6: 2-(3-cyclopropyl-4-fluoro-5-tetrazol-1-yl-phenylamino)-4-(2,2,6,6-tetramethyl-piperidin-4-ylamino)-pyrimidine-5-carbonitrile;

I-7: N2-(3-cyclopropyl-4-fluoro-5-tetrazol-1-yl-phenyl)-5-fluoro-N4-(2,2,6,6-tetramethyl-piperidin-4-yl)-pyrimidine-2,4-diamine;

I-8: 2-(2-fluoro-4-isopropyl-5-tetrazol-1-yl-phenylamino)-4-(2,2,6,6-tetramethyl-piperidin-4-ylamino)-pyrimidine-5-carbonitrile;

I-9: 5-fluoro-N2-(4-isopropyl-3-tetrazol-1-yl-phenyl)-N4-(2,2,6,6-tetramethyl-piperidin-4-yl)-pyrimidine-2,4-diamine;

I-10: 2-(4-isopropyl-3-tetrazol-1-yl-phenylamino)-4-(2,2,6,6-tetramethyl-piperidin-4-ylamino)-pyrimidine-5-carboxylic acid amide;

I-11: 2-(4-isopropyl-3-tetrazol-1-yl-phenylamino)-4-(2,2,6,6-tetramethyl-piperidin-4-ylamino)-pyrimidine-5-carbonitrile;

I-12: N2-(4-cyclopropyl-2-fluoro-5-tetrazol-1-yl-phenyl)-5-fluoro-N4-(2,2,6,6-tetramethyl-piperidin-4-yl)-pyrimidine-2,4-diamine;

I-13: 5-fluoro-N2-(2-fluoro-5-tetrazol-1-yl-phenyl)-N4-(2,2,6,6-tetramethyl-piperidin-4-yl)-pyrimidine-2,4-diamine;

I-14: 5-fluoro-N2-(2-fluoro-5-tetrazol-1-yl-phenyl)-N4-(1,2,2,6,6-pentamethyl-piperidin-4-yl)-pyrimidine-2,4-diamine;

I-15: N2-[4-cyclopropyl-3-(5-trifluoromethyl-tetrazol-1-yl)-phenyl]-5-fluoro-N4-(2,2,6,6-tetramethyl-piperidin-4-yl)-pyrimidine-2,4-diamine;

I-16: N2-(4-cyclopropyl-2-fluoro-5-(5-isopropyl-1H-tetrazol-1-yl)phenyl)-5-fluoro-N4-(2,2,6,6-tetramethylpiperidin-4-yl)pyrimidine-2,4-diamine;

I-17: N2-(4-cyclopropyl-5-(5-cyclopropyl-1H-tetrazol-1-yl)-2-fluorophenyl)-5-fluoro-N4-(2,2,6,6-tetramethylpiperidin-4-yl)pyrimidine-2,4-diamine; and I-18: N2-(4-cyclopropyl-2-fluoro-5-(5-methyl-1H-tetrazol-1-yl)phenyl)-5-fluoro-N4-(2,2,6,6-tetramethylpiperidin-4-yl)pyrimidine-2,4-diamine;

I-19: N2-(4-cyclopropyl-2-fluoro-5-(5-(trifluoromethyl)-1H-tetrazol-1-yl)phenyl)-5-fluoro-N4-(2,2,6,6-tetramethylpiperidin-4-yl)pyrimidine-2,4-diamine;

I-20: N2-(4-cyclopropyl-2-fluoro-5-(5-(fluoromethyl)-1H-tetrazol-1-yl)phenyl)-5-fluoro-N4-(2,2,6,6-tetramethylpiperidin-4-yl)pyrimidine-2,4-diamine; and I-21: trans-5-fluoro-N2-(2-fluoro-5-(1H-tetrazol-1-yl)-4-(2-(trifluoromethyl)cyclopropyl)phenyl)-N4-(2,2,6,6-tetramethylpiperidin-4-yl)pyrimidine-2,4-diamine;

or a solvate, prodrug, or a pharmaceutically acceptable salt thereof.

The compounds described also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{14}C$, $^{15}N$, $^{18}O$, $^{17}O$, etc. Thus, the disclosed compounds may be enriched in one or more of these isotopes relative to the natural abundance of such isotope. By way of example, deuterium ($^2H$) has a natural abundance of about 0.015%. Accordingly, for approximately every 6,500 hydrogen atoms occurring in nature, there is one deuterium atom. Specifically contemplated herein are compounds enriched in deuterium at one or more positions. Thus, deuterium containing compounds of the disclosure have deuterium at one or more positions (as the case may be) in an abundance of greater than 0.015%.

Compounds may exist in unsolvated forms as well as solvated forms, including hydrated forms. In general, compounds may be hydrated or solvated. Certain compounds may exist in multiple crystalline or amorphous forms. In general, all physical forms are equivalent for the uses contemplated herein and are intended to be within the scope of the present disclosure.

The present disclosure also provides pharmaceutical compositions comprising a pharmaceutically acceptable carrier and a therapeutically effective amount of a compound of Formulae I-V or a pharmaceutically acceptable salt or solvate or stereoisomer thereof.

A disclosed compound can be administered alone, as the sole active pharmaceutical agent, or in combination with one or more additional compounds of Formulae I-V or in conjunction with other agents. When administered as a combination, the therapeutic agents can be formulated as separate compositions that are administered simultaneously or at different times, or the therapeutic agents can be administered together as a single composition combining two or more therapeutic agents. Thus, the pharmaceutical compositions disclosed herein containing a compound of Formulae I-V optionally contain other therapeutic agents. Accordingly, certain embodiments are directed to such pharmaceutical composition, wherein the composition further comprises a therapeutically effective amount of an agent selected as is known to those of skill in the art.

The subject compounds can inhibit a protein kinase C activity. Accordingly, the compounds are useful for treating a disease or disorder that is mediated through the activity of a PKC activity in a subject. Also, the compounds are useful for treating a disease or disorder that is associated with the activation of T-cells in a subject.

The present disclosure provides a method of treating an inflammatory disease in a subject, the method comprising administering to the subject with a compound of Formulae I-V or a salt or solvate or stereoisomer thereof.

The present disclosure also provides a method of treating an autoimmune disease in a subject, the method comprising administering to the subject with a compound of Formulae I-V or a salt or solvate or stereoisomer thereof.

The present disclosure also provides a method of treating an ocular disease or disorder involving inflammatory and/or neovascular events.

The present disclosure also provides a method of treating diseases or conditions of interest including, but are not limited to, atherosclerosis, vascular occlusion due to vascular injury, angioplasty, restenosis, obesity, syndrome X, impaired glucose tolerance, polycystic ovary syndrome, hypertension, heart failure, chronic obstructive pulmonary disease, CNS diseases, Alzheimer disease, amyotrophic lateral sclerosis, bipolar disease, cancer, infectious disease, AIDS, septic shock, adult respiratory distress syndrome, ischemia/reperfusion injury, myocardial infarction, stroke, gut ischemia, renal failure, hemorrhage shock, and traumatic shock, and traumatic brain injury.

The present disclosure also provides a method of treating diseases or conditions of interest including, but are not limited to, T-cell mediated acute or chronic inflammatory diseases or disorders or autoimmune diseases, rheumatoid arthritis, osteoarthritis, systemic lupus erythematosus, Hashimoto's thyroiditis, multiple sclerosis, myasthenia gravis, diabetes type I or II and the disorders associated therewith, transplant rejection, graft versus host disease, respiratory diseases, asthma, inflammatory lung injury, inflammatory liver injury, inflammatory glomerular injury, cutaneous manifestations of immunologically-mediated disorders or illnesses, inflammatory and hyperproliferative skin diseases, psoriasis, atopic dermatitis, allergic contact dermatitis, irritant contact dermatitis and further eczematous dermatitises, seborrhoeic dermatitis, inflammatory eye diseases, Sjoegren's syndrome, keratoconjunctivitis, uveitis, inflammatory bowel disease, Crohn's disease or ulcerative colitis, Guillain-Barre syndrome, and allergies.

The subject compounds can be used for treating a cell proliferative disorder. The present disclosure also provides a method of treating diseases or conditions of interest including, but are not limited to, hematopoietic neoplasm, lymphoid neoplasm, T cell neoplasm, T lymphoblastic leukemia, B cell neoplasm, B-lymphoblastic leukemia, Burkitt's lymphoma, myeloid neoplasm, myeloproferative disease, chronic myelogenous leukemia (CML), myelodysplastic disease, chronic myelomonocytic leukemia, myelodysplastic syndrome, and acute myeloid leukemia.

Since subject compounds possess PKC inhibitory properties, such compounds are also useful as research tools. Accordingly, the disclosure also provides for a method for using a compound of Formulae I-V or a salt or solvate or stereoisomer thereof as a research tool for studying a biological system or sample, or for discovering new chemical compounds having PKC inhibitory properties.

The embodiments are also directed to processes and novel intermediates useful for preparing compounds of Formulae I-V or a salt or solvate or stereoisomer thereof.

In one embodiment, the above process further comprises the step of forming a salt of a compound of Formulae I-V. Embodiments are directed to the other processes described herein; and to the product prepared by any of the processes described herein.

The embodiments are also directed to a compound of Formulae I-V or a salt or solvate or stereoisomer thereof, for use in therapy or as a medicament.

Additionally, the embodiments are directed to the use of a compound of Formulae I-V or a salt or solvate or stereoisomer thereof, for the manufacture of a medicament; especially for the manufacture of a medicament for the inhibition of protein kinase C (PKC) activity. The embodiments are also directed to the use of a compound of Formulae I-V or a salt or solvate or stereoisomer thereof for the manufacture of a medicament for the treatment of a disease or disorder mediated or sustained through the activity of PKC activity. The embodiments are also directed to the use of a compound of Formulae I-V or a salt or solvate or stereoisomer thereof for the manufacture of a medicament for the treatment of a disease or disorder associated with the activation of T-cells. Diseases or conditions of interest include, but are not limited to, an inflammatory disease, an immunological disorder, an autoimmune disease, an ocular disease or disorder involving inflammatory and/or neovascular events, organ and bone marrow transplant rejection, acute or chronic inflammation, allergies, contact dermatitis, psoriasis, rheumatoid arthritis, multiple sclerosis, type I diabetes, type II diabetes, inflammatory bowel disease, Guillain-Barre syndrome, Crohn's disease, ulcerative colitis, graft versus host disease, and lupus erythematosus.

The embodiments are also directed to the use of a compound of Formulae I-V or a salt or solvate or stereoisomer thereof for the manufacture of a medicament for the treatment of a cell proliferative disorder. Diseases or conditions of interest include, but are not limited to, hematopoietic neoplasm, lymphoid neoplasm, T cell neoplasm, T lymphoblastic leukemia, B cell neoplasm, B-lymphoblastic leukemia, Burkitt's lymphoma, myeloid neoplasm, myeloproferative disease, chronic myelogenous leukemia (CML), myelodysplastic disease, chronic myelomonocytic leukemia, myelodysplastic syndrome, acute myeloid leukemia.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4$^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. Suitable exemplary methods that can be routinely adapted to synthesize the 2,4-pyrimidinediamine compounds and prodrugs of the invention are found in U.S. Pat. No. 5,958,935, the disclosure of which is incorporated herein by reference. Specific examples describing the synthesis of numerous 2,4-pyrimidinediamine compounds and prodrugs, as well as intermediates therefore, are described in the U.S. publication No. US2004/0029902A1, the contents of which are incorporated herein by reference. Suitable exemplary methods that can be routinely used and/or adapted to synthesize active 2,4-pyrimidinediamine compounds can also be found in WO 03/063794, U.S. application Ser. No. 10/631,029 filed Jul. 29, 2003, WO2004/014382, U.S. publication No. 2005-0234049 A1, and WO005/016893, the disclosures of which are incorporated herein by reference. All of the compounds described herein (including prodrugs) can be prepared by routine adaptation of these methods.

Exemplary synthetic methods for the 2,4-substituted pyrimidinediamines described herein are described below. Those of skill in the art will also be able to readily adapt these methods for the synthesis of specific 2,4-substituted pyrimidinediamines as described herein.

A variety of exemplary synthetic routes that can be used to synthesize the 2,4-pyrimidinediamine compounds of the invention are described in schemes below. These methods can be routinely adapted to synthesize the 2,4-pyrimidinediamine compounds and prodrugs described herein.

Synthesis of Compounds

In a certain embodiment, the compounds can be synthesized from substituted or unsubstituted uracils as illustrated in Scheme 1, below:

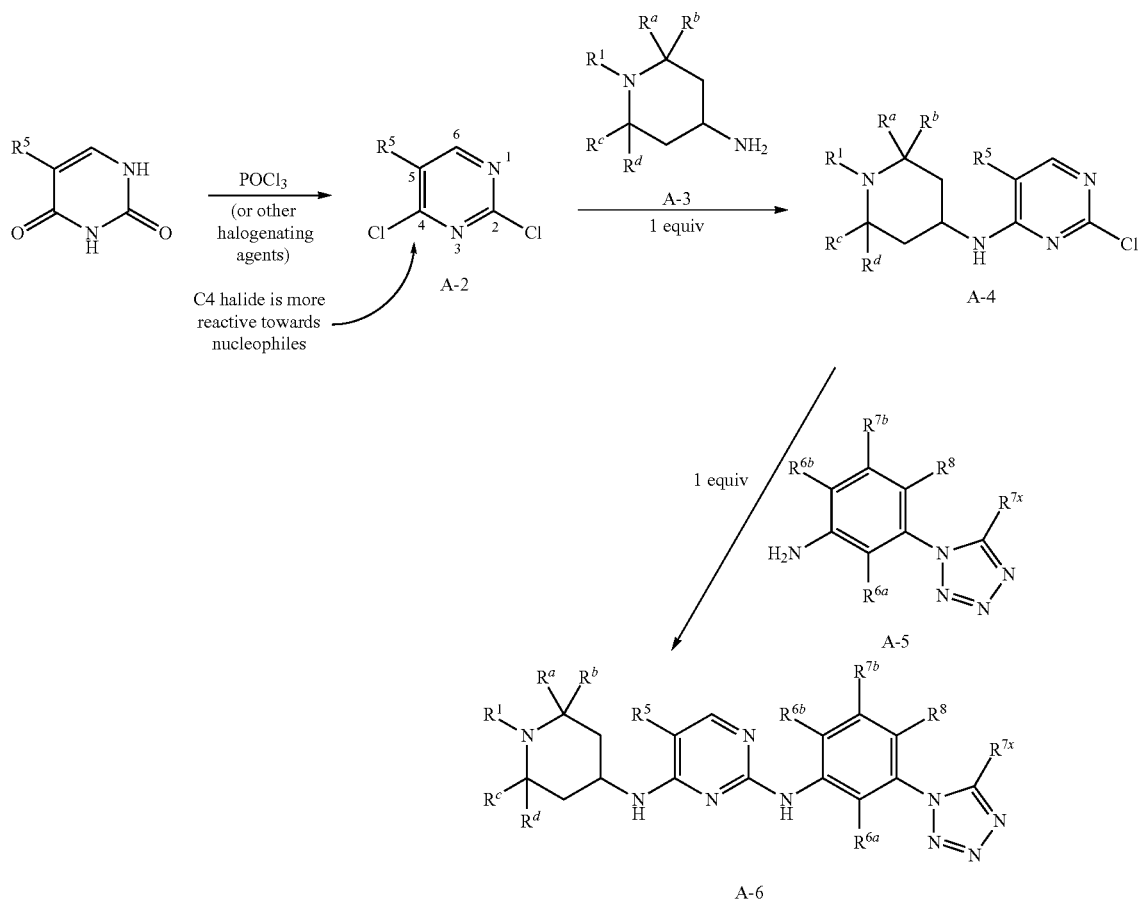

In Scheme 1, $R^1$, $R^a$, $R^b$, $R^c$, $R^d$, $R^5$, $R^{6a}$, $R^{6b}$, $R^{7b}$, $R^{7x}$, Rare as set forth hereinbefore.

According to Scheme 1, uracil A-1 is dihalogenated at the 2- and 4-positions using a standard dehydrating-halogenating agent such as $POCl_3$ (phosphorus oxychloride) (or other standard halogenating agent) under standard conditions to yield 2,4 dichloropyrimidine A-2. Depending upon the substituents in pyrimidinediamine A-2, the chloride at the C4 position is more reactive towards nucleophiles than the chloride at the C2 position. This differential reactivity can be exploited by first reacting 2,4 dichloropyrimidine A-2 with one equivalent of amine A-3, yielding 4N-substituted-2-chloro-4-pyrimidineamine A-4, followed by amine A-5 to yield a 2,4-pyrimidinediamine derivative A-6.

Typically, the C4 halide is more reactive towards nucleophiles, as illustrated in the scheme. However, as will be recognized by skilled artisans, the identity of the substituent may alter this reactivity. For example, when the substituent is trifluoromethyl, a 50:50 mixture of 4N-substituted-4-pyrimidineamine A-4 and the corresponding 2N-substituted-2-pyrimidineamine is obtained. The regioselectivity of the reaction can also be controlled by adjusting the solvent and other synthetic conditions (such as temperature), as is well-known in the art.

In a certain embodiment, to couple compounds with an electrophilic leaving group, such as halides or pseudohalides, and compounds with an amino group, nucleophilic aromatic substitution can be used. For example, a halogen substituent on Compound A-2 and the amino group on Compound A-3 can react. Also for example, a halogen substituent on Compound A-4 and the amino group on Compound A-5 can react. Conditions for nucleophilic aromatic substitution include the compounds reacting in a polar aprotic solvent or polar protic solvent. Suitable solvents include alcohols (such as isopropanol, methanol, ethanol), formic acid, dimethylsulfoxide, dimethylformamide, dioxane, and tetrahydrofuran. The reaction can be run at room temperature or can be heated.

In a certain embodiment, to couple compounds with an electrophilic leaving group, such as halides or pseudohalides, and aryl compounds with an amino group, a coupling reaction, such as a Buchwald coupling reaction, can be used. The Buchwald coupling reaction involves palladium-catalyzed synthesis of aryl amines. Starting materials are aryl halides or pseudohalides (for example, triflates) and primary or secondary amines. Such reaction can be performed using a variety of methods well known in the art and specific examples can be had by reference to the Examples hereunder described.

The reactions depicted in Scheme 1 may proceed more quickly when the reaction mixtures are heated via microwave. When heating in this fashion, the following conditions can be used: heat to 175° C. in ethanol for 5-20 min. in a Smith Reactor (Personal Chemistry, Uppsala, Sweden) in a sealed tube (at 20 bar pressure).

A specific embodiment of Scheme 1 utilizing 5-fluorouracil (Aldrich #32, 937-1) as a starting material is illustrated in Scheme 2, below.

Scheme 2

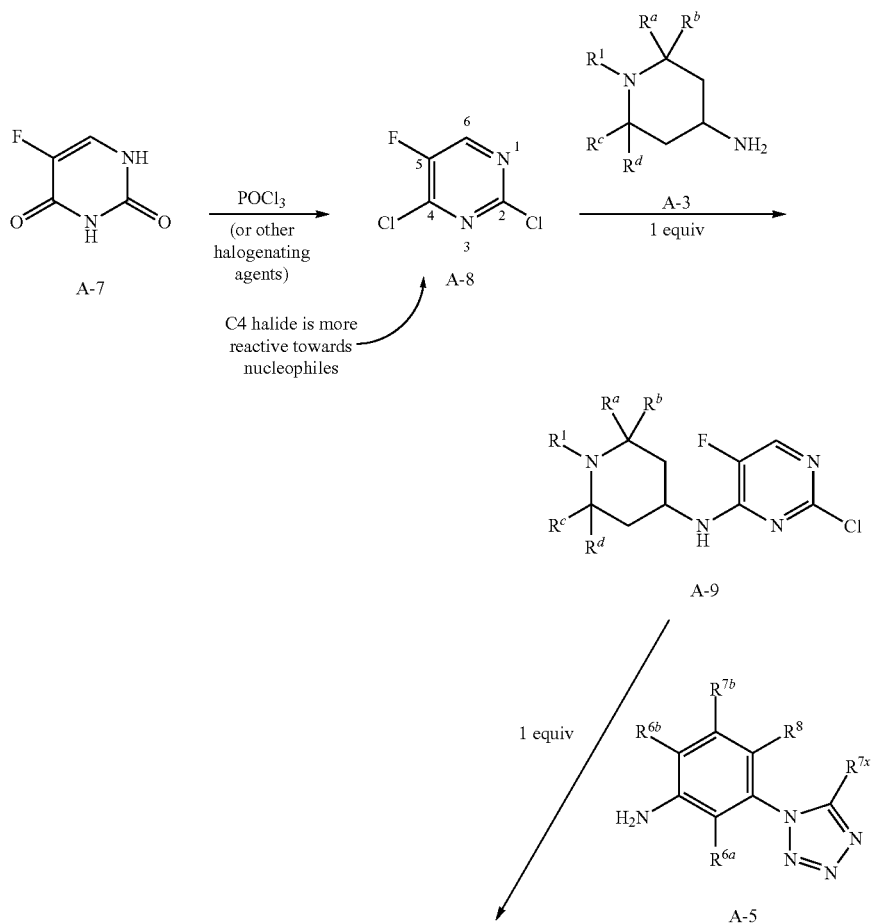

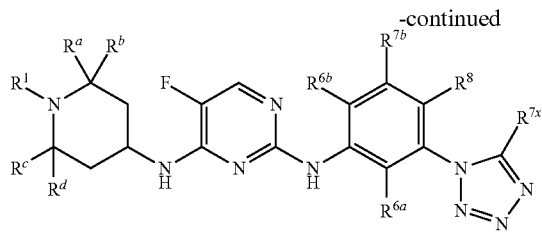

A-10

In Scheme 2, $R^1$, $R^a$, $R^b$, $R^c$, $R^d$, $R^{6a}$, $R^{6b}$, $R^{7b}$, $R^{7x}$, $R^8$ are as set forth hereinbefore.

Asymmetric 2N,4N-disubstituted-5-fluoro-2,4-pyrimidinediamine A-10 can be obtained by reacting 2,4-dichloro-5-fluoropyrimidine A-8 with one equivalent of amine A-3 (to yield 2-chloro-N4-substituted-5-fluoro-4-pyrimidineamine A-9) followed by one or more equivalents of amine A-5.

Specific embodiment of Scheme 1 to form cyano derivatives is illustrated in Scheme 3, below.

5-carbamoylpyrimidine A-12 with one equivalent of amine A-3 (to yield 2-chloro-N4-substituted-5-carbamoyl-4-pyrimidineamine A-13). The amide group of Compound A-13 is converted to a cyano group to yield Compound A-14, followed by reaction with one or more equivalents of amine A-5. Conversion of the amide group to the cyano group can be accomplished with dehydration, such as with use of Burgess reagent or trifluoroacetic anhydride.

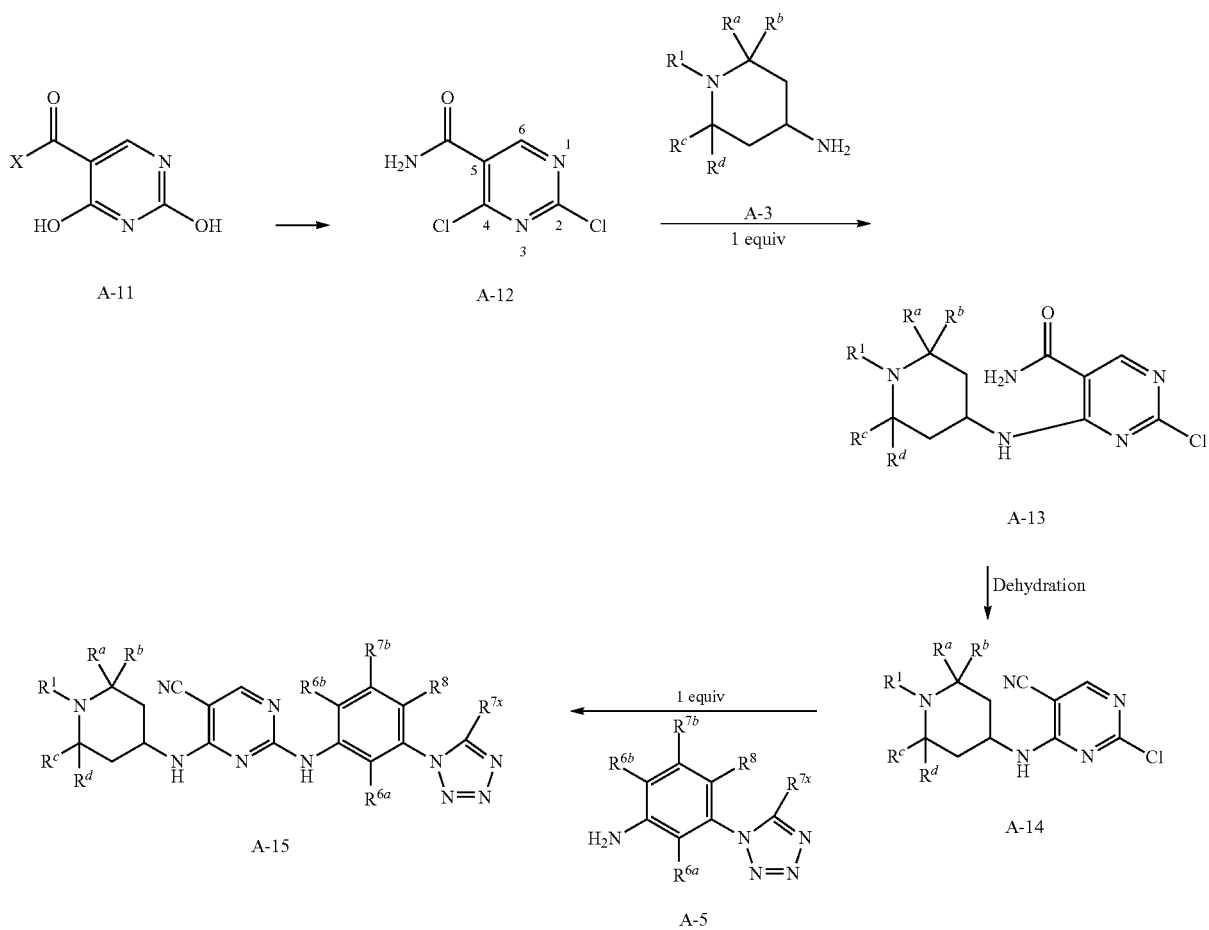

Scheme 3

In Scheme 3, $R^1$, $R^a$, $R^b$, $R^c$, $R^d$, $R^{6a}$, $R^{6b}$, $R^{7b}$, $R^{7x}$, $R^8$ are as set forth hereinbefore.

Asymmetric 2N,4N-disubstituted-5-cyano-2,4-pyrimidinediamine A-15 can be obtained by reacting 2,4-dichloro- Uracil Starting Materials and Intermediates The uracil A-1, A-7, and A-11 starting materials can be purchased from commercial sources or prepared using standard techniques of organic chemistry. Commercially available uracils that can be used as starting materials in the schemes disclosed herein include, by way of example and not limitation, uracil (Aldrich #13,078-8; CAS Registry 66-22-8); 5 bromouracil (Aldrich #85, 247-3; CAS Registry 51-20-7; 5 fluorouracil (Aldrich #85, 847-1; CAS Registry 51-21-8); 5 iodouracil (Aldrich #85, 785-8; CAS Registry 696-07-1); 5 nitrouracil (Aldrich #85, 276-7; CAS Registry 611-08-5); 5 (trifluoromethyl)-uracil (Aldrich #22, 327-1; CAS Registry 54-20-6). Additional 5-substituted uracils are available from General Intermediates of Canada, Inc., Edmonton, Calif. and/or Interchim, Cedex, France, or can be prepared using standard techniques. Myriad textbook references teaching suitable synthetic methods are provided infra.

Amino Starting Materials and Intermediates

Amines, such as A-3 and A-5 can be purchased from commercial sources or, alternatively, can be synthesized utilizing standard techniques. For example, suitable amines can be synthesized from nitro precursors using standard chemistry. See also Vogel, 1989, Practical Organic Chemistry, Addison Wesley Longman, Ltd. and John Wiley & Sons, Inc.

Tetrazole Intermediates

Compound A-5 with an N-linked tetrazole in Schemes 1-3 was prepared as illustrated in Scheme 4 and may be incorporated into the present compounds according to the procedure illustrated in Scheme 4.

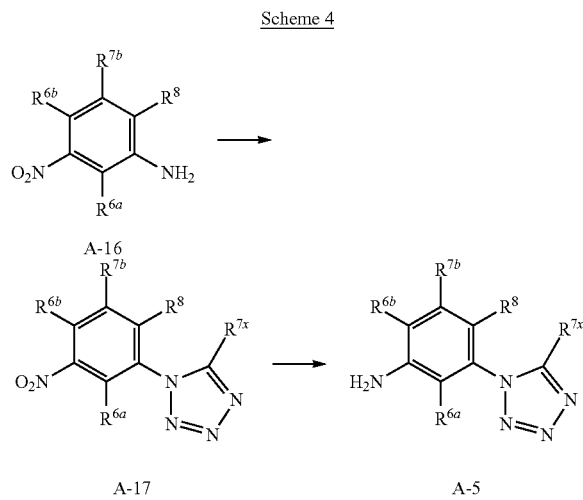

In Scheme 4, $R^{6a}$, $R^{6b}$, $R^{7b}$, $R^8$, and $R^{7x}$ are as previously defined.

To prepare Compound A-5, Compound A-16 was reacted to form tetrazole Compound A-17 by treatment with sodium azide and trimethyl orthoformate or triethyl orthoformate. The reaction is general to any appropriate aminophenyl compound. Compound A-17 was reacted to reduce the nitro group to form Compound A-5. Compound A-5 can also be prepared according to the procedures provided by Satoh et al., Tetrahedron Lett, 1995, 36, 1749; Gupta et al. Tetrahedron Lett, 2004, 45, 4113; Su et al. Eur. J. Org. Chem., 2006, 2723; and Potewar et al., Tetrahedron Lett, 2007, 48, 172.

Substitution of the ring with substituents can be performed with standard chemistry. In certain embodiment, substitution of the ring with substituents can be performed with nucleophilic aromatic substitution. For example, a halogen substituent can be replaced with another substituent with nucleophilic aromatic substitution. In certain embodiment, substitution of the ring with substituents can be performed with a metal catalyzed coupling reaction. For example, a halogen substituent can be replaced with another substituent with utilization of a metal catalyst. Suitable metal catalyzed reactions to place appropriate substituents include Suzuki coupling, Stille coupling, and Buchwald coupling.

The nitro group of Compound A-17 was converted to an amino group to produce Compound A-5. The conversion of the nitro group to an amino group can be accomplished by various methods. A suitable method for reduction of nitro group is catalytic hydrogenation which uses hydrogen and a catalyst, such as, but not limited to, palladium on carbon, platinum oxide, Raney nickel, and samarium diiodide.

Compound A-16 can be purchased from commercial sources or prepared using standard techniques of organic chemistry. For example, Compound A-16 can be prepared from the corresponding amine with standard techniques of organic chemistry. In certain embodiment, Compound A-16 can be prepared from the corresponding dinitro compound in which one of the nitro groups is reduced to an amino group. Myriad textbook references teaching suitable synthetic methods are provided infra.

Although many of the synthetic schemes discussed above do not illustrate the use of protecting groups, skilled artisans will recognize that in some instances certain substituents may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups, their attachment and removal suitable for a particular application can be found, for example, in Greene & Wuts, supra.

Prodrugs as described herein can be prepared by routine modification of the above-described methods. Alternatively, such prodrugs can be prepared by reacting a suitably protected 2,4-pyrimidinediamine with a suitable progroup. Conditions for carrying out such reactions and for deprotecting the product to yield prodrugs as described herein are well-known.

Myriad references teaching methods useful for synthesizing pyrimidines generally, as well as starting materials described in Schemes (I)-(VII), are known in the art. For specific guidance, the reader is referred to Brown, D. J., "The Pyrimidines", in The Chemistry of Heterocyclic Compounds, Volume 16 (Weissberger, A., Ed.), 1962, Interscience Publishers, (A Division of John Wiley & Sons), New York ("Brown I"); Brown, D. J., "The Pyrimidines", in The Chemistry of Heterocyclic Compounds, Volume 16, Supplement I (Weissberger, A. and Taylor, E. C., Ed.), 1970, Wiley-Interscience, (A Division of John Wiley & Sons), New York (Brown II"); Brown, D. J., "The Pyrimidines", in The Chemistry of Heterocyclic Compounds, Volume 16, Supplement II (Weissberger, A. and Taylor, E. C., Ed.), 1985, An Interscience Publication (John Wiley & Sons), New York ("Brown III"); Brown, D. J., "The Pyrimidines" in The Chemistry of Heterocyclic Compounds, Volume 52 (Weissberger, A. and Taylor, E. C., Ed.), 1994, John Wiley & Sons, Inc., New York, pp. 1-1509 (Brown IV"); Kenner, G. W. and Todd, A., in Heterocyclic Compounds, Volume 6, (Elderfield, R. C., Ed.), 1957, John Wiley, New York, Chapter 7 (pyrimidines); Paquette, L. A., Principles of Modern Heterocyclic Chemistry, 1968, W. A. Benjamin, Inc., New York, pp. 1-401 (uracil synthesis pp. 313, 315; pyrimidinediamine synthesis pp. 313-316; amino pyrimidinediamine synthesis pp. 315); Joule, J. A., Mills, K. and Smith, G. F., Heterocyclic Chemistry, 3rd Edition, 1995, Chapman and Hall, London, UK, pp. 1-516; Vorbrüggen, H. and Ruh-Pohlenz, C., Handbook of Nucleoside Synthesis, John Wiley & Sons, New York, 2001, pp. 1-631 (protection of pyrimidines by acylation pp. 90-91; sylation of pyrimidines pp. 91-93); Joule, J. A., Mills, K. and Smith, G. F., Heterocyclic Chemistry, 4th Edition, 2000, Blackwell Science, Ltd, Oxford, UK, pp. 1-589; and Comprehensive Organic Synthesis, Volumes 1-9 (Trost, B. M. and Fleming, I., Ed.), 1991, Pergamon Press, Oxford, UK.

Pharmaceutical Compositions

The disclosed compounds are useful, at least, for the inhibition of PKC activity and the treatment of a disease or disorder that is mediated through the activity of a PKC activity. Accordingly, pharmaceutical compositions comprising at least one disclosed compound are also described herein.

A pharmaceutical composition comprising a subject compound may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A subject compound may be administered to the host using any convenient means capable of resulting in the desired reduction in disease condition or symptom. Thus, a subject compound can be incorporated into a variety of formulations for therapeutic administration. More particularly, a subject compound can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Formulations for pharmaceutical compositions are well known in the art. For example, Remington's Pharmaceutical Sciences, by E. W. Martin, Mack Publishing Co., Easton, Pa., 19th Edition, 1995, describes exemplary formulations (and components thereof) suitable for pharmaceutical delivery of disclosed compounds. Pharmaceutical compositions comprising at least one of the subject compounds can be formulated for use in human or veterinary medicine. Particular formulations of a disclosed pharmaceutical composition may depend, for example, on the mode of administration and/or on the location of the infection to be treated. In some embodiments, formulations include a pharmaceutically acceptable carrier in addition to at least one active ingredient, such as a subject compound. In other embodiments, other medicinal or pharmaceutical agents, for example, with similar, related or complementary effects on the affliction being treated can also be included as active ingredients in a pharmaceutical composition.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The disclosed pharmaceutical compositions may be formulated as a pharmaceutically acceptable salt of a disclosed compound. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydroiodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Lists of other suitable pharmaceutically acceptable salts are found in Remington's Pharmaceutical Sciences, 17th Edition, Mack Publishing Company, Easton, Pa., 1985. A pharmaceutically acceptable salt may also serve to adjust the osmotic pressure of the composition.

A subject compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The preparation may also be emulsified or the active ingredient encapsulated in liposome vehicles. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

In some embodiments, a subject compound can be delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

A subject compound can be utilized in aerosol formulation to be administered via inhalation. A subject compound can be formulated into pressurized acceptable propellants such as dichlorodifluoromethane, propane, nitrogen and the like.

Furthermore, a subject compound can be made into suppositories by mixing with a variety of bases such as emulsifying bases or water-soluble bases. A subject compound can be administered rectally via a suppository. The suppository can include vehicles such as cocoa butter, carbowaxes and polyethylene glycols, which melt at body temperature, yet are solidified at room temperature.

The term "unit dosage form," as used herein, refers to physically discrete units suitable as unitary dosages for human and animal subjects, each unit containing a predetermined quantity of a subject compound calculated in an amount sufficient to produce the desired effect in association with a pharmaceutically acceptable diluent, carrier or vehicle. The specifications for a subject compound depend on the particular compound employed and the effect to be achieved, and the pharmacodynamics associated with each compound in the host.

The dosage form of a disclosed pharmaceutical composition will be determined by the mode of administration chosen. For example, in addition to injectable fluids, topical or oral dosage forms may be employed. Topical preparations may include eye drops, ointments, sprays and the like. Oral formulations may be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions comprising a subject compound may be formulated in unit dosage form suitable for individual administration of precise dosages. The amount of active ingredient administered will depend on the subject being treated, the severity of the affliction, and the manner of administration, and is known to those skilled in the art. Within these bounds, the formulation to be administered will contain a quantity of the extracts or compounds disclosed herein in an amount effective to achieve the desired effect in the subject being treated.

Each therapeutic compound can independently be in any dosage form, such as those described herein, and can also be administered in various ways, as described herein. For example, the compounds may be formulated together, in a single dosage unit (that is, combined together in one form such as capsule, tablet, powder, or liquid, etc.) as a combination product. Alternatively, when not formulated together in a single dosage unit, an individual subject compound may be administered at the same time as another therapeutic compound or sequentially, in any order thereof.

Methods of Administration

The subject compounds can inhibit a protein kinase C activity. Accordingly, the subject compounds are useful for treating a disease or disorder that is mediated through the activity of a PKC activity in a subject. Accordingly, the subject compounds are useful for treating a disease or disorder that is associated with the activation of T-cells in a subject.

The route of administration will be selected according to a variety of factors including, but not necessarily limited to, the condition to be treated, the formulation and/or device used, the patient to be treated, and the like. Routes of administration useful in the disclosed methods include but are not limited to oral and parenteral routes, such as intravenous (iv), intraperitoneal (ip), rectal, topical, ophthalmic, nasal, and transdermal. Formulations for these dosage forms are described herein.

An effective amount of a subject compound will depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (host) being treated. For example, this may be the amount of a subject compound necessary to prevent, inhibit, reduce or relieve a disease or disorder that is mediated through the activity of a PKC activity in a subject. Ideally, a therapeutically effective amount of a compound is an amount sufficient to prevent, inhibit, reduce or relieve a disease or disorder that is mediated through the activity of a PKC activity in a subject without causing a substantial cytotoxic effect on host cells.

Therapeutically effective doses (or growth inhibitory amounts) of a subject compound or pharmaceutical composition can be determined by one of skill in the art, with a goal of achieving local (e.g., tissue) concentrations that are at least as high as the $IC_{50}$ of an applicable compound disclosed herein.

An example of a dosage range is from about 0.1 to about 200 mg/kg body weight orally in single or divided doses. In particular examples, a dosage range is from about 1.0 to about 100 mg/kg body weight orally in single or divided doses, including from about 1.0 to about 50 mg/kg body weight, from about 1.0 to about 25 mg/kg body weight, from about 1.0 to about 10 mg/kg body weight (assuming an average body weight of approximately 70 kg; values adjusted accordingly for persons weighing more or less than average). For oral administration, the compositions are, for example, provided in the form of a tablet containing from about 50 to about 1000 mg of the active ingredient, particularly about 75 mg, about 100 mg, about 200 mg, about 400 mg, about 500 mg, about 600 mg, about 750 mg, or about 1000 mg of the active ingredient for the symptomatic adjustment of the dosage to the subject being treated. In one exemplary oral dosage regimen, a tablet containing from about 500 mg to about 1000 mg active ingredient is administered once (e.g., a loading dose) followed by administration of ½ dosage tablets (e.g., from about 250 to about 500 mg) each 6 to 24 hours for at least 3 days.

The specific dose level and frequency of dosage for any particular subject may be varied and will depend upon a variety of factors, including the activity of the subject compound, the metabolic stability and length of action of that compound, the age, body weight, general health, sex and diet of the subject, mode and time of administration, rate of excretion, drug combination, and severity of the condition of the host undergoing therapy.

The present disclosure also contemplates combinations of one or more disclosed compounds with one or more other agents or therapies useful in the treatment of a disease or disorder. In certain instances, the disease or disorder is mediated through the activity of a PKC activity in a subject. In certain instances, the disease or disorder is cell proliferative disorder. For example, one or more disclosed compounds may be administered in combination with effective doses of other medicinal and pharmaceutical agents, or in combination other non-medicinal therapies, such as hormone or radiation therapy. The term "administration in combination with" refers to both concurrent and sequential administration of the active agents.

Protein Kinase C

Protein Kinase C

PKC is a family of enzymes that function as serine/threonine kinases. The isoenzymes of PKC differ in their tissue distribution, enzymatic selectivity, requirement for $Ca^{2+}$, and regulation. PKCs play an important role in cell-cell signaling, gene expression and in the control of cell differentiation and growth.

The subject compound can be a selective inhibitor of PKC, e.g. an inhibitor selective for PKC over one or more other protein kinases, e.g. over one or more tyrosine kinases, for instance, over one or more non-receptor or receptor tyrosine kinases, e.g. over one or more of PKA, PKB, Abl Met, Src, Ins-R, Flt-3, JAK-2, KDR and/or Ret proteins. The selective PKC inhibitors may optionally be selective over one or more serine/threonine kinases, e.g. one or more serine/threonine kinases which do not belong to the CDK family. The subject compounds can exhibit a selectivity of at least 10 fold, or 20 fold, or 100 fold for the PKC over one or more other protein kinases, e.g. over one or more tyrosine kinases, e.g. over Flt-3, JAK-2, KDR and/or Ret proteins, or over one or more serine/threonine kinases which do not belong to the CDK family.

The selectivity of a selective inhibitor of PKC over other protein kinases may be calculated as the ratio of the $IC_{50}$ measured for PKC in an assay described herein over the $IC_{50}$ determined for another kinase. In a certain instance, there is provided a PKC inhibitor for which the ratio of the $IC_{50}$ value as determined in an Allogeneic Mixed Lymphocyte Reaction (MLR) assay to the $IC_{50}$ value as determined in a BM assay is higher than 5, 10, 20, or 30. MLR and BM assays can be done according to known methods, e.g. mouse or human MLR and BM assays, such as disclosed herein.

The disclosure provides an inhibitor of PKC, which can be an isozyme-selective PKC inhibitor, wherein the subject compound possesses selectivity for the isoforms θ and α of PKC over one or more of the other PKC isoforms. In a certain instance, the subject compound possesses selectivity for the isoform θ of PKC over one or more of the other PKC isoforms. In a certain instance, the subject compound possesses selectivity for the isoform a of PKC over one or more of the other PKC isoforms. In one embodiment, the disclosed compounds exhibit selectivity for PKC θ and PKC α over at least one PKC isoform.

A subject compound can show a selectivity of at least 10 fold, or 20 fold, or 100 fold for the isoforms θ or α of PKC over one or more of the other PKC isoforms. Selectivity for the isoforms θ or α of PKC over one or more of the other PKC isoforms can be measured by comparing the $IC_{50}$ of the subject compound for the isoforms θ or α of PKC to the $IC_{50}$ of the subject compound for the other PKC isoforms. In a certain instance, the selectivity can be determined by calculating the ratio of $IC_{50}$ of the subject compound for the other isoforms of PKC to the $IC_{50}$ of the subject compound for θ or α isoforms of PKC. In certain examples subject compounds exhibit a selectivity for PKC θ, α or both over another PKC isoform of at least about 2-fold, such as from about 3-fold to about 300-fold, from about 10-fold to about 100-fold or from about 5-fold to 50-fold. $IC_{50}$ values are obtained, for example, according to PKC assays described herein. The subject compounds can show an $IC_{50}$ value for the isoforms θ or α of PKC of 1 μM or less, such as less than about 300 nM, such as from about 1 nM to about 250 nM, less than 100 nM or even less than 10 nM in the assays disclosed herein.

The subject compounds can show a selectivity of the isoforms θ or μ of PKC over other isoforms of PKC, as well as a selectivity over one or more of the other protein kinases, e.g. over one or more tyrosine kinases, or over one or more serine/threonine kinases which do not belong to the CDK-family, e.g. over one or more of PKA, PKB, Abl, Met, Src, Ins-it, Flt-3, JAK-2, KDR and Ret proteins, e.g. over one or more of Flt-3, JAK-2, KDR and Ret proteins.

Certain isozymes of PKC have been implicated in the mechanisms of various disease states, including, but not necessarily limited to, the following: cancer (PKC α, βI, βII, and δ); cardiac hypertrophy and heart failure (PKC βI and PKC βII) nociception (PKC γ and ε); ischemia including myocardial infarction (PKC ε and δ); immune response, particularly T-cell mediated (PKC θ and α); and fibroblast growth and memory (PKC δ and ζ). The role of PKC ε is also implicated in pain perception. PKC inhibitors can also be used for treating an ocular disease or disorder involving inflammatory and/or neovascular events.

The subject compounds can be used in the treatment of mammalian (especially human) disease states characterized by aberrant, elevated activity of a PKC isozyme in a tissue as compared to non-disease tissue of the same origin. PKC isozymes and disease states and/or biological functions amenable to therapy by inhibition of activity of the PKC isozyme include, but are not necessarily limited to: PKC α (hyperproliferative cellular diseases, such as cancer); PKC βI and PKC βII (cardiac hypertrophy and heart failure); PKC γ (pain management); PKC δ (ischemia, hypoxia (e.g., such as in myocardial infarction and in stroke); apoptosis induced by UV irradiation; and aberrant fibroblast growth (e.g., as may occur in wound healing)); PKC ε (pain management, myocardial dysfunction); PKC θ (immune system diseases, particularly those involving T-cell mediated responses); and PKC ζ (memory and fibroblast growth).

PKC Theta

PKC θ is expressed predominantly in lymphoid tissue and skeletal muscle. PKC θ is selectively expressed in T-cells and plays a role in mature T-cell activation. It has been shown that PKC θ is involved in T-cell receptor (TCR)-mediated T-cell activation but inessential during TCR-dependent thymocyte development. PKC θ, but not other PKC isoforms, translocates to the site of cell contact between antigen-specific T-cells and antigen presenting cells (APC), where it localizes with the TCR in the central core of the T-cell activation. PKC θ, but not the α, ε, or ζ isoenzymes, can selectively activate a FasL promoter-reporter gene and upregulate the mRNA or cell surface expression of endogenous FasL. On the other hand, PKC θ and ε can promote T-cell survival by protecting the cells from Fas-induced apoptosis, and this protective effect was mediated by promoting p90Rsk-dependent phosphorylation of BCL-2 family member BAD. Thus, PKC θ appears to play a dual regulatory role in T-cell apoptosis.

PKC θ inhibitors can find use in the treatment or prevention of disorders or diseases mediated by T lymphocytes, for example, autoimmune disease such as rheumatoid arthritis, psoriasis and lupus erythematosus, and inflammatory disease such as asthma and inflammatory bowel diseases.

PKC θ is a drug target for immunosuppression in transplantation and autoimmune diseases (Isakov et al. (2002) Annual Review of Immunology, 20, 761-794). PCT Publication WO2004/043386 identifies PKC θ as a target for treatment of transplant rejection and multiple sclerosis. PKC θ also plays a role in inflammatory bowel disease (The Journal of Pharmacology and Experimental Therapeutics (2005), 313

(3), 962-982), asthma (WO 2005062918), and lupus (Current Drug Targets: Inflammation & Allergy (2005), 4 (3), 295-298).

In addition, PKC θ is highly expressed in gastrointestinal stromal tumors (Blay, P. et al. (2004) Clinical Cancer Research, 10, 12, Pt. 1), it has been suggested that PKC θ is a molecular target for treatment of gastrointestinal cancer (Wiedmann, M. et al. (2005) Current Cancer Drug Targets 5(3), 171).

Experiments induced in PKC θ knock-out mice led to the conclusion that PKC θ inactivation prevented fat-induced defects in insulin signalling and glucose transport in skeletal muscle (Kim J. et al, 2004, The J. of Clinical Investigation 114 (6), 823). This data indicates PKC θ is a therapeutic target for the treatment of type 2 diabetes, and hence PKC θ inhibitors can be useful for treating such disease.

Therapeutic Applications

The subject compounds are useful for treating a disease or disorder that is mediated through, or exacerbated by, the activity of a PKC in a subject in need of treatment. Also, the compounds are useful for treating a disease or disorder that is associated with aberrant or otherwise undesirable T cell activation in a subject.

Accordingly, the present disclosure provides methods of treating an inflammatory disease in a subject by administering an effective amount of a subject compound, including a salt or solvate or stereoisomer thereof, so as to treat inflammation. Inflammatory diseases contemplated for therapy include acute and chronic inflammation mediated or exacerbated by PKC activity The present disclosure also provides methods of treating an autoimmune disease in a subject by administering to the subject an effective amount of a subject compound, including a salt or solvate or stereoisomer thereof, so as to treat the autoimmune disease.

The present disclosure also provides methods of treating an ocular disease or disorder involving inflammatory and/or neovascular events by administration of a subject compound, including a salt or solvate or stereoisomer thereof, in an effective amount.

Diseases or conditions of interest for treatment according to the present disclosure include, but are not limited to, atherosclerosis, vascular occlusion due to vascular injury such as angioplasty, restenosis, obesity, syndrome X, impaired glucose tolerance, polycystic ovary syndrome, hypertension, heart failure, chronic obstructive pulmonary disease, CNS diseases such as Alzheimer disease or amyotrophic lateral sclerosis, cancer, infectious diseases such as: AIDS, septic shock or adult respiratory distress syndrome, ischemia/reperfusion injury, e.g.: myocardial infarction, stroke, gut ischemia, renal failure or hemorrhage shock, and traumatic shock, e.g. traumatic brain injury.

Further diseases or conditions of interest for treatment according to the present disclosure include, but are not limited to, T-cell mediated acute or chronic inflammatory diseases or disorders or autoimmune diseases, rheumatoid arthritis, osteoarthritis, systemic lupus erythematosus, Hashimoto's thyroiditis, multiple sclerosis, myasthenia gravis, diabetes type I or II and the disorders associated therewith, transplant rejection, graft versus host disease, respiratory diseases, asthma, inflammatory lung injury, inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases (such as Sjoegren's syndrome, keratoconjunctivitis, uveitis) inflammatory bowel disease, Crohn's disease or ulcerative colitis, Guillain-Barre syndrome, and allergies.

The subject compounds can also be used for preventing or treating or delaying ocular diseases and disorders involving inflammation and/or neovascularization. Ocular diseases or disorders involving inflammatory and/or neovascular events include, but are not limited to, macular degeneration (AMD), diabetic ocular diseases or disorders, uveitis, optic neuritis, ocular edema, ocular angiogenesis, ischemic retinopathy, anterior ischemic optic neuropathy, optic neuropathy and neuritis, macular edema, cystoid macular edema (CME), retinal disease or disorder, such as retinal detachment, retinitis pigmentosa (RP), Stargart's disease, Best's vitelliform retinal degeneration, Leber's congenital amaurosis and other hereditary retinal degenerations, Sorsby's fundus dystrophy, pathologic myopia, retinopathy of prematurity (ROP), Leber's hereditary optic neuropathy, corneal transplantation or refractive corneal surgery, keratoconjunctivitis, or dry eye.

Generally, cell proliferative disorders treatable with the subject compound disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, breast cancer, ovarian cancer, renal cancer, gastrointestinal cancer, kidney cancer, bladder cancer, pancreatic cancer, lung squamous carcinoma, and adenocarcinoma.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, Blood 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34;22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, Blood 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., Proc. Natl. Acad. Sci. USA, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplamacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9;22)(qq34;q11)), chronic neutrophilic leukemia, chronic eosinophilic leukemiahypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome with t(9;12) (q22;p12) (TEL-Syk fusion; see, e.g., Kuno et al., 2001, Blood 97:1050).

In some embodiments, the composition can be used to treat acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21)(q22;q22), AML1 (CBF-alpha)/ETO, Acute promyelocytic leukemia (AML with t(15;17)(q22;q11-12) and variants, PML/RAR-alpha), AML with abnormal bone marrow eosinophils (inv(16) (p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

In other aspects, cell proliferative disorders comprise virally mediated tumors. These can arise from infection of cells by an oncogenic virus that has the capability of transforming a normal cell into a tumor cell. Because rates of viral infection far exceed the number of actual incidence of cell transformation, viral mediated transformation generally act together with other cellular factors to generate a transformed tumor cell. Thus, a virally mediated tumor does not require the virus to be the sole causative agent of the cell proliferative disorder, but rather that the viral infection or persistent presence of virus is associated with the generation of the tumor. Generally, tumors where the causative agent is a virus typically has continual expression of a limited number of viral genes and that viral these oncogenes, expressed as part of the viral infection or through persistence of the virus, disrupts the normal cellular gene expression and signal transduction pathways. Without being bound by theory, viral oncogenes involved in cell transformation appear to disrupt four main cellular processes: cell surface receptors that interact with growth factors and extracellular matrix, transmembrane signaling networks, cytosolic elements such as soluble proteins and second messengers, and nuclear proteins including DNA binding proteins and factors which function directly and indirectly in gene regulation and replication.

Characterization of Functional Properties

The following are exemplary assays useful in characterizing activities of a compound of interest.

A. In Vitro

1. Protein Kinase C Assay

The inhibition of PKC activity was measured by monitoring the production of phosphorylated peptide by fluorescence polarization at different concentrations of the inhibitor. Reactions were carried out in 96-well plate format with a total volume of 20 μL containing 20 mM HEPES, pH 7.4, 5 mM $MgCl_2$, 0.2 mM $CaCl_2$, 1 mM DTT, 0.02% Brij-35, 0.1 mg/mL phosphatidylserine, 0.02 mg/mL dioleoyl-sn-glycerol and 5 μM each of ATP and the peptide substrate. Compounds were first diluted serially in DMSO and then transferred to a solution containing the above concentrations of HEPES, $MgCl_2$, $CaCl_2$, DTT, and Brij-35 to yield 5× compound solutions in 2% DMSO, which was then added to the reaction solution. Reactions were initiated by the addition of PKC at a typical concentration as described in the table below, and then allowed to incubate at room temperature for 20 minutes. At the end of this time, a combination of quench (EDTA) and detection (peptide tracer and antibody) reagents was added using the protocol of Invitrogen P2748 (Carlsbad, Calif.), a Protein Kinase C Fluorescence polarization Assay Kit. After a 30 minute period of incubation, the amount of phosphorylated peptide generated was measured by fluorescence polarization (Ex=485 nm, Em=535 nm) using a Tecan Polarian instrument (Switzerland).

ture (25 μl) contains 1.5 μM of a tridecapeptide acceptor substrate that mimics the pseudo substrate sequence of PKC α with the Ala→Ser replacement, 10 μM $^{33}$P-ATP, 10 mM $Mg(NO_3)_2$, 0.2 mM $CaCl_2$, PKG at a protein concentration varying from 25 to 400 ng/ml (depending on the isotype used), lipid vesicles (containing 30 mol % phosphatidylserine, 5 mol % DAG and 65 mol % phosphatidylcholine) at a final lipid concentration of 0.5 mM, in 20 mM Tris-HCl buffer pH 7.4+0.1% BSA. Incubation is performed for 60 minutes at room temperature. Reaction is stopped by adding 50 μl of stop mix (100 mM EDTA, 200 μM ATP, 0.1% Triton X-100, 0.375 mg/well streptavidin-coated SPA beads in phosphate buffered saline w/o Ca, Mg. After 10 minutes incubation at room temperature, the suspension is spun down for 10 minutes at 300 g. Incorporated radioactivity is measured in a Trilux counter for 1 minute. $IC_{50}$ measurement is performed on a routine basis by incubating a serial dilution of

TABLE 2

|  | Peptide substrate | SEQ ID | Enzyme source | enzyme concentration |
|---|---|---|---|---|
| PKC theta | RFARKGSLRQKNV | Seq ID No. 1 | Upstate Biotechnologies, Temecula, CA, cat. #14-444 | 40 ng/mL |
| PKC epsilon | RFARKGSLRQKNV | Seq ID No. 1 | Upstate Biotechnologies, Temecula, CA, cat. #14-518 | 50 ng/mL |

2. IL-2 ELISA, Human Primary T Cell, Anti-CD3+ CD28+ Assays

Human Primary T Cell Isolation and Culture:

Human primary T cells were prepared as follows. Fresh PBMC's from All Cells (Cat #PB002) were re-suspended in RPMI (RPMI-1640 with L-Glutamine; Mediatech, Inc., Herndon Va., cat. #10-040-CM) with 10% FBS and seeded into flasks and incubated at 37° C. for 2 hours to allow the monocytes to adhere. The non-adherent cells were then centrifuged and re-suspended in RPMI medium containing 40 U/ml IL2 and seeded into a flask pre-coated with 1 μg/ml aCD3 and 5 ug/ml aCD28 (Anti-Human CD3, BD Pharmingen Catalog #555336, Anti-Human CD28, Beckman Coulter Catalog #IM1376). The cells were stimulated for 3-4 days, then transferred to a fresh flask and maintained in RPMI (RPMI-1640 with L-Glutamine; Mediatech, Inc., Herndon Va., cat. #10-040-CM) with 10% FBS and 40 U/mL IL-2.

Primary T Cell Stimulation and IL2 ELISA:

Human primary T cells (100,000 cells per well) were pre-incubated with or without test compound in RPMI-1640 with L-Glutamine and 10% FBS for 1 hr at 37° C. Cells were then stimulated by transferring them to round-bottom 96-well plates pre-coated with 1 μg/ml aCD3 and 5 μg/ml aCD28. For counter assay, cells were instead stimulated by adding 8× stock solutions of PMA and ionomycin in RPMI-1640 with L-Glutamine and 10% FBS (for final concentrations of 0.5 ng/ml PMA and 0.1 μM ionomycin, both from Calbiochem). Cells were incubated at 37° C. for 24 hours before 100 μL supernatants were harvested for quantification of IL-2 by ELISA using Human IL-2 Duoset ELISA Kit from R and D Systems, Cat. #DY202E.

3. Protein Kinase C Assay

The subject compounds can be tested for activity on different PKC isoforms according to the following method. Assay is performed in a white with clear bottom 384-well microtiterplate with non-binding surface. The reaction mixture inhibitor at concentrations ranging between 1-1000 μM. $IC_{50}$ values are calculated from the graph by curve fitting with XL Fit® software.

4. Protein Kinase C α Assay

Human recombinant PKC α is obtained from Oxford Biomedical Research and is used under the assay conditions as described under Section A.1 above.

5. Protein Kinase C β1 Assay

Human recombinant PKC β1 is obtained from Oxford Biomedical Research and is used under the assay conditions as described under Section A.1 above.

6. Protein Kinase C δ Assay

Human recombinant PKC δ is obtained from Oxford Biomedical Research and is used under the assay conditions as described under Section A.1 above.

7. Protein Kinase C ε Assay

Human recombinant PKC ε is obtained from Oxford Biomedical Research and is used under the assay conditions as described under Section A.1 above.

8. Protein Kinase C η Assay

Human recombinant PKC η is obtained from PanVera and is used under the assay conditions as described under Section A.1 above.

9. Protein Kinase C θ Assay

Human recombinant PKC θ is used under the assay conditions as described above.

10. CD28 Costimulation Assay

The assay is performed with Jurkat cells transfected with a human interleukin-2 promoter/reporter gene construct as described by Baumann G et al. in Transplant. Proc. 1992; 24:43-8, the β-galactosidase reporter gene being replaced by the luciferase gene (de Wet J., et al., Mol. Cell. Biol. 1987, 7(2), 725-737). Cells are stimulated by solid phase-coupled antibodies or phorbol myristate acetate (PMA) and the $Ca^{++}$ ionophore ionomycin as follows. For antibody-mediated stimulation Microlite TM1 microtiter plates (Dynatech) are coated with 3 μg/ml goat anti-mouse IgG Fc antibodies (Jackson) in 55 µl phosphate-buffered saline (PBS) per well for three hours at room temperature. Plates are blocked after removing the antibodies by incubation with 2% bovine serum albumin (BSA) in PBS (300 µl per well) for 2 hours at room temperature. After washing three times with 300 µl PBS per well, 10 ng/ml anti-T cell receptor antibodies (WT31, Becton & Dickinson) and 300 ng/ml anti-CD28 antibodies (15E8) in 50 µl 2% BSA/PBS are added as stimulating antibodies and incubated overnight at 4° C. Finally the plates are washed three times with 300 µl PBS per well. Seven three-fold serial dilutions of test compounds in duplicates in assay medium (RPMI 1640/10% fetal calf serum (FCS) containing 50 µM 2-mercaptoethanol, 100 units/ml penicillin and 100 µg/ml streptomycin) are prepared in separate plates, mixed with transfected Jurkat cells (clone K22 290_H23) and incubated for 30 minutes at 37° C. in 5% $CO_2$ 100 µl of this mixture containing $1 \times 10^5$ cells are then transferred to the antibody-coated assay plates. In parallel 100 µl are incubated with 40 ng/ml PMA and 2 µM ionomycin. After incubation for 5.5 hours at 37° C. in 5% $CO_2$, the level of luciferase is determined by bioluminescence measurement. The plates are centrifuged for 10 minutes at 500 g and the supernatant is removed by flicking. Lysis buffer containing 25 mM Tris-phosphate, pH 7.8, 2 mM DTT, 2 mM 1,2-diaminocyclohexane-N,N,N',N'-tetraacetic acid, 10% (v/v) glycerol and 1% (v/v) Triton X-100 is added (20 µl per well). The plates are incubated at room temperature for 10 minutes under constant shaking. Luciferase activity is assessed with a bioluminescence reader (Labsystem, Helsinki, Finland) after automatic addition of 50 µl per well luciferase reaction buffer containing 20 mM Tricine, 1.07 mM $(MgCO_3)_4Mg(OH)_2 \cdot 5H_2O$, 2.67 mM $MgSO_4$, 0.1 mM EDTA, 33.3 mM DTT, 270 µM coenzyme A, 470 µM luciferin (Chemie Brunschwig AG), 530 µM ATP, pH 7.8. Lag time is 0.5 seconds, total measuring time is 1 or 2 seconds. Low control values are light units from anti-T cell receptor- or PMA-stimulated cells, high controls are from anti-T cell receptor/anti-CD28- or PMA/ionomycin-stimulated cells without any test sample. Low controls are subtracted from all values. The inhibition obtained in the presence of a test compound is calculated as percent inhibition of the high control. The concentration of test compounds resulting in 50% inhibition ($IC_{50}$) is determined from the dose-response curves.

11. Bone Marrow Proliferation (BM) Assay

Bone marrow cells from CBA mice ($2.5 \times 10^4$ cells per well in flat bottom tissue culture microtiter plates) are incubated in 100 µl RPMI medium containing 10% FCS, 100 U/ml penicillin, 100 µg/ml streptomycin (Gibco BRL, Basel, Switzerland), 50 µM 2-mercaptoethanol (Fluke, Buchs, Switzerland), WEHI-3 conditioned medium (7.5% v/v) and L929 conditioned medium (3% v/v) as a source of growth factors and serially diluted compounds. Seven three-fold dilution steps in duplicates per test compound are performed. After four days of incubation 1 µCi $^3$H-thymidine is added. Cells are harvested after an additional five-hour incubation period, and incorporated $^3$H-thymidine is determined according to standard procedures. Conditioned media are prepared as follows. WEHI-3 cells 1 (ATCC TIB68) and L929 cells (ATCC CCL 1) are grown in RPMI medium until confluence for 4 days and one week, respectively. Cells are harvested, resuspended in the same culture flasks in medium C containing 1% FCS (Schreier and Tees 1981) for WEHI-3 cells and RPMI medium for L929 cells and incubated for 2 days (WEHI-3) or one week (L929). The supernatant is collected, filtered through 0.2 µm and stored in aliquots at −80° C. Cultures without test compounds and without WEHI-3 and L929 supernatants are used as low control values. Low control values are subtracted from all values. High controls without any sample are taken as 100% proliferation. Percent inhibition by the samples is calculated and the concentrations required for 50% inhibition ($IC_{50}$ values) are determined.

12. Allogeneic Mixed Lymphocyte Reaction (MLR)

The two-way MLR is performed according to standard procedures (J. Immunol. Methods, 1973, 2, 279 and Meo T. et al., Immunological Methods, New York, Academic Press, 1979, 227-39). Briefly, spleen cells from CBA and BALB/c mice ($1.6 \times 10^5$ cells from each strain per well in flat bottom tissue culture microtiter plates, $3.2 \times 10^5$ in total) are incubated in RPMI medium containing 10% FCS, 100 U/ml penicillin, 100 µg/ml streptomycin (Gibco BRL, Basel, Switzerland), 50 µM 2-mercaptoethanol (Fluka, Buchs, Switzerland) and serially diluted compounds. Seven three-fold dilution steps in duplicates per test compound are performed. After four days of incubation 1 µCi $^3$H-thymidine is added. Cells are harvested after an additional five-hour incubation period, and incorporated $^3$H-thymidine is determined according to standard procedures. Background values (low control) of the MLR are the proliferation of BALB/c cells alone. Low controls are subtracted from all values. High controls without any sample are taken as 100% proliferation. Percent inhibition by the samples is calculated, and the concentrations required for 50% inhibition ($IC_{50}$ values) are determined.

B. In Vivo

Heart Transplantation Model

The strain combination used: Male Lewis ($RT^1$ haplotype) and BN ($RT^1$ haplotype). The animals are anaesthetised using inhalational isofluorane. Following heparinisation of the donor rat through the abdominal inferior vena cava with simultaneous exsanguination via the aorta, the chest is opened and the heart rapidly cooled. The aorta is ligated and divided distal to the first branch and the brachiocephalic trunk is divided at the first bifurcation. The left pulmonary artery is ligated and divided and the right side divided but left open. All other vessels are dissected free, ligated and divided and the donor heart is removed into iced saline.

The recipient is prepared by dissection and cross-clamping of the infra-renal abdominal aorta and vena cava. The graft is implanted with end-to-side anastomoses, using 1010 monofilament suture, between the donor brachiocephalic trunk and the recipient aorta and the donor right pulmonary artery to the recipient vena cava. The clamps are removed, the graft tethered retroabdominally, the abdominal contents washed with warm saline and the animal is closed and allowed to recover under a heating lamp. Graft survival is monitored by daily palpation of the beating donor heart through the abdominal wall. Rejection is considered to be complete when-heart beat stops. Graft survival is monitored in animals treated with compounds.

Graft v. Host Model

Spleen cells ($2 \times 10^7$) from Wistar/F rats are injected subcutaneously into the right hind footpad of (Wistar/F×Fischer 344)$F_1$ hybrid rats. The left footpad is left untreated. The animals are treated with the test compounds on 4 consecutive days (0-3). The popliteal lymph nodes are removed on day 7, and the weight differences between two corresponding lymph nodes are determined. The results are expressed as the inhibition of lymph node enlargement (given in percent) comparing the lymph node weight differences in the experimental groups to the weight difference between the corresponding lymph nodes from a group of animals left untreated with a test compound. In certain instances the test compound is a selective PKC inhibitor. For example, disclosed compounds that are particularly useful for treating graft versus host disease and related disorders are selective PKC α and θ inhibitors.

Rat Collagen-Induced Arthritis Model (CIA)

Rheumatoid arthritis (RA) is characterized by chronic joint inflammation eventually leading to irreversible cartilage destruction. IgG-containing IC are abundant in the synovial tissue of patients with RA. While it is still debated what role these complexes play in the etiology and pathology of the disease, IC communicate with the hematopoetic cells via the FcγR.

CIA is a widely accepted animal model of RA that results in chronic inflammatory synovitis characterized by pannus formation and joint degradation. In this model, intradermal immunization with native type II collagen, emulsified with incomplete Freund's adjuvant, results in an inflammatory polyarthritis within 10 or 11 days and subsequent joint destruction in 3 to 4 weeks.

Study Protocol

Syngeneic LOU rats are immunized with native type II collagen on Day 0, and efficacy of a test compound is evaluated in a prevention regimen and a treatment regimen. In the prevention protocol, either vehicle or various doses of a test compound are administered via oral gavage starting on day of immunization (Day 0). In the treatment protocol, after clinical signs of arthritis develop on Day 10, treatment with a test compound is initiated (e.g., 300 mg/kg by oral gavage, qd) and continued until sacrifice on Day 28. In both protocols, clinical scores are obtained daily, and body weights are measured twice weekly. At Day 28, radiographic scores are obtained, and serum levels of collagen II antibody are measured by ELISA.

Determination of Results

By 10 days after immunization, rats can develop clinical CIA, as determined by an increase in their arthritis scores. The mean arthritic score gradually increases in the rats treated with vehicle alone after Day 10, and by Day 28 the mean clinical score can reach about 6.75. Mean clinical scores in animals treated from the day of immunization (Day 0) with a test compound can be significantly reduced on Days 10-28 compared with vehicle controls. In the rats treated with a test compound at disease onset, there can be a significantly lower arthritis score beginning around Day 16, and this difference can be observed until the end of the study on Day 28.

Blinded radiographic scores (scale 0-6) can be obtained on Day 28 of CIA and compared between the animals in the vehicle group, animals in the prevention group, and animals in the treatment group.

The groups administered with a test compound, either prophylactically (at immunization) or after disease onset can preclude the development of erosions and reduced soft tissue swelling. Similarly, the groups administered with a test compound can result in reduction of serum anti-collagen II antibody.

Mouse Experimental Autoimmune Encephalomyelitis

The in vivo efficacy of a test compound towards autoimmune diseases can be demonstrated in a mouse model of experimental autoimmune encephalomyelitis (EAE).

Model Description

EAE is a useful model for multiple sclerosis (MS), an autoimmune disease of the CNS that is caused by immune-cell infiltration of the CNS white matter. Inflammation and subsequent destruction of myelin cause progressive paralysis. Like the human disease, EAE is associated with peripheral activation of T cells autoreactive with myelin proteins, such as myelin basic protein (MBP), proteolipid protein (PLP), or myelin oligodendrocyte protein (MOG). Activated neuroantigen-specific T cells pass the blood-brain barrier, leading to focal mononuclear cell infiltration and demyelination. EAE can be induced in susceptible mouse strains by immunization with myelin-specific proteins in combination with adjuvant. In the SJL mouse model used in these studies, hind limb and tail paralysis is apparent by Day 10 after immunization, the peak of disease severity can be observed between Days 10 and 14, and a cycle of partial spontaneous remission followed by relapse can be observed up to Day 35. The results can demonstrate the potential of the test compound to suppress disease severity and prevent relapse of disease symptoms that may be the result of FcγR-mediated cytokine release from immune cells.

Study Protocol

In the SJL murine model of EAE, each mouse is sensitized with PLP/CFA. (150 μg PLP139-151 with 200 μg CFA in 0.05 ml of homogenate on four sites of hind flank for a total of 0.2 ml emulsion is used to induce EAE). In a suppression protocol, either vehicle or various doses of a test compound are administered via oral gavage starting on the day of immunization (Day 0). In a treatment protocol, at onset of disease, animals are separated to achieve groups with a similar mean clinical score at onset and administered vehicle or various dose frequencies of test compounds via oral gavage. In both protocols, clinical scores are monitored daily, and body weights are measured twice weekly.

Determination of Results

By 10 days after PLP immunization, SJL mice can develop clinical EAE, as evidenced by an increase in their mean clinical scores. The paralytic score can gradually increase in the animals treated with vehicle only from the day of immunization (Day 0), and by Day 14 the mean score can reach a peak of about 5.1. At disease peak (e.g., Day 14), the mean clinical score in animals treated with either daily or twice daily can be significantly reduced. By Day 16, animals can exhibit a partial remission of mean clinical severity, which is a characteristic of the SJL model. The lower clinical scores in animals treated twice daily with a test compound can remain significant throughout the experiment until the animals are sacrificed on Day 30. These lower scores throughout the treatment period are reflected in the significantly lower cumulative disease index (CDI) and increase in cumulative weight index (CWI).

SJL mice treated with a test compound at disease onset (e.g., Day 11) can show a significant decrease in CDI. Further, there can be a decrease in the number of relapses in animals treated with a test compound compared with the number of relapses in animals treated with vehicle.

Research Applications

Since subject compounds can inhibit a PKC activity, such compounds are also useful as research tools. The present disclosure also provides a method for using subject compounds as a research tool for studying a biological system or sample, or for discovering new chemical compounds that can inhibit a PKC activity.

The disclosure provides for a method of studying a biological system or sample known to comprise PKC, the method comprising: (a) contacting the biological sample with a compound of Formulae I-V or a salt or solvate or stereoisomer thereof; and (b) determining the inhibiting effects caused by the compound on the biological sample.

Any suitable biological sample having PKC can be employed in such studies which can be conducted either in vitro or in vivo. Representative biological samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest.

When used as a research tool, a biological sample comprising PKC is typically contacted with a PKC activity-inhibiting amount of a subject compound. After the biological sample is exposed to the compound, the effects of inhibition of a PKC activity are determined using conventional procedures and equipment, such as the assays disclosed herein. Exposure encompasses contacting the biological sample with the compound or administering the compound to a subject. The determining step can involve measuring a response (a quantitative analysis) or can involve making an observation (a qualitative analysis). Measuring a response involves, for example, determining the effects of the compound on the biological sample using conventional procedures and equipment, such as radio-ligand binding assays and measuring ligand-mediated changes in functional assays. The assay results can be used to determine the activity level as well as the amount of compound necessary to achieve the desired result, that is, a PKC activity-inhibiting amount.

Additionally, subject compounds can be used as research tools for evaluating other chemical compounds, and thus are also useful in screening assays to discover, for example, new compounds having a PKC inhibiting activity. In this manner, a subject compound can be used as a standard in an assay to allow comparison of the results obtained with a test compound and with the subject compounds to identify those test compounds that have about equal or superior activity, if any. For example, $IC_{50}$ data for a test compound or a group of test compounds is compared to the $IC_{50}$ data for a subject compound to identify those test compounds that have the desired properties, for example, test compounds having an $IC_{50}$ about equal or superior to a subject compound, if any.

This aspect includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a subject compound to provide a second assay value; wherein step (a) is conducted either before, after or concurrently with step (b); and (c) comparing the first assay value from step (a) with the second assay value from step (b). The assays that can be used for generation of comparison data are disclosed herein, such as the PKC assays.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used.

Example 1

Synthesis of 2-chloro-5-fluoro-N4-(1,2,2,6,6-pentamethylpiperidin-4-yl)-4-pyrimidineamine, HCl Salt

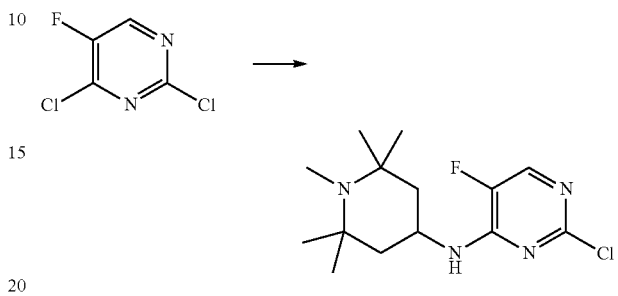

4-Amino-1,2,2,6,6-pentamethylpiperidine (1 g) and 2,6-dichloro-5-fluoropyrimidine (1.5 g) were dissolved in methanol (10 mL). The reaction solution was stirred at room temperature overnight. The reaction solution was evaporated and crystallized from ethyl acetate and hexanes to give 2-chloro-5-fluoro-N4-(1,2,2,6,6-pentamethylpiperidin-4-yl)-4-pyrimidineamine HCl salt (1.65 g, 93%).

$^1$H NMR (DMSO-d$_6$): δ 9.66 (br. s, 1H), 8.32 (d, J=6.9 Hz, 1H), 8.10 (d, J=3.3 Hz, 1H), 4.33 (br. s, 1H), 2.68 (d, J=4.8 Hz, 3H), 2.02 (m, 4H), 1.48 (s, 6H), 1.38 (s, 6H).

Example 2

Synthesis of 2-chloro-5-fluoro-N4-(2,2,6,6-tetramethylpiperidin-4-yl)-4-pyrimidineamine, HCl Salt

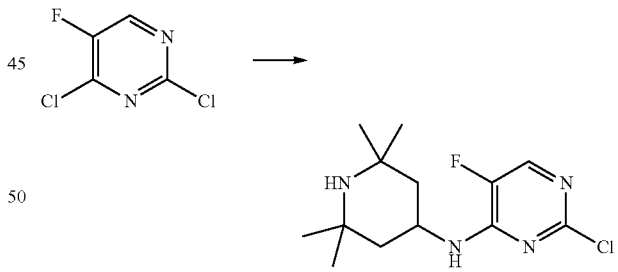

2,4-Dichloro-5-fluoropyrimidine (21.7 g) was dissolved in methanol (400 mL) and cooled to 0° C. 4-Amino-2,2,6,6-tetramethylpiperidine (19.2 mL) was added dropwise. The resulting mixture was slowly warmed to room temperature and stirred overnight. The reaction solution was evaporated and triturated with ethyl to 2-chloro-5-fluoro-N-(2,2,6,6-tetramethylpiperidin-4-yl)-4-pyrimidineamine, HCl salt (36.2 g, 93%).

$^1$H NMR (DMSO-d$_6$): δ 8.24 (d, 1H), 8.16 (d, 1H), 4.38 (m, 1H), 1.92 (d, 2H), 1.63 (t, 2H), 1.39 (d, 12H); m/z=287 (M+H)$^+$.

Example 3

Synthesis of 5-carboxyamide-2,4-dichloropyrimidine

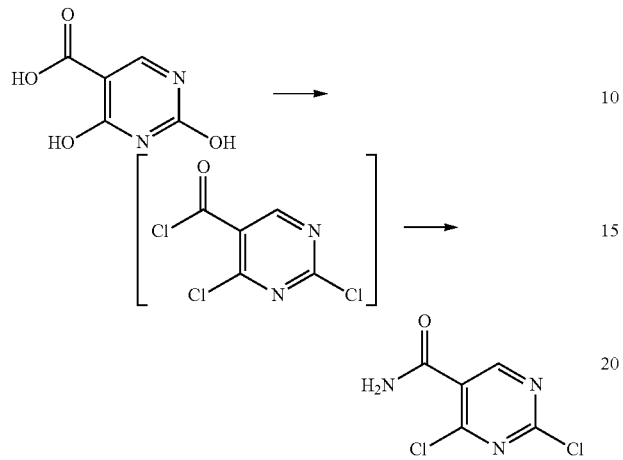

To a 2 L round bottom flask equipped with water condenser and a CaCl$_2$ drying tube, 2,4-dihydroxypyrimidine (25 g, 0.16 mole) was added to PCl$_5$ (117 g, 0.56 mole), and POCl$_3$ (250 ml, 2.6 mole). The mixture was heated at 115° C. overnight to give a clear, slightly light yellow solution. The mixture was cooled to room temperature, and was concentrated under reduced pressure to give pale yellowish oil.

To this oil, anhydrous 1,4-dioxane (300 ml) was added and the mixture was cooled to 0° C. in an ice/water bath. 35 ml of NH$_3$ in water (28%) was added dropwise to the mixture with stirring, temperature was kept below 5° C. The mixture changed from clear to white with precipitate forming, and was stirred for 1 hour at 0° C., reaction was followed by TLC (1:1 Hexanes:Ethyl Acetate). Ethyl acetate (700 ml) and water (500 ml) were added to the mixture, the 2 layers were separated. The organic layer was dried with Na$_2$SO$_4$, and filtered. The solution was concentrated under reduced pressure to give a light yellow solid. This light yellow solid was sonicated with methylene chloride (200 ml), and filtered to give a pale yellow solid (16 g). This pale yellow solid was dissolved into ethyl acetate (1.5 L) and washed with sat. NaHCO$_3$ (500 ml). The organic layer was dried with Na$_2$SO$_4$, filtered, and concentrated under reduced pressure to give 13.1 g of product as a white solid (44% yield).

$^1$H NMR (DMSO-d$_6$, 300 MHz): δ 8.86 (s, 1H), 8.14 (bs, 1H), 8.02 (bs, 1H).

Example 4

Synthesis of 5-carboxyamide-2,4-dichloropyrimidine

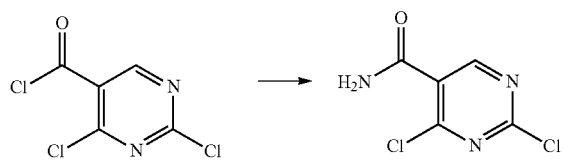 [SMILES: O=C(Cl)c1cnc(Cl)nc1Cl ; NC(=O)c1cnc(Cl)nc1Cl]

Concentrated ammonium hydroxide solution in H$_2$O (assumed to be 8.5M; 14.1 mL; 120 mmol) was added over 15-20 minutes to a stirred solution of 2,4-dichloropyrimidine-5-carbonyl chloride (12.5 g; 60 mmol; Manchester Organics, Sutton Weaver, England) in CH$_2$Cl$_2$ (300 mL) at −15 to −20° C. (internal temperature) [n.b.: a precipitate is formed during the addition]. After complete addition, the mixture was filtered (the filter cake comprises desired product and an impurity—for purification see later). H$_2$O (50 mL) was added to the filtrate, which was partitioned. The organic layer was dried (NaSO$_4$), filtered and the solvent removed under vacuum to give the desired product (1.1 g) as a solid. The filter cake from above was triturated with hot (ca. 50° C.) EtOAc (300 mL) and the mixture filtered—this was repeated another 2 times. The combined filtrates from the trituration were concentrated under vacuum to give another 9.1 g of desired product. The total yield from the reaction is 10.2 g (88%). Data identical to previously reported.

Example 5

Synthesis of 5-carboxyamide-2-chloro-N4-(1,2,2,6,6-pentamethylpiperidin-4-yl)-4-pyrimidineamine, HCl Salt

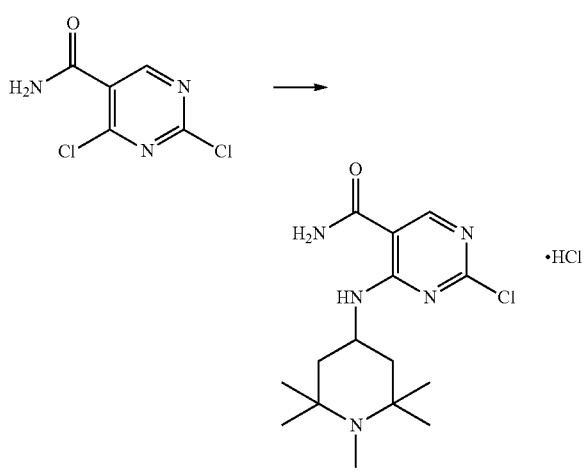

5-carboxyamide-2,4-dichloropyrimidine (7.5 g, 0.04 mole) was dissolved into MeOH (300 ml)/H$_2$O (30 ml). The solution was cooled to 0° C. in a ice/water bath, 4-amino-1,2,2,6,6-pentamethylpiperidine (6.65 g, 0.04 mole) was added drop wise. The mixture was stirred at 0° C. and let warmed up to room temperature over a weekend. Solution was concentrated under reduced pressure to give a light yellow slush. Ethyl acetate (250 ml×2) was added and then concentrated under reduced pressure to remove the remaining traces of methanol and water to give a light yellowish solid. This solid was then sonicated with methylene chloride (100 ml), and filtered using a Buchner funnel, to give 9.5 g of pale yellow solid (75% yield) of the desired product as a HCl salt.

$^1$H NMR (DMSO d$_6$, 300 MHz): δ 9.74 (s, 1H), 9.23 (s, 1H), 8.6 (bs, 1H), 8.39 (bs, 1H), 7.76 (s, 1H), 4.36 (bs, 1H), 2.68 (s, 3H), 2.14 (d, 2H), 1.88 (t, 2H), 1.48 (s, 6H), 1.39 (s, 6H).

Example 6

Synthesis of 5-carboxyamide-2-chloro-N4-(1,2,2,6,6-pentamethylpiperidin-4-yl)-4-pyrimidineamine Free Base

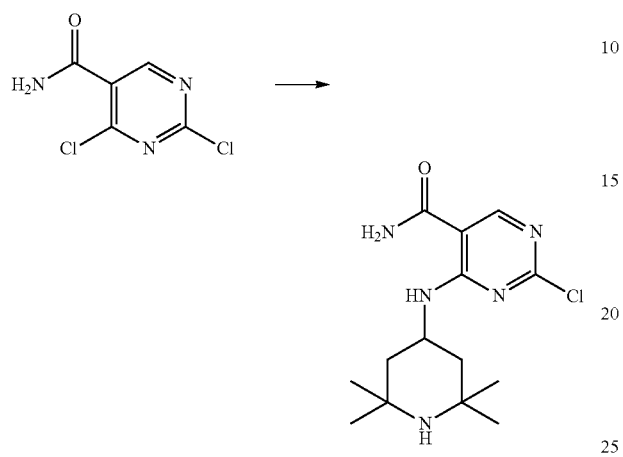

5-carboxyamide-2,4-dichloropyrimidine (7.5 g, 0.04 mole) was dissolved into MeOH (300 ml)/H₂O (30 ml). The solution was cooled to 0° C. in a ice/water bath, 4-amino-2,2,6,6-tetramethylpiperidine (6.8 ml, 0.04 mole) was added drop wise. The mixture was stirred at 0° C. and let warmed up to room temperature over 2 days. Solution was concentrated under reduced pressure to give a light yellow slush. Ethyl acetate (250 ml×2) was added and then concentrated under reduced pressure to remove the remaining traces of methanol and water to give a light yellowish solid. This solid was then sonicated with methylene chloride (100 ml), and filtered using a Buchner funnel, to give a pale yellow solid.

This solid was treated with ethyl acetate (2 L), and sat. NaHCO₃, the 2 layers were separated, and the organic layer was dried with Na₂SO₄. The drying agent was filtered off and the solution was concentrated under reduced pressure to give a white solid (5 g, 41% yield). More of the product can be retrieved from the aqueous layer by back extracting it with more ethyl acetate.

¹H NMR (DMSO-d₆, 300 MHz): δ 9.14 (d, 1H), 8.54 (s, 1H), 8.18 (bs, 1H), 7.68 (s, 1H), 4.30 (bs, 1H), 1.79 (d, 2H), 1.15 (s, 6H), 1.02 (s, 6H); m/z=312.2 (M+H)⁺.

Example 7

Synthesis of 5-cyano-2-chloro-N4-(2,2,6,6-tetramethylpiperidin-4-yl)-4-pyrimidineamine

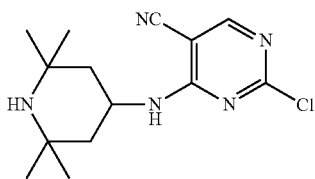 [SMILES: CC1(C)CC(Nc2nc(Cl)ncc2C#N)CC(C)(C)N1]

Burgess reagent-methyl (N-triethylammoniumsulfonyl) carbamate—(238 mg; 1.0 mmol) was added in one portion to a stirred solution of 5-carboxamide-2-chloro-N4-(2,2,6,6,-tetramethylpiperidin-4-yl)-4-pyrimidineamine (156 mg; 0.5 mmol) in 1,2-dichloroethane (3 mL) at room temperature. The mixture was heated to 70° C. and stirred for 2 hours. After allowing to cool to room temperature the mixture was diluted with further 1,2-dichloroethane (20 mL) and H₂O (30 mL). The aqueous and organic layers were partitioned and the organic layer washed with sat. NaHCO₃ then dried (Na₂SO₄), filtered and the solvent removed under vacuum to leave a crude viscous oil (NMR shows this to be product and unreacted Burgess reagent). The crude oil was purified by column chromatography on silica gel using EtOAc:MeOH (9:1) then EtOAc:MeOH:Et₃N (90:8:2) as eluent to give the desired product (75 mg, 51%) as a foam solid. This solid was usually used directly in the next step.

Example 8

Synthesis of 5-cyano-2-chloro-N4-(2,2,6,6-tetramethylpiperidin-4-yl)-4-pyrimidineamine

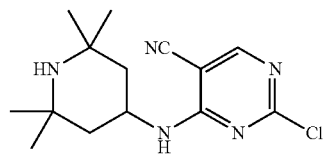 [SMILES: CC1(C)CC(Nc2nc(Cl)ncc2C#N)CC(C)(C)N1]

Trifluoroacetic anhydride (9.4 mL; 67.3 mmol) was added dropwise over 30-45 minutes to a stirred solution of 5-carboxyamide-2-chloro-N4-(2,2,6,6-tetramethylpiperidin-4-yl)-4-pyrimidineamine (2.1 g, 6.7 mmol) and Et₃N (11.3 mL; 80.8 mmol) in THF (40 mL) at −78° C. under nitrogen. After complete addition, the mixture was stirred at −78° C. for a further 60 minutes, then a saturated solution of NaHCO₃ (30 mL) was added dropwise keeping the internal temperature below −30° C. After complete addition of the NaHCO₃, EtOAc (150 mL) and H₂O (100 mL) was added and the mixture was stirred for 10 minutes. Further H₂O (200 mL) was added and the organic and aqueous layers were partitioned. The aqueous layer was extracted with EtOAc (4×150 mL)—until substantially all precipitated material had gone in to solution. The combined organic extracts were washed with brine (1×50 mL), dried (Na₂SO₄), filtered and the solvent removed under vacuum to leave a crude solid with TFAA and Et₃N residues. The solid was triturated with Et₂O (50 mL) and filtered to give the product (2.1 g) as a TFA salt.

Example 9

Formation of Free Base of 5-cyano-2-chloro-N4-(2,2,6,6-tetramethylpiperidin-4-yl)-4-pyrimidineamine The TFA product of 5-cyano-2-chloro-N4-(2,2,6,6-tetramethylpiperidin-4-yl)-4-pyrimidineamine (2.1 g) was partitioned between EtOAc (100 mL) and 0.2 M NaOH (50 mL). The organic layer was washed with brine (1×50 mL), dried (Na₂SO₄), filtered and the solvent removed under vacuum to leave the product (1.35 g, 68%) as a solid.

¹H NMR (DMSO-d₆, 300 MHz): δ 8.51 (s, 1H), 8.34 (br. s, 1H), 4.42 (t, 1H), 1.61 (br. d, 2H), 1.23 (t, 2H), 1.14 (s, 6H), 1.02 (s, 6H); m/z=294.1 (M+H)⁺ for ³⁵Cl.

Example 10

Synthesis of 5-cyano-2-chloro-N4-(1,2,2,6,6-pentamethylpiperidin-4-yl)-4-pyrimidineamine

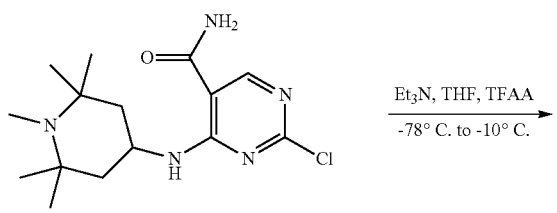

Trifluoroacetic anhydride (9.35 mL; 67.3 mmol, 10 eq) was added dropwise over 30-45 min to a stirred solution of 5-carboxyamide-2-chloro-N4-(1,2,2,6,6-pentamethylpiperidin-4-yl)-4-pyrimidineamine hydrochloride (2.19 g, 6.73 mmol, 1 eq) and Et$_3$N (11.26 mL; 80.76 mmol, 12 eq) in THF (45 mL) at −78° C. under nitrogen. After complete addition, the mixture was stirred at −78° C. for a further 60 minutes, then a saturated solution of NaHCO$_3$ (30 mL) was added dropwise keeping the internal temperature below −30° C. After complete addition of the NaHCO$_3$, EtOAc (100 mL) and H$_2$O (100 mL) was added and the mixture was stirred for 10 minutes. Further H$_2$O (100 mL) was added and the organic and aqueous layers were partitioned. The aqueous layer was extracted with EtOAc (4×100 mL)—until all precipitated material had gone in to solution. The combined organic extracts were washed with brine (1×50 mL), dried (Na$_2$SO$_4$), filtered and the solvent removed under vacuum to leave a crude solid with TFAA and Et$_3$N residues. The crude solid was dissolved in 100 mL of EtOAc and partitioned with 1 N aq. NaOH (50 mL). The ethyl acetate layer was extracted with 2×50 mL aqueous 1N NaOH. The combined organic extracts were washed with brine (1×50 mL), dried (Na$_2$SO$_4$), filtered and the solvent removed under vacuum to give light yellow solid (1.80 g, in 87% yield).

$^1$H NMR (DMSO-d$_6$, 300 MHz): δ 8.51 (s, 1H), 8.37 (d, 1H), 4.31 (br. m, 1H), 2.15 (s, 3H), 1.47-1.66 (m, 4H), 1.06 (s, 6H), 1.00 (s, 6H); m/z=309 (M+H)$^+$.

Example 11

Synthesis of 2-bromo-4-fluoro-5-nitroaniline

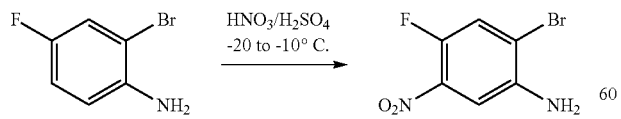

2-bromo-4-fluoroaniline (47.5 g, 250 mmol) was added to a solution of concentrated H$_2$SO$_4$ (300 mL) keeping the internal temperature below 30° C. The mixture was aged for ca. 30-60 minutes then cooled to −20° C. 90% HNO$_3$ (35 g) was added dropwise over ca. 60 minutes keeping the internal temperature between −15 to −20° C. TLC indicated a slight amount of starting material, so a further aliquot of 90% HNO$_3$ (3 g) was added over 5 minutes at −15 to −20° C. The cold mixture was then poured on to ice H$_2$O (ca. 1 L ice+500 mL H$_2$O) and EtOAc (1 L). The aqueous and organic layers were partitioned and the organic layer was washed with sat. NaHCO$_3$ (2×500 mL), dried (Na$_2$SO$_4$), filtered and the solvent removed under vacuum to leave a dark solid (35 g, 60%).

$^1$H NMR (DMSO-d$_6$, 300 MHz): δ 8.27 (br. s, 2H), 7.70 (d 1H), 7.47 (d, 1H); m/z=275.9 (M+MeCN+H)$^+$ for $^{79}$Br.

Example 12

Synthesis of 2-cyclopropyl-4-fluoro-5-nitroaniline

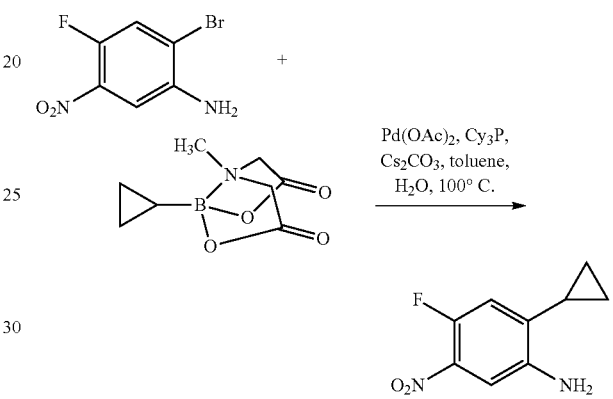

A mixture of 2-bromo-4-fluoro-5-nitroaniline (12 g, 51 mmol), cyclopropylboronic acid MIDA ester (Aldrich; 20.1 g, 102 mmol), Pd(OAc)$_2$ (1.72 g, 7.7 mmol), Cy$_3$P (4.3 g, 15.3 mmol) and Cs$_2$CO$_3$ (98.8 g, 306 mmol) in toluene (120 mL) and H$_2$O (40 mL) was de-gassed with N$_2$ for 15 minutes. The mixture was then heated at 100° C. (oil bath temperature) overnight (the reaction mixture can also be heated to reflux). After allowing to cool to room temperature, the mixture was diluted with EtOAc (200 mL) and H$_2$O (100 mL) and the mixture filtered through Celite. The filter cake was washed with EtOAc (2×100 mL) and the filtrate partitioned. The organic layer was dried (Na$_2$SO$_4$), filtered and the solvent removed under vacuum to leave a crude residue. The residue was purified by column chromatography on silica gel (residue dry-loaded on to silica gel) using EtOAc/hexanes (1:4 to 3:7) as eluent to give the product (8.1 g, 81%) as a dark solid.

$^1$H NMR (DMSO-d$_6$, 300 MHz): δ 7.27 (d 1H), 6.84 (d, 1H), 5.52 (br. S, 2H), 1.74-1.83 (m, 1H), 0.92-0.98 (m, 2H), 0.62-0.73 (m, 2H); m/z=238.0 (M+MeCN+H)$^+$.

Example 13

Synthesis of 2-cyclopropyl-4-fluoro-5-nitroaniline Using Potassium Cyclopropyltrifluoroborate

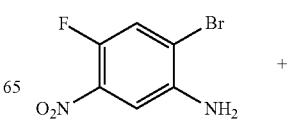

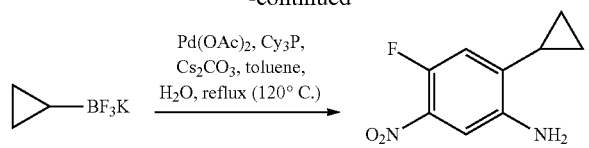

A mixture of 2-bromo-4-fluoro-5-nitroaniline (13.1 g, 56 mmol), potassium cyclopropyltrifluoroborate (16.5 g, 112 mmol), Pd(OAc)$_2$ (1.89 g, 8.4 mmol), Cy$_3$P (4.7 g, 16.8 mmol) and Cs$_2$CO$_3$ (109.5 g, 336 mmol) in toluene (150 mL) and H$_2$O (60 mL) was de-gassed with N$_2$ for 15 minutes. The mixture was then heated at reflux overnight (120° C. oil bath temperature). After allowing to cool to room temperature, the mixture was diluted with EtOAc (200 mL) and H$_2$O (200 mL) and the mixture filtered through Celite. The filter cake was washed with EtOAc (3×100 mL) and the filtrate transferred to a separating funnel. Brine (200 mL) was added and the aqueous and organic layers partitioned. The organic layer was dried (Na$_2$SO$_4$), filtered and the solvent removed under vacuum to leave a crude residue. The residue was purified by column chromatography on silica gel (residue dry-loaded on to silica gel) using EtOAc/hexanes (1:9 to 1:4) as eluent to give the product (8.3 g, 76%) as a dark solid. Data same as above.

The reaction in Example 13 was performed with other reaction conditions. For example, the following modifications to the reaction conditions of Example 13 have been used:
1) Ratio of potassium cyclopropyltrifluoroborate to 2-bromo-4-fluoro-5-nitroaniline ranging from 1.1 to 1.5;
2) Molar percentage of Pd(OAc)$_2$ ranging from 0.1 to 15;
3) Molar percentage of Cy$_3$P ranging from 0.2 to 30;
4) Molar equivalents of Cs$_2$CO$_3$ ranging from 2 to 6;
5) Use of K$_3$PO$_4$ or K$_3$CO$_3$ instead of Cs$_2$CO$_3$ as a base in molar equivalents ranging from 2 to 6;
6) The volume of solvent ranging being 7 ml for reaction of 500 mg of 2-bromo-4-fluoro-5-nitroaniline;
7) The solvent mixture being dioxane/water;
8) The reaction temperature ranging from 60° C. to reflux;
9) The reaction time ranging from 16 hours to 22 hours.

Example 14

Synthesis of 1-(2-cyclopropyl-4-fluoro-5-nitrophenyl)-1H-tetrazole

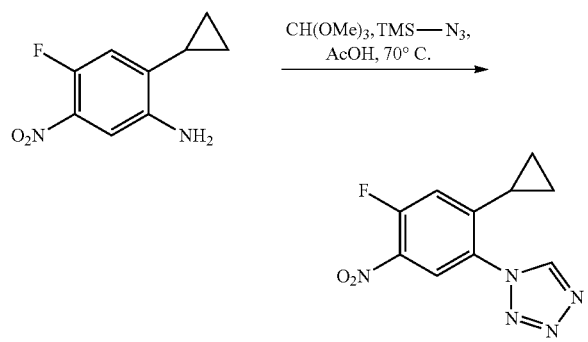

N.b.: TMS-N$_3$ and tetrazole product are potentially explosive. Use a blast shield for this reaction and glassware with no scratches, cracks, etc. Avoid contact with metals, including metal spatulas. Keep the product slightly wet with residual solvent from the column.

A mixture of 2-cyclopropyl-4-fluoro-5-nitroaniline (10.9 g, 55.6 mmol), trimethylsilyl azide (14.6 mL, 111.1 mmol), trimethylorthoformate (60.9 mL, 556 mmol) in AcOH (110 mL) was heated to 70° C. and stirred overnight and performed behind a blast shield. After allowing the reaction mixture to cool to room temperature, the mixture was concentrated under vacuum behind a blast shield. The crude residue was partitioned between EtOAc (500 mL) and H$_2$O which had been adjusted to ca. pH 12-14 with 3N NaOH (300 mL). The aqueous and organic layers were partitioned and the aqueous extracted with EtOAc (2×150 mL). The combined organic extracts were washed with brine (1×100 mL), dried (Na$_2$SO$_4$), filtered and the solvent removed under vacuum—silica gel was added at this stage so that the crude product was absorbed directly on to silica gel. The crude product was purified by column chromatography on silica gel using EtOAc/hexanes (30-60% EtOAc in increments of 10% EtOAc) to give the product (12.28 g, 89%) as a pale solid.

$^1$H NMR (CDCl$_3$, 300 MHz): δ 8.97 (s, 1H), 8.18 (d 1H), 7.01 (d, 1H), 1.58-1.66 (m, 1H), 1.14-1.21 (m, 2H), 0.86-0.90 (m, 2H); m/z=291.1 (M+MeCN+H)$^+$.

A differential scanning calorimetry was run and indicated that the product has a large energy release ('exo-peak') above 170° C.

Example 15

Synthesis of 4-cyclopropyl-2-fluoro-5-(1H-tetrazol-1-yl)benzenamine

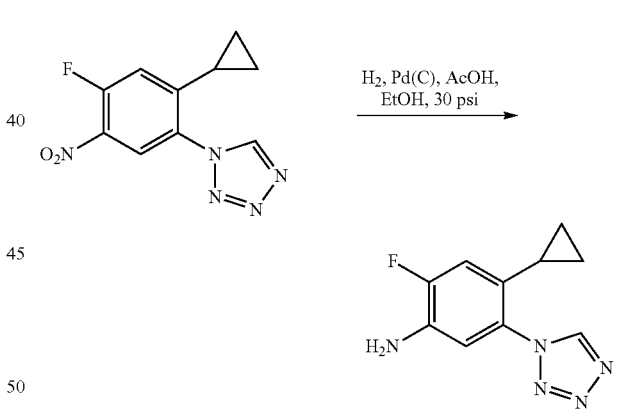

A Parr vessel was charged with 1-(2-cyclopropyl-4-fluoro-5-nitrophenyl)-1H-tetrazole (27.20 g, 109.14 mmol), EtOH (1000 mL), AcOH (14 mL), and 10% Pd/C (50% in water, Degussa type E101; 5.44 g, 20% by weight of the starting nitro compound) giving a suspension. The vessel was sealed, degassed, and back-filled with H$_2$ (×3). The vessel was then charged with 30 psi H$_2$ and allowed to shake until LCMS analysis indicated complete conversion. The reaction mixture was filtered through a pad of celite, and the pad of celite was rinsed with DCM/MeOH (1:9, 200 mL). The filtrate was evaporated to dryness, and the resulting solid was dried in vacuo overnight in a 30° C. water bath to remove any traces of AcOH. The crude product was triturated with MeOH to give the product, 4-cyclopropyl-2-fluoro-5-(1H-tetrazol-1-yl) benzenamine (18.60 g, 78%) as a yellow solid.

$^1$H NMR (DMSO d$_6$, 300 MHz): δ 9.81 (s, 1H), 9.78 (br. s, 1H), 6.90 (d, 1H, J=12.3 Hz), 6.80 (d, 1H, J=8.7 Hz), 5.47 (bs, 2H), 1.36-1.45 (m, 1H), 0.580-0.643 (m, 2H), 0.413-0.465 (m, 2H); m/z=220 (M+H)$^+$.

Example 16

Synthesis of 4-(2,2,6,6-tetramethylpiperidin-4-ylamino)-2-(4-cyclopropyl-2-fluoro-5-(1H-tetrazol-1-yl)phenylamino)pyrimidine-5-carbonitrile

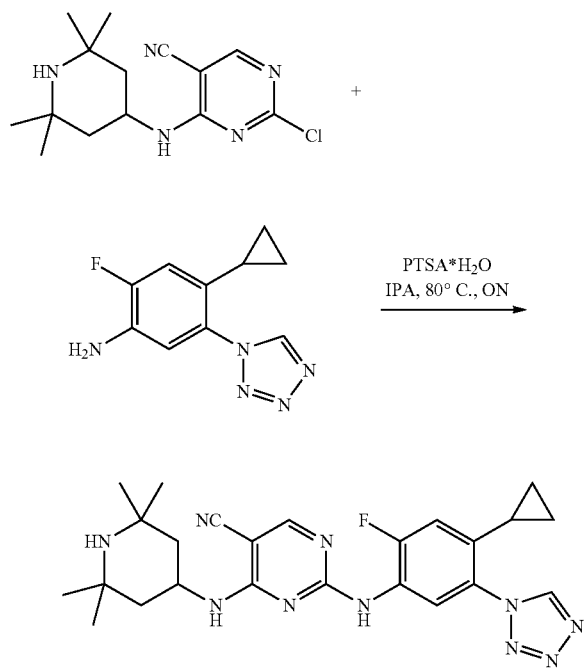 [SMILES: CC1(C)CC(Nc2nc(Cl)ncc2C#N)CC(C)(C)N1 ; Nc1cc(-n2cnnn2)c(C2CC2)cc1F ; CC1(C)CC(Nc2nc(Nc3cc(-n4cnnn4)c(C4CC4)cc3F)ncc2C#N)CC(C)(C)N1]

A mixture of 4-(2,2,6,6-tetramethylpiperidin-4-ylamino)-2-chloropyrimidine-5-carbonitrile (112 mg, 0.380 mmol, 1 equiv), 4-cyclopropyl-2-fluoro-5-(1H-tetrazol-1-yl)benzenamine (100 mg, 0.456 mmol, 1.2 equiv), and para-toluenesulfonic acid monohydrate (58 mg, 0.304 mmol, 0.8 equiv) in IPA (4 mL) were heated to 80° C. overnight. LCMS indicated desired product plus approximately 18% of 5-fluoro-2-isopropoxy-N-(2,2,6,6-tetramethylpiperidin-4-yl)pyrimidin-4-amine byproduct. After cooling to ambient temperature, the crude mixture was quenched with 2M NH$_3$/MeOH followed by concentrating to dryness and repeating once. The crude product was purified by flash chromatography and eluted with DCM:2M NH$_3$/MeOH (100:0 to 95:5 using 1% 2M NH$_3$/MeOH increments) to provide the desired product which was recrystallized with DCM/IPA to give the title compound (88 mg, 49%) as a solid.

$^1$H NMR (DMSO d$_6$, 300 MHz): δ 9.81 (s, 1H), 9.51 (br. s, 1H), 8.28 (s, 1H), 7.64 (d, J=7.8 Hz, 1H), 7.38 (d, J=7.8 Hz, 1H), 7.08 (d, J=11.7 Hz, 1H), 4.28 (br. s, 1H), 1.44-1.47 (m, 2H), 1.08-1.17 (m, 2H), 0.76-0.94 (m, 16H), 0.57-0.59 (m, 2H); m/z=477 (M+H)$^+$.

Example 17

Synthesis of 5-fluoro-N2-(2-fluoro-5-(1H-tetrazol-1-yl)phenyl)-N4-(2,2,6,6-tetramethylpiperidin-4-yl)pyrimidine-2,4-diamine

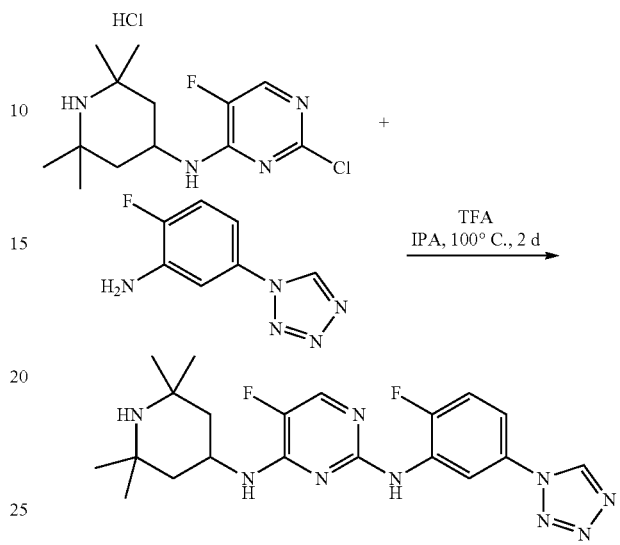

A mixture of 2-chloro-5-fluoro-N-(2,2,6,6-tetramethylpiperidin-4-yl)pyrimidin-4-amine hydrochloride (100 mg, 0.309 mmol, 1 equiv), 2-fluoro-5-(1H-tetrazol-1-yl)benzenamine (90 mg, 0.495 mmol, 1.6 equiv., Chembridge, San Diego, Calif.), and TFA (100 μL, 1.24 mmol, 4 equiv) in IPA (3 mL) were heated to 100° C. in shaker overnight affording a melt. LCMS indicated pyrimidine:product ratio=29:71. IPA (1 mL) and TFA (100 μL, 1.24 mmol, 4 equiv) were added and the mixture was heated to 100° C. in shaker overnight affording a melt. LCMS indicated pyrimidine:product=4:96. IPA (1 mL) and TFA (1000 μL, 12.4 mmol, 40 equiv) were added and the mixture was heated to 100° C. in shaker for an additional 5 hours affording a melt. LCMS indicated complete conversion to product. The crude solid was quenched with 2M NH$_3$/MeOH (1-2 mL), and diluted with DCM (3-5 mL), then loaded into a column packed with silica and filled with DCM. The crude product was purified by flash chromatography and eluted with DCM:2M NH$_3$/MeOH=100:0 to 96:4 using 1% 2M NH$_3$/MeOH increments to provide the desired product (90 mg, 68%) as a solid.

$^1$H NMR (DMSO d$_6$, 300 MHz): δ 10.06 (d, 1H, J=2.10 Hz), 8.75 (br. s, 1H), 8.35-8.37 (m, 1H), 7.86-7.88 (m, 1H), 7.42-7.52 (m, 2H), 7.22 (d, 1H, J=8.40 Hz), 4.17-4.26 (m, 1H), 1.50-1.59 (m, 2H), 0.80-1.18 (m, 15H); LCMS (m/z): 430 (MH$^+$)

Example 18

Synthesis of 5-fluoro-N2-(2-fluoro-5-(1H-tetrazol-1-yl)phenyl)-N4-(1,2,2,6,6-pentamethylpiperidin-4-yl)pyrimidine-2,4-diamine

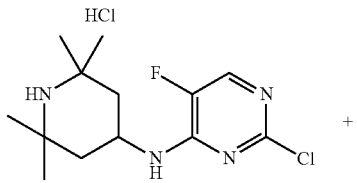

-continued

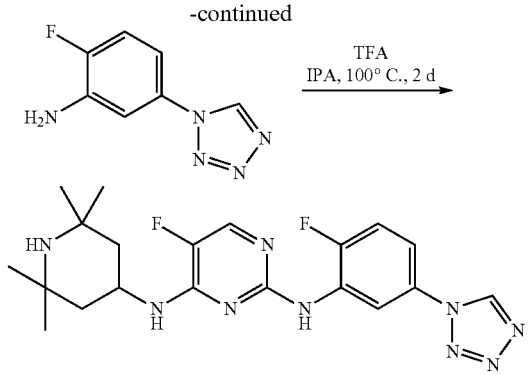

A mixture of 2-chloro-5-fluoro-N-(1,2,2,6,6-pentamethylpiperidin-4-yl)pyrimidin-4-amine hydrochloride (100 mg, 0.296 mmol, 1 equiv), 2-fluoro-5-(1H-tetrazol-1-yl)benzenamine (85 mg, 0.474 mmol, 1.6 equiv), and TFA (100 µL, 1.19 mmol, 4 equiv) in IPA (3 mL) were heated to 100° C. in shaker overnight affording a melt. LCMS indicated pyrimidine:product=5:95. IPA (1 mL) and TFA (100 µL, 1.19 mmol, 4 equiv) were added and the mixture was heated to 100° C. in shaker ON affording a melt. LCMS indicated pyrimidine:product=2:98. IPA (1 mL) and TFA (1000 uL, 11.9 mmol, 40 equiv) were added and the mixture was heated to 100° C. in shaker for an additional 5 hours affording a melt. LCMS indicated complete conversion to product. The crude solid was quenched with 2M $NH_3$/MeOH (1-2 mL), and diluted with DCM (3-5 mL), then loaded into a column packed with silica and filled with DCM. The crude product was purified by flash chromatography and eluted with DCM:2M $NH_3$/MeOH=100:0 to 97:3 using 1% 2M $NH_3$/MeOH increments to provide the desired product (91 mg, 69%) as a solid.

$^1$H NMR (DMSO $d_6$, 300 MHz): δ 10.06 (d, 1H, J=2.10 Hz), 8.77 (br. s, 1H), 8.34-8.37 (m, 1H), 7.88 (br. s, 1H), 7.42-7.52 (m, 2H), 7.23 (bs, 1H), 4.17-4.25 (m, 1H), 2.05 (br. s, 3H), 1.50-1.59 (m, 2H), 1.29-1.37 (m, 2H), 0.97 (br. s, 6H), 0.66 (br. s, 6H); LCMS (m/z): 444 (MH$^+$).

Example 19

Synthesis of 4-(2,2,6,6-tetramethylpiperidin-4-ylamino)-2-(4-cyclopropyl-2-fluoro-5-(1H-tetrazol-1-yl)phenylamino)pyrimidine-5-Carboxamide

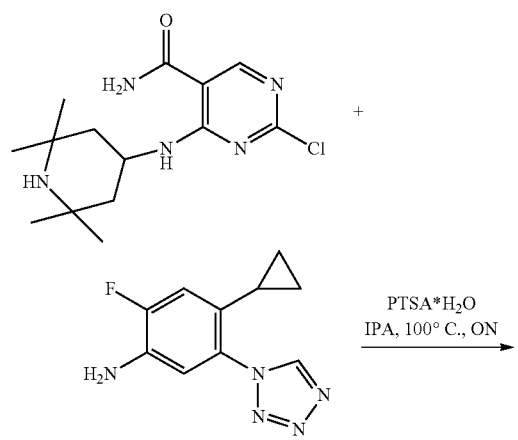

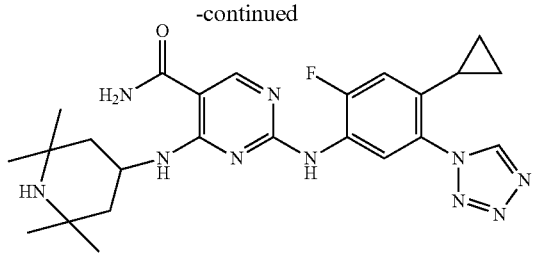

A mixture of 4-(2,2,6,6-tetramethylpiperidin-4-ylamino)-2-chloropyrimidine-5-carboxamide (178 mg, 0.570 mmol, 1 equiv), 4-cyclopropyl-2-fluoro-5-(1H-tetrazol-1-yl)benzenamine (150 mg, 0.684 mmol, 1.2 equiv), and PTSA monohydrate (230 mg, 1.20 mmol, 2.1 equiv) in IPA (6 mL) were heated to 100° C. overnight giving a precipitate. The precipitate was collected by vacuum filtration and rinsed with IPA. The solid was taken in EtOAc then adjusted to ca. pH 12-14 with 1N NaOH. The aqueous and organic layers were partitioned. The aqueous layer was extracted with EtOAc (2×150 mL). The combined organics were washed with 1N NaOH (1×150 mL), dried ($Na_2SO_4$), filtered, and concentrated to give the desired product (128 mg, 50%) as a solid.

$^1$H NMR (DMSO $d_6$, 300 MHz): δ 9.83 (s, 1H), 9.08 (br. s, 1H), 8.96 (d, 1H, J=8.70 Hz), 8.47 (s, 1H), 7.77 (d, 2H, J=6.90 Hz), 7.09 (d, 2H, J=11.70 Hz), 4.20-4.22 (m, 1H), 1.63-1.67 (m, 2H), 1.43-1.49 (m, 1H), 0.99-1.19 (m, 1H), 0.73-0.95 (m, 15H), 0.57-0.61 (m, 2H); LCMS (m/z): 495 (MH$^+$).

Example 20

Synthesis of N2-(4-cyclopropyl-2-fluoro-5-(1H-tetrazol-1-yl)phenyl)-5-fluoro-N4-(2,2,6,6-tetramethylpiperidin-4-yl)pyrimidine-2,4-diamine 1.5 Formic Acid

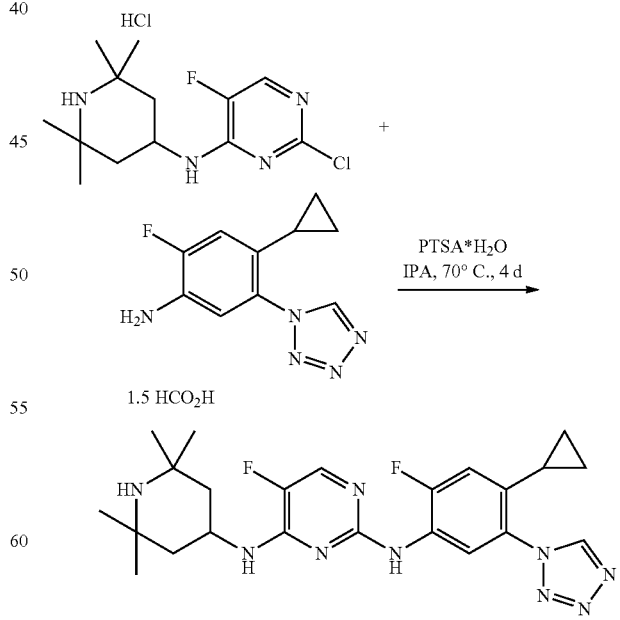

A mixture of 2-chloro-5-fluoro-N-(2,2,6,6-tetramethylpiperidin-4-yl)pyrimidin-4-amine hydrochloride (184 mg, 5.70 mmol, 1 equiv), 4-cyclopropyl-2-fluoro-5-(1H-tetrazol-1-yl)

benzenamine (150 mg, 0.684 mmol, 1.2 equiv), and PTSA monohydrate (87 mg, 0.456 mmol, 0.8 equiv) in IPA (6 mL) were heated to 70° C. for 4 days. LCMS indicated 2-4% of the cleaved tetrazole product (the corresponding aniline N2-(5-amino-4-cyclopropyl-2-fluorophenyl)-5-fluoro-N4-(2,2,6,6-tetramethylpiperidin-4-yl)pyrimidine-2,4-diamine) and 5-7% unreacted 2-chloro-5-fluoro-N-(2,2,6,6-tetramethylpiperidin-4-yl)pyrimidin-4-amine. After cooling to ambient temperature, the crude mixture was concentrated to dryness. The residue was taken in ice-cold water and EtOAc then adjusted to ca. pH 12-14 with 1N NaOH. The aqueous and organic layers were partitioned, and the aqueous layer was extracted with EtOAc (1×150 mL). The combined organic extracts were dried ($Na_2SO_4$), filtered, and the solvent removed under vacuum. The crude product was purified by reverse-phase HPLC using formic acid as a modifier in water and acetonitrile to give formate salt (141 mg, 46%) as a solid.

$^1$H NMR (DMSO $d_6$, 300 MHz): δ 9.84 (s, 1H), 8.66 (br. s, 1H), 8.31 (s, 1.5H, formic acid), 7.89 (d, 1H, J=7.5 Hz), 7.85 (d, 1H, J=2.1 Hz), 7.42 (d, 1H, J=8.01 Hz), 7.08 (d, 1H, J=12.0 Hz), 4.31-4.20 (m, 1H), 1.60-1.75 (m, 2H), 1.10-1.51 (m, 16H), 0.70-0.77 (m, 2H), 0.54-0.59 (m, 2H); LCMS (m/z): 470 (MH$^+$) free base.

Alternative synthesis using a scavenging technique to remove unreacted 2-chloro-5-fluoro-N-(2,2,6,6-tetramethylpiperidin-4-yl)pyrimidin-4-amine is as follows.

A mixture of 2-chloro-5-fluoro-N-(2,2,6,6-tetramethylpiperidin-4-yl)pyrimidin-4-amine hydrochloride (6.68 g, 20.68 mmol, 1 equiv), 4-cyclopropyl-2-fluoro-5-(1H-tetrazol-1-yl)benzenamine (6.80 g, 31.02 mmol, 1.5 equiv), and PTSA monohydrate (3.15 g, 16.54 mmol, 0.8 equiv) in IPA (200 mL) were heated to 70° C. for 4 days. LCMS indicated 2-4% of the cleaved tetrazole product and 7-9% unreacted 2-chloro-5-fluoro-N-(2,2,6,6-tetramethylpiperidin-4-yl)pyrimidin-4-amine. After cooling the reaction mixture to ambient temperature, 3-amino benzoic acid (8.51 g, 62.04 mmol, 3 equiv) was added and heated to 70° C. for overnight to scavenge the unreacted pyrimidine. After cooling to ambient temperature, the crude mixture was concentrated to dryness. The residue was taken in ice-cold water and EtOAc then adjusted to ca. pH 12-14 with 1N NaOH (300 mL). The aqueous and organic layers were partitioned, and the organic layer washed with 1N NaOH (2×300 mL). The aqueous layer was extracted with EtOAc (1×150 mL). The combined organic extracts were dried ($Na_2SO_4$), filtered, and the solvent removed under vacuum. The crude product was purified by flash chromatography and eluted with DCM:2M $NH_3$/MeOH=100:0 to 96:4 using 1% 2M $NH_3$/MeOH increments to provide the desired product which was triturated with EtOAc/hexane to give the title compound (5.16 g, 53%) as a solid.

$^1$H NMR (DMSO $d_6$, 300 MHz): δ 9.82 (d, 1H, J=1.50 Hz), 8.58 (br. s, 1H), 7.87 (d, 1H, J=7.5 Hz), 7.81 (d, 1H, J=2.1 Hz), 7.18 (d, 1H, J=8.0 Hz), 7.06 (d, 1H, J=12.0 Hz), 4.20-4.22 (m, 1H), 1.54-1.58 (m, 2H), 1.42-1.43 (m, 1H), 0.91-1.11 (m, 15H), 0.71-0.74 (m, 2H), 0.55-0.56 (m, 2H); LCMS (m/z): 470 (MH$^+$).

A certain large-scale synthesis procedure is as follows:

A mixture of 2-chloro-5-fluoro-N-(2,2,6,6-tetramethylpiperidin-4-yl)pyrimidin-4-amine hydrochloride (16.2 g, 50.2 mmol), 4-cyclopropyl-2-fluoro-5-(1H-tetrazol-1-yl)benzenamine (15.0 g, 60.2 mmol) and para-toluenesulfonic acid monohydrate (7.64 g, 40.1) in IPA (400 mL) were heated to 70° C. and stirred for 4-5 days. After cooling, the mixture was filtered and the filter cake was washed with isopropyl alcohol (2×50 mL). The filter cake was suspended in EtOAc (500 mL) and $H_2O$ (300 mL). 1N NaOH was added to basify the mixture. The organic and aqueous layers were partitioned and the organic layer was washed with 1N NaOH (300 mL), brine (300 mL), then dried (MgSO$_4$), filtered and the solvent removed under vacuum to leave a solid (LC/MS indicated this solid to be >96% purity). The solid was triturated with EtOAc/hexanes (1:9; ca. 300 mL)—the mixture heated to ca. 50° C. and allowed to cool to room temperature, then filtered and the filter cake washed with EtOAc/hexanes (1:9; 2×100 mL) to give the title compound (15 g, 64%) as a solid. Characterization data is the same to that shown above.

Example 21

Synthesis of 4,6-dinitro-2-fluorophenol

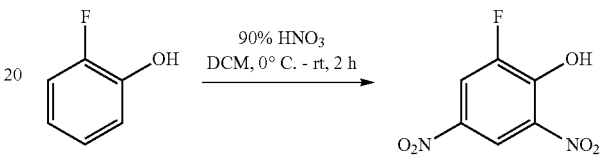

To 2-fluorophenol (10 mL, 12.1 g, 108 mmol, 1 equiv) in anhydrous DCM at 0° C. was added 90% $HNO_3$ (12.6 mL, 17.0 g, 270 mmol, 2.5 equiv) dropwise. The mixture was warmed to room temperature and stirred for 2 hours, then cooled to 0° C. again and quenched with 2N NaOH solution to pH 5 (ca. 80 mL). The mixture was concentrated, diluted with water and extracted with EtOAc (3×150 mL). The combined organic layers was dried over MgSO$_4$, filtered and concentrated. The residue was triturated in hexanes to give the product (18 g, 82%) as a yellow solid.

$^1$H NMR (CDCl$_3$, 300 MHz): δ 10.97 (br. s, 1H), 8.92-8.90 (m, 1H), 8.32 (dm, J=9.3 Hz, 1H); m/z=201 (M−H)$^+$.

Example 22

Synthesis of 2-bromo-1,5-dinitro-3-fluorobenzene

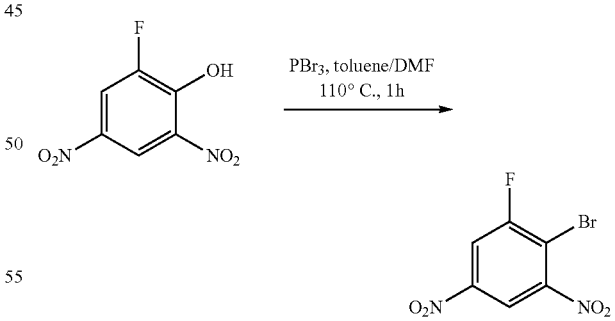

To a solution of 4,6-dinitro-2-fluorophenol (8 g, 39.60 mmol, 1 equiv) in DMF (24 mL) and toluene (160 mL), PBr$_3$ (5.6 mL, 59.40 mmol, 1.5 equiv) was added at room temperature. Then the reaction mixture was heated at 110° C. for 1 hour. After allowing to cool to room temperature, the upper colorless layer was poured into a separate funnel and diluted with hexanes. The organic layer was washed with water, dried over MgSO$_4$ and evaporated to dryness to give the product (10.3 g, 98%) as a yellow solid.

$^1$H NMR (CDCl$_3$, 300 MHz): δ 8.54 (d, J=1.2 Hz, 1H), 8.22 (dd, J=7.5, 0.9 Hz, 1H); m/z=264 (M$^+$)$^+$.

Example 23

Synthesis of 2-bromo-3-fluoro-5-nitroaniline and 4-bromo-3-fluoro-5-nitroaniline

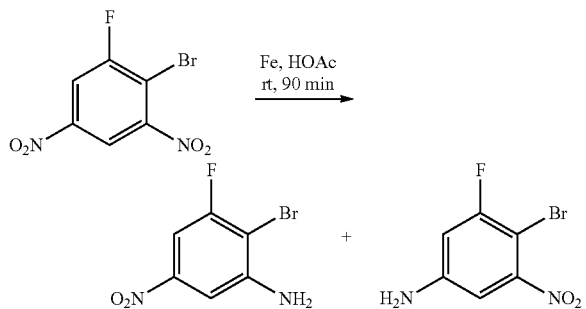

A mixture of 2-bromo-1,5-dinitro-3-fluorobenzene (100 mg, 0.38 mmol, 1 equiv) and iron powder (64 mg, 1.14 mmol, 3 equiv) in 3 mL of HOAc was stirred at room temperature for 90 minutes. The reaction mixture was diluted with EtOAc (20 mL) and saturated NaHCO$_3$ (to ca. pH 7-8). The organic layer was separated and evaporated under vacuum. The crude residue was purified by column chromatography on silica gel using EtOAc/hexanes (1:4) as eluent to give 47 mg of 2-bromo-3-fluoro-5-nitroaniline (52%).

$^1$H NMR (CDCl$_3$, 300 MHz): δ 7.43-7.32 (m, 2H), 4.63 (br. s, 2H), 1.40-1.35 (m, 1H), 1.25-1.20 (m, 2H), 0.85-0.80 (m, 2H); m/z=235 (M$^+$)$^+$.

A later fraction gave 28 mg of 4-bromo-3-fluoro-5-nitroaniline (31%).

$^1$H NMR (CDCl$_3$, 300 MHz): δ 6.94 (d, J=2.7 Hz, 1H), 6.62 (dd, J=9.6, 2.7 Hz, 1H), 4.15 (br. s, 2H), 1.40-1.35 (m, 1H), 1.28-1.23 (m, 2H), 0.88-0.85 (m, 2H); m/z=237 (M+2H).

Example 24

Synthesis of 2-cyclopropyl-3-fluoro-5-nitroaniline

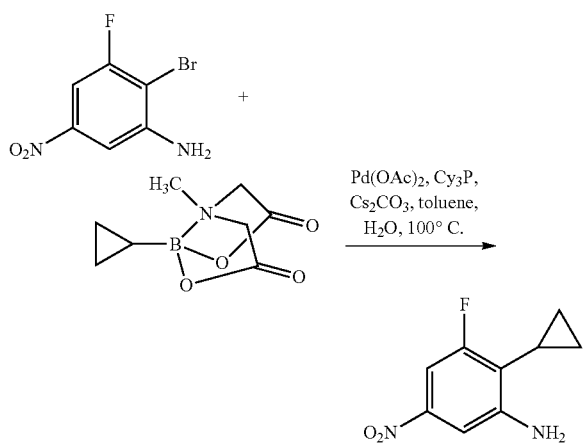

A mixture of 2-bromo-3-fluoro-5-nitroaniline (1.6 g, 6.81 mmol, 1 equiv), cyclopropylboronic acid MIDA ester (Aldrich; 4.0 g, 20.43 mmol, 3 equiv), Pd(OAc)$_2$ (238 mg, 1.06 mmol, 0.15 equiv), Cy$_3$P (578 mg, 2.06 mmol, 0.3 equiv) and Cs$_2$CO$_3$ (13.26 g, 40.8 mmol, 6 equiv) in toluene (70 mL) and H$_2$O (14 mL) was de-gassed with N$_2$ for 5 minutes. The mixture was then heated at 100° C. (oil bath temperature) overnight. After allowing to cool to room temperature, the mixture was diluted with EtOAc (100 mL) and H$_2$O (50 mL) and the mixture filtered through Celite. The filter cake was washed with EtOAc (2×50 mL) and the filtrate partitioned. The organic layer was evaporated under vacuum to leave a crude residue which was purified by column chromatography on silica gel using EtOAc/hexanes (1:4) as eluent to give the product (1.2 g, 90%) as a dark yellow solid.

$^1$H NMR (CDCl$_3$, 300 MHz): δ 7.29-7.21 (m, 2H), 4.44 (br. s, 2H), 1.52-1.42 (m, 1H), 1.11-1.05 (m, 2H), 0.73-0.67 (m, 2H); m/z=197 (M+H)$^+$

Example 25

Synthesis of 1-(2-cyclopropyl-3-fluoro-5-nitrophenyl)-1H-tetrazole

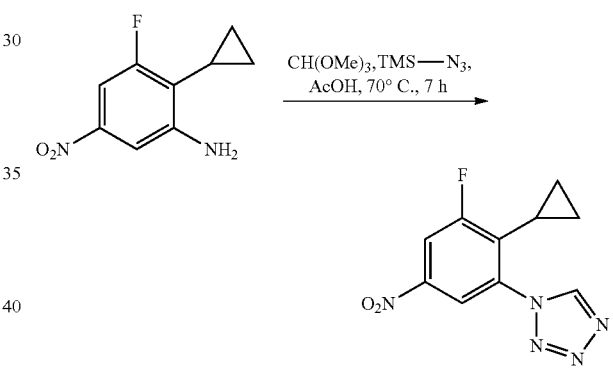

N.b.: TMS-N$_3$ and tetrazole product are potentially explosive. Use a blast shield for this reaction and glassware with no scratches, cracks, etc. Avoid contact with metals, including metal spatulas. Keep the product slightly wet with residual solvent from the column.

A mixture of 2-cyclopropyl-3-fluoro-5-nitroaniline (300 mg, 1.53 mmol, 1 equiv), trimethylsilyl azide (1.0 mL, 7.65 mmol, 5 equiv), trimethylorthoformate (1.67 mL, 15.29 mmol, 10 equiv) in AcOH (3 mL) was heated to 70° C. and stirred for 7 hours behind a blast shield. After allowing to cool to room temperature, the mixture was further cooled in ice-water and basified to ca. pH 12-14 with 1N NaOH and diluted with EtOAc. The aqueous and organic layers were partitioned and the aqueous extracted with EtOAc (2×150 mL). The combined organic extracts were washed with 1N NaOH (1×100 mL), dried (Na$_2$SO$_4$), filtered, and the solvent removed under vacuum—silica gel was added at this stage so that the crude product was absorbed directly on to silica gel. The crude product was purified by column chromatography on silica gel using EtOAc/hexanes (30-50% EtOAc in increments of 10% EtOAc) to give the product 1-(2-cyclopropyl-3-fluoro-5-nitrophenyl)-1H-tetrazole (343 mg, 90%) as a white solid.

$^1$H NMR (DMSO d$_6$, 300 MHz): δ 9.96 (br. s, 1H), 8.38-8.44 (m, 2H), 1.79-1.88 (m, 1H), 0.757-0.821 (m, 2H), 0.375-0.428 (m, 2H); LCMS (m/z): 250 (MH$^+$).

Example 26

Synthesis of 4-cyclopropyl-3-fluoro-5-(1H-tetrazol-1-yl)benzenamine

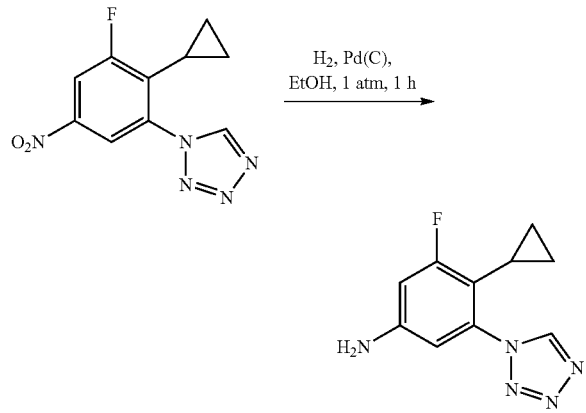

A round-bottom flask was charged with 1-(2-cyclopropyl-3-fluoro-5-nitrophenyl)-1H-tetrazole (288 mg, 1.16 mmol), EtOH (12 mL), and 10% Pd/C (50% in water, Degussa type E101; 246 mg, 85% by weight of the starting nitro compound) giving a suspension. The flask was sealed with a rubber septum, degassed, and back-filled with H$_2$ (×3) from a balloon filled with H$_2$. The reaction was stirred for 1 hour using a H$_2$ filled balloon. LCMS analysis indicated 4% cleavage of the cyclopropyl moiety to the isopropyl. The reaction mixture was filtered through a pad of Celite, and the pad of Celite was rinsed with DCM/MeOH (1:9, 100 mL). The filtrate was evaporated to dryness—silica gel was added at this stage so that the crude product was absorbed directly on to silica gel. The crude product was purified by column chromatography on silica gel using EtOAc/hexanes (50-60% EtOAc in increments of 10% EtOAc) to give the product, 4-cyclopropyl-3-fluoro-5-(1H-tetrazol-1-yl)benzenamine (234 mg, 92%) as a light-brown solid.

$^1$H NMR (DMSO d$_6$, 300 MHz): δ 9.81 (br. s, 1H), 6.49-6.54 (m, 2H), 5.78 (br. s, 2H), 1.51-1.60 (m, 1H), 0.50-0.55 (m, 2H), 0.00-0.04 (m, 2H); LCMS (m/z): 220 (MH$^+$).

Example 27

Synthesis of 4-(2,2,6,6-tetramethylpiperidin-4-ylamino)-2-(4-cyclopropyl-3-fluoro-5-(1H-tetrazol-1-yl)phenylamino)pyrimidine-5-carbonitrile

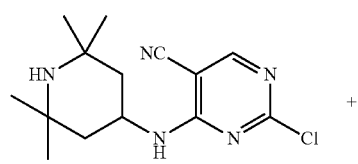

+

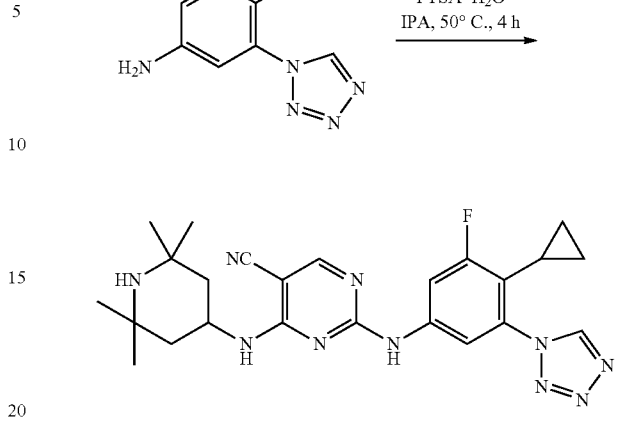

A mixture of 4-(2,2,6,6-tetramethylpiperidin-4-ylamino)-2-chloropyrimidine-5-carbonitrile (72 mg, 0.243 mmol, 1 equiv), 4-cyclopropyl-3-fluoro-5-(1H-tetrazol-1-yl)benzenamine (64 mg, 0.292 mmol, 1.2 equiv), and PTSA monohydrate (37 mg, 0.195 mmol, 0.8 equiv) in IPA (2.5 mL) were heated to 50° C. for 4 hours. After cooling to ambient temperature, the crude mixture was quenched with 2M NH$_3$/MeOH followed by concentrating to dryness and repeating once. The crude product was purified by flash chromatography and eluted with DCM:2M NH$_3$/MeOH=100:0 to 96:4 using 1% 2M NH$_3$/MeOH increments to provide the desired product which was recrystallized with IPA/hexane to give desired compound (61 mg, 53%) as a solid.

$^1$H NMR (DMSO d$_6$, 300 MHz): δ 10.12 (br. s, 1H), 9.80-9.90 (m, 1H), 8.22-8.33 (m, 1H), 7.90-7.94 (m, 1H), 7.43-7.50 (m, 2H), 4.40 (br. s, 1H), 1.51-1.61 (m, 3H), 0.93-1.22 (m, 15H), 0.53-0.55 (m, 2H), 0.37-0.39 (m, 2H); LCMS (m/z): 477 (MH$^+$).

Example 28

Synthesis of N2-(4-cyclopropyl-3-fluoro-5-(1H-tetrazol-1-yl)phenyl)-5-fluoro-N4-(2,2,6,6-tetramethylpiperidin-4-yl)pyrimidine-2,4-diamine

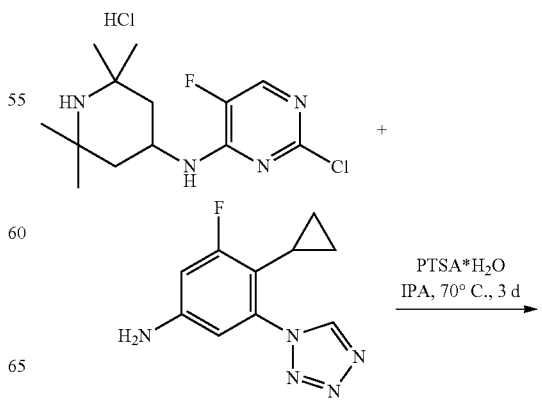

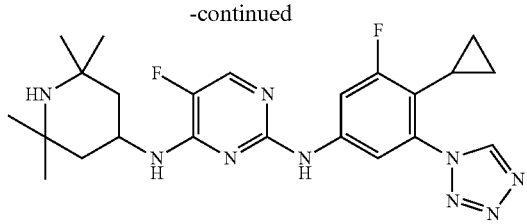

A mixture of 2-chloro-5-fluoro-N-(2,2,6,6-tetramethylpiperidin-4-yl)pyrimidin-4-amine hydrochloride (72 mg, 0.190 mmol, 1 equiv), 4-cyclopropyl-3-fluoro-5-(1H-tetrazol-1-yl)benzenamine (50 mg, 0.228 mmol, 1.2 equiv), and PTSA monohydrate (30 mg, 0.152 mmol, 0.8 equiv) in IPA (2 mL) were heated to 70° C. for 3 days. LCMS indicated 2-4% of the cleaved tetrazole product. After cooling to ambient temperature, the crude mixture was quenched with 2M $NH_3$/MeOH followed by concentrating to dryness and repeating once. The crude product was purified by flash chromatography and eluted with DCM:2M $NH_3$/MeOH=100:0 to 96:4 using 1% 2M $NH_3$/MeOH increments to provide the desired product which was recrystallized with IPA/hexane to give desired compound (58 mg, 65%) as a solid.

$^1$H NMR (DMSO $d_6$, 300 MHz): δ 9.86 (br. s, 1H), 9.48 (br. s, 1H), 7.91-7.95 (m, 1H), 7.82-7.86 (m, 1H), 7.48 (br. s, 1H), 7.26-7.30 (m, 1H), 4.26-4.32 (m, 1H), 1.54-1.62 (m, 4H), 0.94-1.13 (m, 14H), 0.51-0.41 (m, 2H), 0.11-0.12 (m, 2H); LCMS (m/z): 470 (MH$^+$).

Example 29

Synthesis of 1-bromo-2-fluoro-3,5-dinitrobenzene

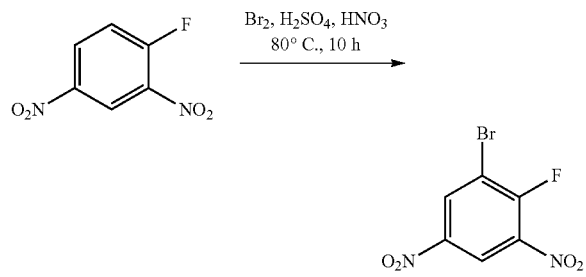

To 1-fluoro-2,4-dinitrobenzene (13.0 g, 69.85 mmol, 1 equiv) dissolved in sulfuric acid (190 mL) at room temperature was added bromine (4.30 mL, 83.82 mmol, 1.2 equiv) dropwise followed by the slow dropwise addition of nitric acid (70%, d=1.500; 3.25 mL, 76.84 mmol, 1.1 equiv). The reaction vessel was fitted with a refluxing condenser, and the reaction mixture was heated at 80° C. for 10 hours. LCMS indicated a reactant:product ratio of 1:1. After allowing to cool to room temperature, the mixture was poured into ice and diluted with DCM. The aqueous and organic layers were partitioned, and the aqueous extracted with DCM (2×300 mL). The combined organic extracts were washed with saturated $Na_2S_2O_3$ (2×200 mL), dried ($Na_2SO_4$), filtered, and concentrated to dryness. The crude product was purified using a pad of silica gel and eluted with EtOAc/hexanes (25-35% EtOAc in increments of 5% EtOAc) to give the product 1-bromo-2-fluoro-3,5-dinitrobenzene (5.55 g, 30%) as a light-yellow solid.

$^1$H NMR (DMSO $d_6$, 300 MHz): δ 8.96-9.02 (m, 1H), 8.82-8.89 (m, 1H); LCMS (m/z): 266 (MH$^+$).

Example 30

Synthesis of 3-bromo-2-fluoro-5-nitrobenzenamine

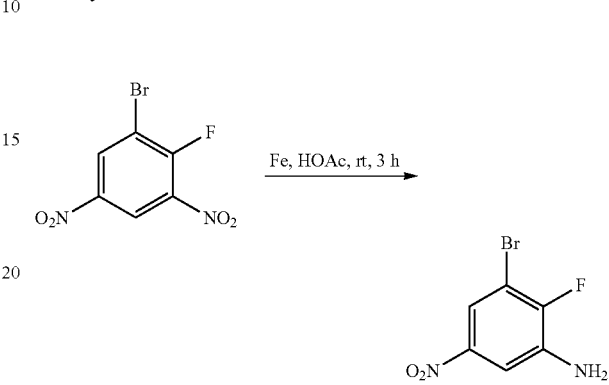

To a solution of 1-bromo-2-fluoro-3,5-dinitrobenzene (5.4 g, 20.38 mmol, 1 equiv) in acetic acid (200 mL) at room temperature (using a water bath) was added powdered iron portion-wise (5.70 g, 102 mmol, 5 equiv). The resulting solution was stirred for 3 hours keeping the temperature of the mixture below 30° C. LCMS indicated the formation of three products: 3-bromo-2-fluoro-5-nitrobenzenamine-F3 (86%), 3-bromo-4-fluoro-5-nitrobenzenamine-F2 (5%), and 5-bromo-4-fluorobenzene-1,3-diamine-F1 (9%). [Note: After completion of this experiment, to identify regioisomers, 3-bromo-2-fluoro-5-nitrobenzenamine was diazotized and deaminated (see, E. S. Adams and K. L. Rinehart. The Journal of Antibiotics 1994, 47 (12), 1456-1465) to give 3-bromo-4-fluoro-nitrobenzene. This was compared to an authentic sample obtained from a commercial source]. DCM was added to the mixture, and the resulting mixture was filtered through a pad of Celite, and the pad of Celite was rinsed with MeOH. The filtrate was evaporated to dryness. The residue was quenched with 2M $NH_3$/MeOH followed by concentrating to dryness and repeating once—silica gel was added at this stage so that the crude product was absorbed directly on to silica gel. The crude product was purified by column chromatography on silica gel using DCM to give the desired product 3-bromo-2-fluoro-5-nitrobenzenamine (F1 on TLC; 1.87 g, 39%) as a yellow solid.

$^1$H NMR (DMSO $d_6$, 300 MHz): δ 7.55-7.60 (m, 2H), 6.19 (bs, 2H); $^{19}$F NMR (DMSO $d_6$, 282 MHz): δ −120 (s, 1F); LCMS (m/z): 236 (MH$^+$).

Further elution with DCM provided 3-bromo-4-fluoro-5-nitrobenzenamine (F2 on TLC). $^1$H NMR (DMSO $d_6$, 300 MHz): δ 7.13-7.22 (m, 2H), 5.84 (br. s, 2H); $^{19}$F NMR (DMSO $d_6$, 282 MHz): δ −132 (s, 1F); LCMS (m/z): 236 (MH$^+$).

Further elution with DCM gave 5-bromo-4-fluorobenzene-1,3-diamine (F3 on TLC). $^1$H NMR (DMSO $d_6$, 300 MHz): δ 5.89-5.95 (m, 2H), 5.07 (br. s, 2H), 4.84 (br. s, 2H); $^{19}$F NMR (DMSO $d_6$, 282 MHz): δ −146 (s, 1F); LCMS (m/z): 206 (MH$^+$).

Example 31

Synthesis of 3-cyclopropyl-2-fluoro-5-nitroaniline

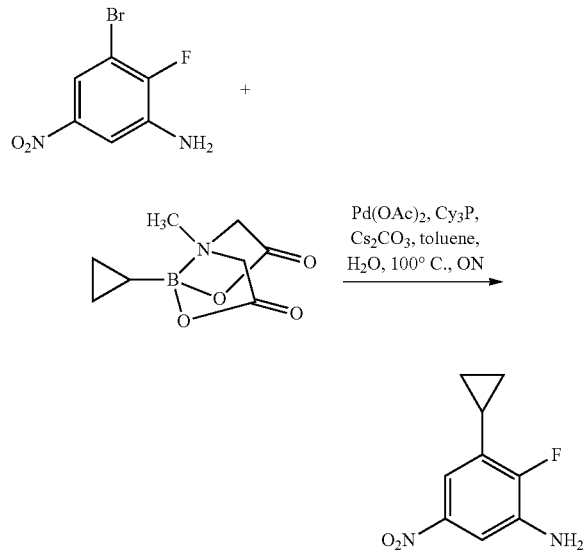

A mixture of 3-bromo-2-fluoro-5-nitroaniline (2.20 g, 9.36 mmol, 1 equiv), cyclopropylboronic acid MIDA ester (Aldrich; 11.07 g, 56.17 mmol, 6 equiv), Cy$_3$P (1.05 g, 3.74 mmol, 0.4 equiv), Cs$_2$CO$_3$ (54.90 g, 168.50 mmol, 18 equiv) in toluene/H$_2$O (5:1; 450 mL:90 mL) followed by Pd(OAc)$_2$ (0.420 g, 1.87 mmol. 0.20 equiv) was de-gassed by sonicating under vacuum for 10 minutes and back-filled with N$_2$. The mixture was then heated at 100° C. overnight. After allowing to cool to room temperature, the mixture was concentrated to dryness. The residue was taken in DCM, and silica gel was added at this stage so that the residue was absorbed directly on to silica gel. After removing the solvent under vacuum, the crude product was purified by column chromatography on silica gel using DCM to give the product 3-cyclopropyl-2-fluoro-5-nitroaniline (1.27 g, 69%) as a yellow solid.

$^1$H NMR (DMSO d$_6$, 300 MHz): δ 7.38-7.42 (m, 1H), 6.90 (dd, J=2.7, 5.7 Hz, 1H), 5.80 (br. s, 2H), 2.00-2.09 (m, 1H), 0.95-1.01 (m, 2H), 0.71-0.76 (m, 2H); LCMS (m/z): 197 (MH$^+$).

Example 32

Synthesis of 1-(3-cyclopropyl-2-fluoro-5-nitrophenyl)-1H-tetrazole

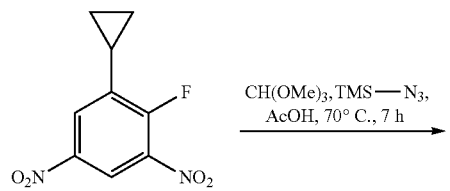

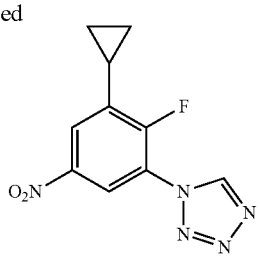

N.b.: TMS-N$_3$ and tetrazole product are potentially explosive. Use a blast shield for this reaction and glassware with no scratches, cracks, etc. Avoid contact with metals, including metal spatulas. Keep the product slightly wet with residual solvent from the column.

A mixture of 3-cyclopropyl-2-fluoro-5-nitroaniline (1.27 g, 6.47 mmol, 1 equiv), trimethylsilyl azide (4.26 mL, 32.37 mmol, 5 equiv), trimethylorthoformate (7.09 mL, 67.74 mmol, 10 equiv) in AcOH (15 mL) was heated to 70° C. and stirred for 7 hours behind a blast shield. After allowing to cool to room temperature, the mixture was further cooled in ice-water and basified to ca. pH 12-14 with 1N NaOH and diluted with EtOAc. The aqueous and organic layers were partitioned and the aqueous extracted with EtOAc (2×200 mL). The combined organic extracts were washed with 1N NaOH (1×200 mL), dried (Na$_2$SO$_4$), filtered, and the solvent removed under vacuum—silica gel was added at this stage so that the crude product was absorbed directly on to silica gel. The crude product was purified by column chromatography on silica gel using EtOAc/hexanes (30-50% EtOAc in increments of 10% EtOAc) to give the product 1-(3-cyclopropyl-2-fluoro-5-nitrophenyl)-1H-tetrazole (1.49 g, 92%) as a light-yellow solid.

$^1$H NMR (DMSO d$_6$, 300 MHz): δ 10.01 (s, 1H), 8.58 (dd, J=2.70 Hz, 5.70 Hz, 1H), 8.02 (dd, J=3.0, 6.3 Hz, 1H), 2.19-2.28 (m, 1H), 1.09-1.17 (m, 2H), 0.97-1.03 (m, 2H); LCMS (m/z): 250 (MH$^+$).

Example 33

Synthesis of 3-cyclopropyl-4-fluoro-5-(1H-tetrazol-1-yl)benzenamine

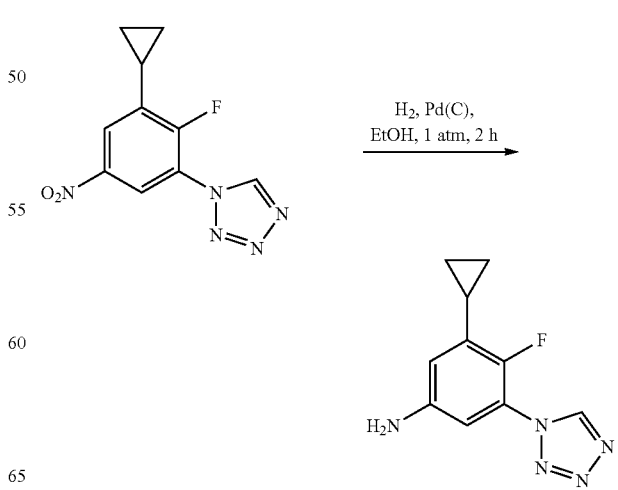

A round-bottom flask was charged with 1-(3-cyclopropyl-2-fluoro-5-nitrophenyl)-1H-tetrazole (1.41 g, 5.65 mmol), EtOH (50 mL), and 10% Pd/C (50% in water, Degussa type E101; 1.20 g, 85% by weight of the starting nitro compound) giving a suspension. The flask was sealed with a rubber septum, degassed, and back-filled with $H_2$ (×3) from a balloon filled with $H_2$. The reaction was stirred for 2 hours using a $H_2$ filled balloon. LCMS analysis indicated 4% cleavage of the cyclopropyl moiety to the isopropyl. The reaction mixture was filtered through a pad of Celite, and the pad of Celite was rinsed with DCM/MeOH (1:9, 300 mL). The filtrate was evaporated to dryness—silica gel was added at this stage so that the crude product was absorbed directly on to silica gel. The crude product was purified by column chromatography on silica gel using EtOAc/hexanes (50-60% EtOAc in increments of 10% EtOAc) to give the product, 3-cyclopropyl-4-fluoro-5-(1H-tetrazol-1-yl)benzenamine (1.0 g, 81%) as a reddish-brown solid.

$^1$H NMR (DMSO $d_6$, 300 MHz): δ 9.84 (br. s, 1H), 6.66-6.69 (m, 1H), 6.31-6.33 (m, 1H), 5.34 (br. s, 2H), 1.97-2.05 (m, 1H), 0.95-1.01 (m, 2H), 0.66-0.69 (m, 2H); LCMS (m/z): 220 (MH$^+$).

Example 34

Synthesis of 4-(2,2,6,6-tetramethylpiperidin-4-ylamino)-2-(3-cyclopropyl-4-fluoro-5-(1H-tetrazol-1-yl)phenylamino)pyrimidine-5-carbonitrile

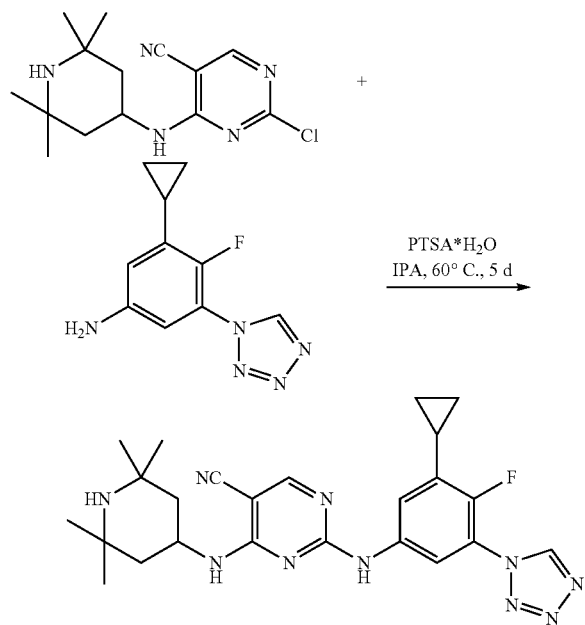

A mixture of 4-(2,2,6,6-tetramethylpiperidin-4-ylamino)-2-chloropyrimidine-5-carbonitrile (112 mg, 0.380 mmol, 1 equiv), 3-cyclopropyl-4-fluoro-5-(1H-tetrazol-1-yl)benzenamine (100 mg, 0.456 mmol, 1.2 equiv), and PTSA monohydrate (58 mg, 0.304 mmol, 0.8 equiv) in IPA (4 mL) were heated to 60° C. for 5 days. After cooling to ambient temperature, the crude mixture was concentrated to dryness. The residue was taken in ice-cold water and EtOAc then adjusted to ca. pH 12-14 with 1N NaOH. The aqueous and organic layers were partitioned, and the aqueous layer was extracted with EtOAc (1×150 mL). The combined organic extracts were dried (Na$_2$SO$_4$), filtered, and the solvent removed under vacuum. The crude product was submitted to the analytical department for purification by reverse-phase HPLC using 0.1% formic acid as a modifier in water and acetonitrile (compound unstable in TFA). The product as the formate salt was taken in ice-cold water and EtOAc then adjusted to ca. pH 12-14 with 1N NaOH. The aqueous and organic layers were partitioned, and the aqueous layer was extracted with EtOAc (2×150 mL). The combined organic extracts were dried (Na$_2$SO$_4$), filtered, and concentrated to give desired compound (63 mg, 35%) as a solid.

$^1$H NMR (DMSO $d_6$, 300 MHz): δ 9.94 (s, 1H), 9.80 (br. s, 1H), 8.34 (s, 1H), 8.00-8.11 (m, 1H), 7.35 (d, 1H, J=8.1 Hz), 7.22 (br. s, 1H), 4.29 (br. s, 1H), 2.01-2.11 (m, 1H), 1.48-1.52 (m, 2H), 0.75-1.19 (m, 17H); LCMS (m/z): 477 (MH$^+$).

Example 35

Synthesis of N2-(3-cyclopropyl-4-fluoro-5-(1H-tetrazol-1-yl)phenyl)-5-fluoro-N4-(2,2,6,6-tetramethylpiperidin-4-yl)pyrimidine-2,4-diamine

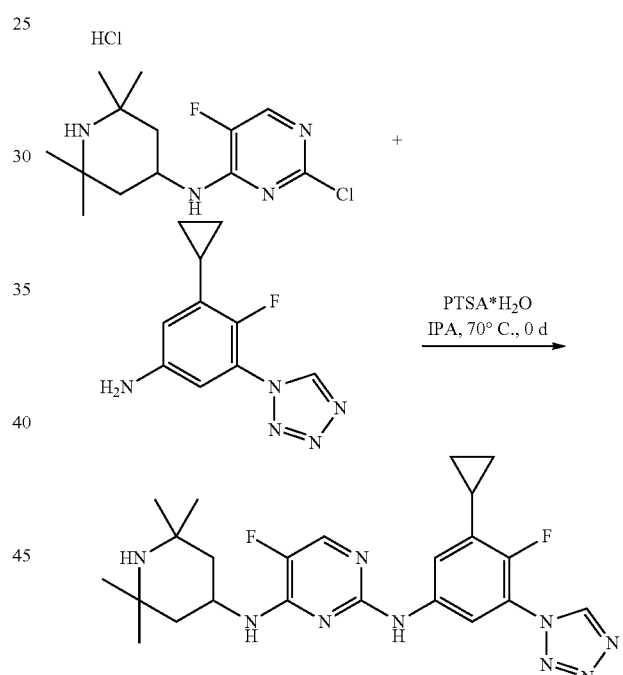

A mixture of 2-chloro-5-fluoro-N-(2,2,6,6-tetramethylpiperidin-4-yl)pyrimidin-4-amine hydrochloride (246 mg, 0.760 mmol, 1 equiv), 3-cyclopropyl-4-fluoro-5-(1H-tetrazol-1-yl)benzenamine (200 mg, 0.912 mmol, 1.2 equiv), and PTSA monohydrate (116 mg, 0.608 mmol, 0.8 equiv) in IPA (8 mL) were heated to 70° C. for 3 days. LCMS indicated 2-4% of the cleaved tetrazole product. After cooling to ambient temperature, the crude mixture was quenched with 2M NH$_3$/MeOH followed by concentrating to dryness and repeating twice. The crude product was purified by flash chromatography and eluted with DCM:2M NH$_3$/MeOH=100:0 to 96:4 using 1% 2M NH$_3$/MeOH increments to provide the desired product which was recrystallized with IPA/hexane to give desired compound (154 mg, 43%) as a solid.

$^1$H NMR (DMSO $d_6$, 300 MHz): δ 9.92 (br. s, 1H), 9.16 (br. s, 1H), 8.11-8.15 (m, 1H), 7.86-7.91 (m, 1H), 7.52 (d, 1H,

J=7.5 Hz), 7.16-7.21 (m, 1H), 4.26-4.32 (m, 1H), 1.94-2.06 (m, 1H), 1.73-1.81 (m, 2H), 1.47-1.58 (m, 2H), 0.99-1.30 (m, 15H), 0.69-0.70 (m, 2H); LCMS (m/z): 470 (MH$^+$).

Example 36

Synthesis of 4-fluoro-5-nitro-2-(prop-1-en-2-yl)benzenamine

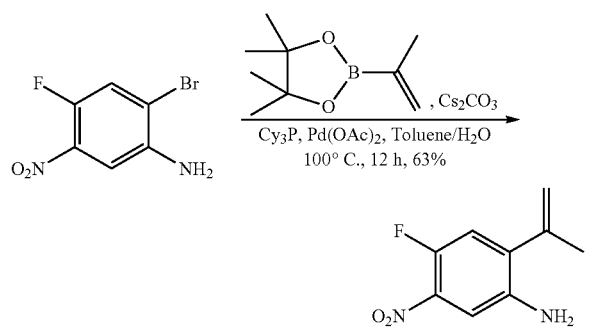

A mixture of 2-bromo-4-fluoro-5-nitroaniline (2.85 g, 12.13 mmol, 1.0 eq), isopropenylboronic acid pinacol ester (5.09 g, 30.33 mmol, 2.5 eq), Pd(OAc)$_2$ (0.82 g, 3.64 mmol, 0.3 eq), Cy$_3$P (1.70 g, 6.07 mmol, 0.5 eq) and Cs$_2$CO$_3$ (39.51 g, 121.28 mmol, 10 eq) in toluene (100 mL) and H$_2$O (25 mL) was de-gassed with N$_2$ for 15 minutes. The mixture was then heated at 100° C. (oil bath temperature). After allowing to cool to room temperature, the mixture was diluted with EtOAc (100 mL) and H$_2$O (50 mL) and the mixture filtered through celite. The filter cake was washed with EtOAc (2×50 mL) and the filtrate partitioned. The organic layer was dried (Na$_2$SO$_4$), filtered and the solvent removed under vacuum to leave a crude residue. The residue was purified by column chromatography on silica gel (residue dry-loaded on to silica gel) using EtOAc/hexanes (1:5 gradient) as eluent to give the product (1.59 g, 64%) as a dark brown solid.

$^1$H NMR (DMSO-d$_6$, 300 MHz): δ 7.35 (d, 1H), 7.10 (d, 1H), 5.32 (br. s, 3H), 5.09 (s, 1H), 1.99 (s, 3H); m/z=197.0 (M$^+$)$^+$.

Example 37

Synthesis of 2-fluoro-4-isopropyl-5-(1H-tetrazol-1-yl)benzenamine

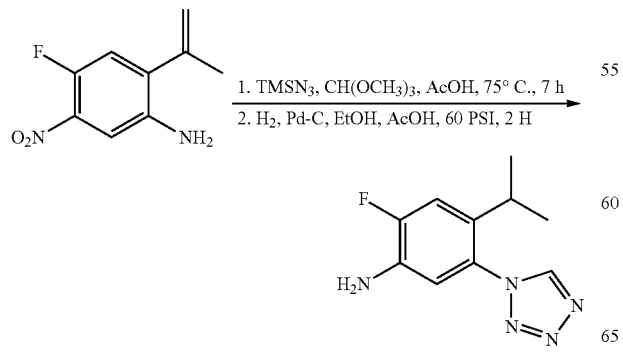

Step 1: 1-(4-fluoro-5-nitro-2-(prop-1-en-2-yl)phenyl)-1H-tetrazole

N.b.: TMS-N$_3$ and tetrazole product are potentially explosive. Use a blast shield for this reaction and glassware with no scratches, cracks, etc. Avoid contact with metals, including metal spatulas. Keep the product slightly wet with residual solvent from the column.

A mixture of 2-isoPropenyl-4-fluoro-5-nitroaniline (1.32 g, 6.70 mmol, 1.0 eq), trimethylsilyl azide (3.90 g, 33.50 mmol, 5.0 eq), trimethylorthoformate (7.11 g, 67 mmol, 10 eq) in AcOH (10 mL) was heated to 75° C. and stirred overnight behind a blast shield. After allowing the reaction mixture to cool to room temperature, the mixture was concentrated under vacuum behind a blast shield. The crude reaction mixture was neutralized using 3N NaOH (30 mL) in ice bath. The tan precipitate formed was filtered and dried under vacuum. The crude product was taken to the next step without further purification. m/z=250.

Step 2: 2-fluoro-4-isopropyl-5-(1H-tetrazol-1-yl)benzenamine

A Parr vessel was charged with 1-(2-isopropenyl-4-fluoro-5-nitrophenyl)-1H-tetrazole (0.100 g, 4.0 mmol), EtOH (25 mL), AcOH (1 mL), and 10% Pd/C (50% in water, Degussa type E101; 0.050 g, 50% by weight of the starting nitro compound) giving a suspension. The vessel was sealed, degassed, and back-filled with H$_2$ (×3). The vessel was then charged with 60 psi H$_2$ and allowed to shake until LCMS analysis indicated complete conversion. The reaction mixture was filtered through a pad of Celite, and the pad of Celite was rinsed with DCM/MeOH (1:9, 50 mL). The filtrate was evaporated to dryness. The crude product was purified by column chromatography on silica gel using EtOAc/hexanes (25-50% EtOAc in increments of 5% EtOAc) to give the product, 4-isopropyl-2-fluoro-5-(1H-tetrazol-1-yl)benzenamine (0.075 g, 85%) as a brown solid.

$^1$H NMR (CDCl$_3$, 300 MHz): δ 8.70 (s, 1H), 7.06 (d, 1H, J=12.1 Hz), 6.66 (d, 1H, J=8.0 Hz), 3.95 (br. s, 2H), 2.39 (m, 1H), 1.11 (s, 3H), 1.08 (s, 3H); m/z=222 (M+H)$^+$.

Example 38

Synthesis of 4-(2,2,6,6-tetramethylpiperidin-4-ylamino)-2-(2-fluoro-4-isopropyl-5-(1H-tetrazol-1-yl)phenylamino)pyrimidine-5-carbonitrile

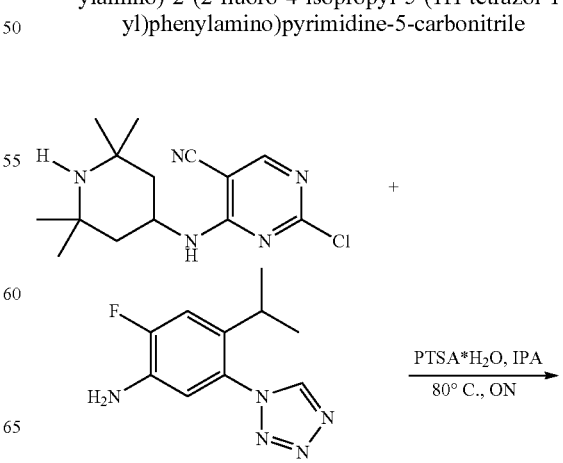

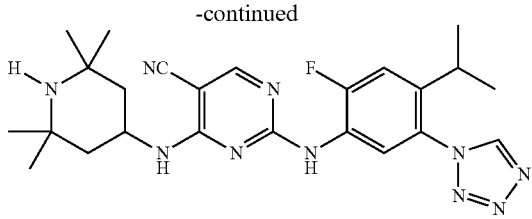

A mixture of 2-chloro-5-cyano-N-(2,2,6,6-tetramethylpiperidin-4-yl)pyrimidin-4-amine (0.05 g, 0.17 mmol, 1 equiv), 4-isopropyl-2-fluoro-5-(1H-tetrazol-1-yl)benzenamine (0.045 g, 0.204 mmol, 1.2 equiv), and para-toluenesulfonic acid monohydrate (0.025 g, 0.136 mmol, 0.8 equiv) in IPA (5 mL) were heated to 80° C. overnight. LCMS indicated desired product plus approximately 10% of 5-fluoro-2-isopropoxy-N-(2,2,6,6-tetramethylpiperidin-4-yl)pyrimidin-4-amine byproduct. After cooling to ambient temperature, the crude mixture was quenched with 2M $NH_3$/MeOH followed by concentrating to dryness and repeating once. The crude product was purified by flash chromatography and eluted with DCM:2M $NH_3$/MeOH (100:0 to 95:5 using 1% 2M $NH_3$/MeOH increments) to provide the desired product which was recrystallized with DCM/IPA to give the title compound (45 mg, 55%) as a solid.

$^1$H NMR (DMSO $d_6$, 300 MHz): δ 9.77 (s, 1H), 9.53 (br. s, 1H), 8.27 (s, 1H), 7.56 (d, J=6.9 Hz, 1H), 7.45 (d, J=11.8 Hz, 1H), 7.37 (d, J=8.0 Hz, 1H), 4.30 (br. s, 1H), 2.34 (m, 1H), 1.45-1.48 (m, 2H), 1.11-1.17 (m, 2H), 1.09 (s, 6H), 1.06 (s, 3H), 0.95 (s, 6H), 0.90 (s, 3H); m/z=479 (M+H)$^+$.

Example 39

Synthesis of 2-cyclopropyl 5-nitrobenzenamine

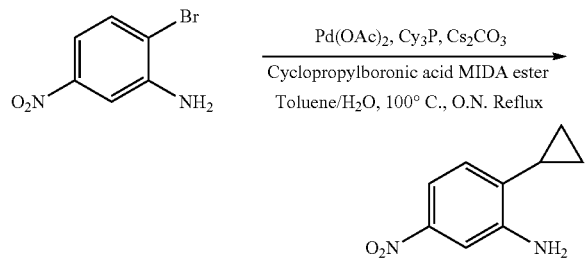

In a 250 mL round bottom flask to a solution of 2-bromo 5-nitroaniline (2.30 g, 10.60 mmol) in toluene (90 mL) tricyclohexylphosphine (0.89 g, 3.18 mmol), $Cs_2CO_3$ (17.22 g, 52.99 mmol), cyclopropylboronic acid MIDA ester (2.92 g, 14.84 mmol) and 10 ml de-ionized water were added and the solution was degassed with nitrogen for 30 minutes. To the above solution Pd(OAc)$_2$ (0.36 g, 1.59 mmol) was added under nitrogen and the reaction mixture was refluxed for 12 hours. LC MS analysis of the crude reaction indicated the completion of the reaction. The crude reaction mixture was filtered on Celite pad and the volatiles were removed under reduced pressure. The dark brown oil was worked-up with 2×100 mL ethyl acetate and water (100 mL), dried on MgSO$_4$ and ethyl acetate was evaporated under reduced pressure. The crude reaction mixture was separated by column chromatography to give 2-cyclopropyl-5-nitrobenzeneamine in 70% yield.

$^1$H NMR (DMSO $d_6$, 300 MHz): δ 7.43 (d, J=2.5 Hz, 1H), 7.26 (dd, J=1.9, 8.3 Hz, 1H), 6.95 (d, J=8.3 Hz, 1H), 5.70 (s, 2H), 1.75 (m, 1H), 0.92-0.95 (m, 2H), 0.56-0.59 (m, 2H); LCMS (m/z): 179 (MH$^+$).

Example 40

Synthesis of 1-(2-cyclopropyl-5-nitrophenyl)-5-(trifluoromethyl)-1H-tetrazole

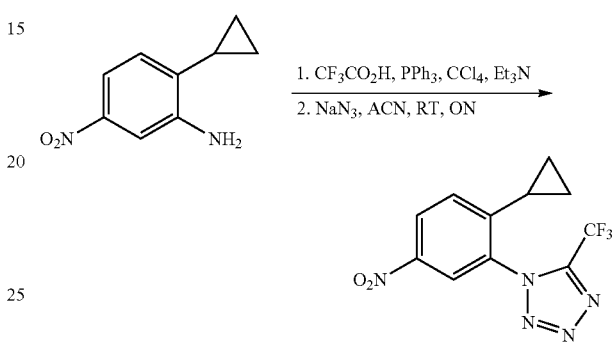

Step:1 (Z)—N-(1-chloro-2,2,2-trifluoroethylidene)-2-cyclopropyl-5-nitrobenzenamine A mixture of CF$_3$CO$_2$H (0.98 mL, 12.65 mmol, 0.9 eq), PPh$_3$ (9.21 g, 35.13 mmol, 2.5 eq) and Et$_3$N (1.96 mL, 14.05 mmol, 1.0 eq), in 25 mL CCl$_4$ was stirred at 0° C. for 10 minutes. 2-cyclopropyl-5-nitrobenzeneamine (2.50 g, 14.05 mmol, 1.0 eq) was then added to the reaction mixture and the mixture was heated to reflux for 12 hours. Solvent was removed under reduced pressure and the residue was purified by column chromatography, eluting with n-hexane:ethyl acetate (10:1), giving the (Z)—N-(1-chloro-2,2,2-trifluoroethylidene)-2-cyclopropyl-5-nitrobenzenamine intermediate in semi pure form as a light yellow solid. This compound was taken to the next step with out further purification.

Step 2: 1-(2-cyclopropyl-5-nitrophenyl)-5-(trifluoromethyl)-1H-tetrazole

A mixture of NaN$_3$ (0.56 g, 8.57 mmol, 2.5 eq) and (Z)—N-(1-chloro-2,2,2-trifluoroethylidene)-2-cyclopropyl-5-nitrobenzenamine intermediate (1.0 g, 3.43 mmol, 1.0 eq) in 15 mL dry acetonitrile was stirred at room temperature for 16 hours. The reaction mixture was poured into ice-cold aqueous Na$_2$CO$_3$ solution, extracted with ethyl acetate. The organic layer washed with brine, dried over Na$_2$SO$_4$, filtered, and concentrated in vacuo. The resulting crude mixture was purified by column chromatography, eluting with n-hexane:ethyl acetate (10-50% EtOAc in increments of 10% EtOAc)), giving the desired product in 37% overall yield (1.55 g).

$^1$H NMR (DMSO $d_6$, 300 MHz): δ 8.45 (dd, 1H), 8.20 (d, 1H), 7.29 (d, 1H), 1.28 (m, 1H), 1.18 (m, 2H), 0.85 (m, 2H); m/z=300 (M+H)$^+$.

Example 41

Synthesis of 4-cyclopropyl-3-(5-(trifluoromethyl)-1H-tetrazol-1-yl)benzenamine

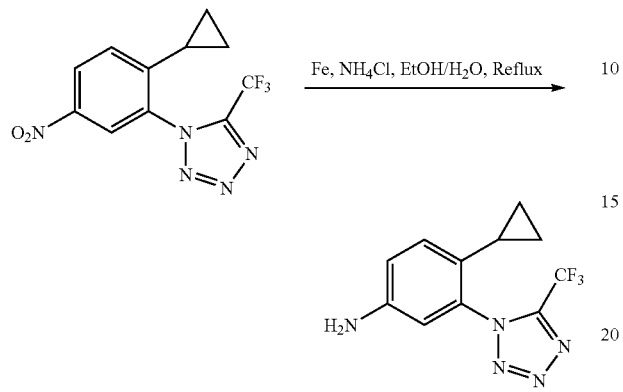

A mixture of nitro compound (0.25 g, 0.836 mmol, 1.0 eq), Fe (0.140 g, 2.51 mmol, 3.0 eq) and NH$_4$Cl (0.134 g, 2.51 mmol, 3.0 eq) in EtOH/H$_2$O (3:1) was refluxed for 1 hour. The reaction mixture was filtered on a celite pad and solvents were removed under reduced pressure. The crude reaction mixture was purified by column chromatography, eluting with n-hexane:ethyl acetate (10-70% EtOAc in increments of 10% EtOAc)), giving the required product in 78% yield (0.18 g).

$^1$H NMR (CDCl$_3$, 300 MHz): δ 6.99 (d, 1H), 6.83 (d, 1H), 6.55 (br. s, 1H), 1.25 (m, 1H), 0.65 (m, 2H), 0.49 (m, 2H); m/z=270 (M+H)$^+$.

Example 42

Synthesis of N2-(4-cyclopropyl-3-(5-(trifluoromethyl)-1H-tetrazol-1-yl)phenyl)-5-fluoro-N4-(2,2,6,6-tetramethylpiperidin-4-yl)pyrimidine-2,4-diamine

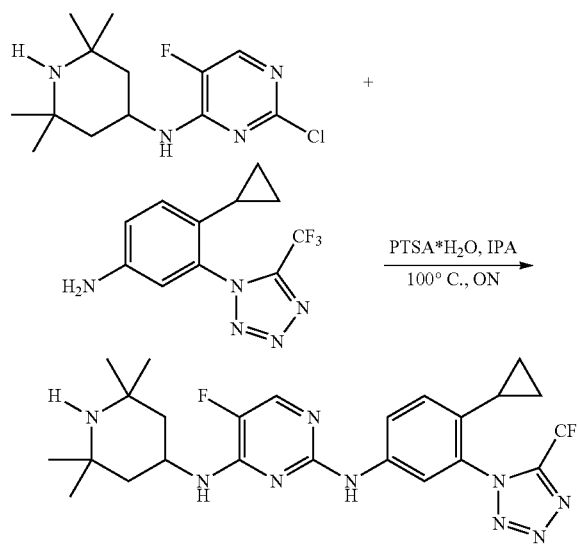

A mixture of 2-chloro-5-fluoro-N-(2,2,6,6-tetramethylpiperidin-4-yl)pyrimidin-4-amine hydrochloride (0.210 g, 0.65 mmol, 1 equiv), 4-cyclopropyl-5-(1-trifluoromethyl-tetrazol-1-yl)benzenamine (0.245 g, 0.910 mmol, 1.4 equiv), and para-toluenesulfonic acid monohydrate (0.099 g, 0.520 mmol, 0.8 equiv) in IPA (10 mL) were heated to 100° C. overnight. After cooling to ambient temperature, the crude mixture was quenched with 2M NH$_3$/MeOH followed by concentrating to dryness and repeating once. The crude product was purified by flash chromatography and eluted with DCM:2M NH$_3$/MeOH (100:0 to 95:5 using 1% 2M NH$_3$/MeOH increments) to provide the desired product which was recrystallized with DCM/IPA to give the title compound (0.18 g, 53% yield) as a solid.

$^1$H NMR (DMSO d$_6$, 300 MHz): δ 9.34 (s, 1H), 7.84-7.89 (m, 3H), 7.23 (d, J=8.0 Hz, 1H), 7.05 (d, J=9.1 Hz, 1H), 4.31 (br. m, 1H), 1.59-1.63 (m, 2H), 1.09-1.17 (m, 4H), 0.99 (s, 12H), 0.66-0.68 (m, 2H), 0.52-0.55 (m, 2H); m/z=520 (M+H)$^+$.

Example 43

Synthesis of N2-(4-cyclopropyl-2-fluoro-5-(1H-tetrazol-1-yl)phenyl)-5-fluoro-N4-1,2,2,6,6-pentamethylpiperidin-4-yl)pyrimidine-2,4-diamine

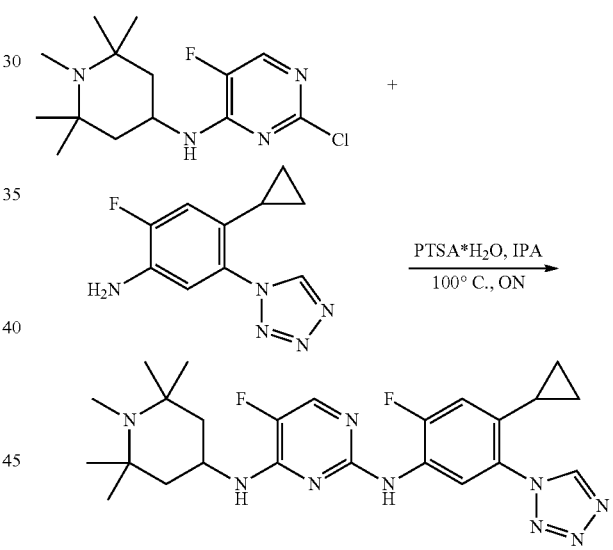

A mixture of 2-chloro-5-fluoro-N-(1,2,2,6,6-pentamethylpiperidin-4-yl)pyrimidin-4-amine hydrochloride (0.196 g, 0.58 mmol, 1 equiv), 4-cyclopropyl-2-fluoro-5-(1H-tetrazol-1-yl)benzenamine (0.140 g, 0.64 mmol, 1.1 equiv), and para-toluenesulfonic acid monohydrate (0.090 g, 0.47 mmol, 0.8 equiv) in IPA (15 mL) were heated to 100° C. overnight. After cooling to ambient temperature, the crude mixture was quenched with 2M NH$_3$/MeOH followed by concentrating to dryness and repeating once. The crude product was purified by flash chromatography and eluted with DCM:2M NH$_3$/MeOH (100:0 to 95:5 using 1% 2M NH$_3$/MeOH increments) to provide the desired product which was titurated with DCM/Hexane to give the title compound (0.100 g, in 36% yield) as a solid.

$^1$H NMR (DMSO d$_6$, 300 MHz): δ 9.84 (s, 1H), 8.60 (s, 1H), 7.89 (d, J=7.4 Hz, 1H), 7.82 (d, J=3.9 Hz, 1H), 7.21 (d, J=6.9 Hz, 1H), 7.08 (d, J=11.8 Hz, 1H), 4.11-4.15 (m, 1H), 2.10 (s, 3H), 1.50-1.57 (m, 2H), 1.30-1.44 (m, 3H), 1.01 (s, 6H), 0.76 (s, 6H), 0.71-0.73 (m, 2H), 0.55-0.57 (m, 2H); m/z=484 (M+H)+.

Example 44

Synthesis of 4-(1,2,2,6,6-pentamethylpiperidin-4-ylamino)-2-(4-cyclopropyl-2-fluoro-5-(1H-tetrazol-1-yl)phenylamino)pyrimidine-5-carbonitrile

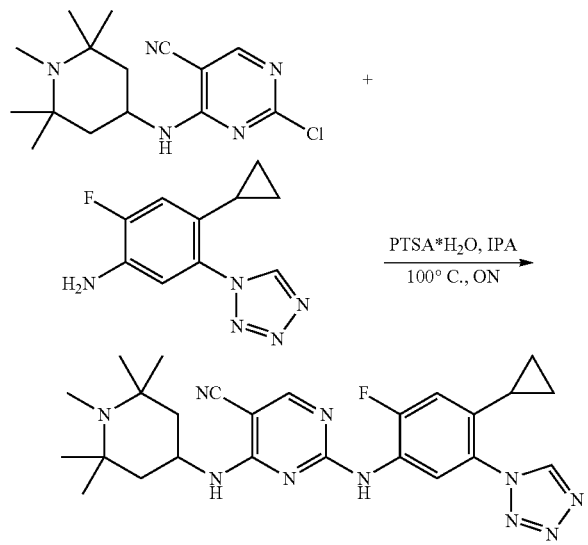

A mixture of 2-chloro-5-cyano-N-(1,2,2,6,6-pentamethylpiperidin-4-yl)pyrimidin-4-amine (0.205 g, 0.66 mmol, 1 equiv), 4-cyclopropyl-2-fluoro-5-(1H-tetrazol-1-yl)benzenamine (0.160 g, 0.730 mmol, 1.1 equiv), and para-toluenesulfonic acid monohydrate (0.100 g, 0.530 mmol, 0.8 equiv) in IPA (25 mL) were heated to 100° C. overnight. After cooling to ambient temperature, the crude mixture was quenched with 2M NH3/MeOH followed by concentrating to dryness and repeating once. The crude product was purified by flash chromatography and eluted with DCM:2M NH3/MeOH (100:0 to 95:5 using 2% 2M NH3/MeOH increments) to provide the desired product which was recrystallized with DCM/Hexanes to give the title compound (0.170 mg, 52%) as a solid.

1H NMR (DMSO d6, 300 MHz): δ 9.81 (s, 1H), 9.51 (br. s, 1H), 8.29 (s, 1H), 7.64 (d, J=6.6 Hz, 1H), 7.41 (d, J=7.7 Hz, 1H), 7.11 (d, J=11.6 Hz, 1H), 4.10-4.18 (m, 1H), 2.09 (s, 3H), 1.50-1.57 (m, 2H), 1.37-1.49 (m, 5H), 0.89-0.99 (m, 6H), 0.72-0.82 (m, 8H), 0.59-0.62 (m, 2H); m/z=491 (M+H)+.

Example 45

Synthesis of 2-isopropyl-5-nitroaniline

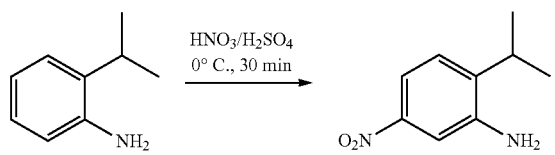

70% HNO3 (5.1 mL, 84.76 mmol, 1.2 equiv) was added dropwise to a mixture of 2-isopropylaniline (10 mL, 9.55 g, 70.63 mmol, 1 equiv) in 70 mL of conc. sulfuric acid at 0° C. The reaction mixture was stirred at this temperature for 30 minutes and then poured onto ice. The aqueous mixture was extracted with EtOAc (2×150 mL). The organic layers were combined and washed with sat'd NaHCO3. After evaporation, the residue was purified by column chromatography on silica gel using EtOAc/hexanes (3/7) to give 2 g of product (16%) as a dark red oil.

1H NMR (CDCl3, 300 MHz): δ 7.60 (dd, J=8.1, 2.7 Hz, 1H), 7.50 (d, J=2.7 Hz, 1H), 7.23 (d, J=8.7 Hz, 1H), 2.91 (sept, J=6.6 Hz, 1H), 1.28 (d, J=6.9 Hz, 6H); m/z=181 (M+H)+.

Example 46

Synthesis of 1-(2-isopropyl-5-nitrophenyl)-1H-tetrazole

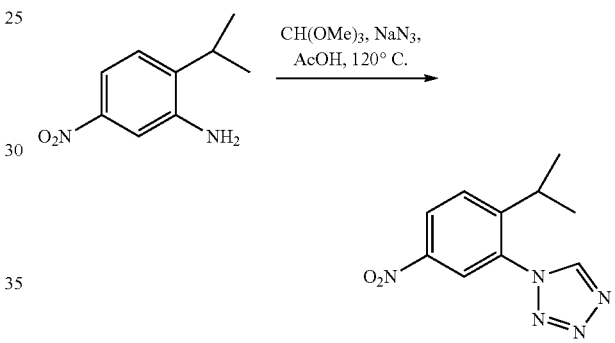

N.b.: TMS-N3 and tetrazole product are potentially explosive. Use a blast shield for this reaction and glassware with no scratches, cracks, etc. Avoid contact with metals, including metal spatulas. Keep the product slightly wet with residual solvent from the column.

To a solution of 2-isopropyl-5-nitroaniline (1.02 g, 5.67 mmol, 1 equiv) in 15 mL of acetic acid, trimethylorthoformate (3.1 mL, 28.35 mmol, 5 equiv) was added and the reaction mixture was stirred at room temperature for 10 minutes. The sodium azide (921 mg, 14.2 mmol, 2.5 equiv) was added and the reaction mixture was heated to 120° C. for 1 hour behind a blast shield. After allowing to cool to 0° C., 15 mL of 6N HCl was added. To the above solution sodium nitrite (587 mg, 8.51 mmol, 1.5 equiv) in 7.5 mL of water was added dropwise. The resulting solution was stirred at 0° C. for 15 minutes behind a blast shield. Around 60 mL of 2N NaOH was added to the above solution (ca. pH 4-5), the resulting precipitate was filtered and dried to give the desired product (780 mg) as a tan solid. The filtrate was extracted with EtOAc. The organic layer was separated and evaporated. The residue was purified by column chromatography on silica gel using EtOAc/hexanes (3/7) to give another 200 mg of product (total 76%).

1H NMR (CDCl3, 300 MHz): δ 8.85 (s, 1H), 8.45 (dd, J=8.7, 2.4 Hz, 1H), 8.18 (d, J=2.1 Hz, 1H), 7.76 (d, J=8.7 Hz, 1H), 2.72 (sept, J=6.9 Hz, 1H), 1.25 (d, J=6.9 Hz, 6H); m/z=234 (M+H)+

Example 47

Synthesis of 4-isopropyl-3-(1H-tetrazol-1-yl)benzenamine

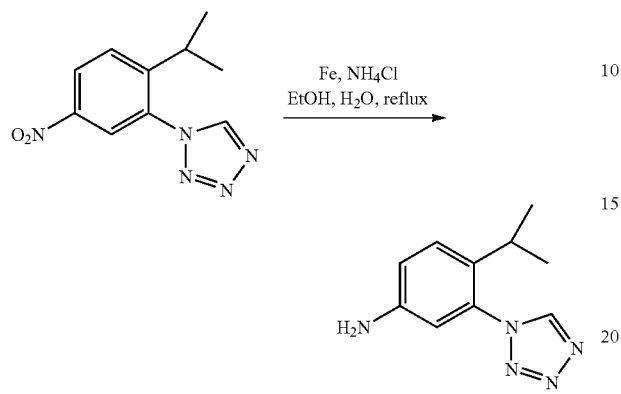

A mixture of 1-(2-isopropyl-4-5-nitrophenyl)-1H-tetrazole (780 mg, 3.35 mmol, 1 equiv), iron powder (564 mg, 10.03 mmol, 3 equiv) and ammonium chloride (541 mg, 10.10 mmol, 3 equiv) in EtOH (20 mL) and water (4 mL) was refluxed for 2 hours. After cooling to room temperature, the reaction mixture was filtered through a pad of Celite, and the pad of Celite was rinsed with EtOAc (50 mL). The filtrate was washed with water. The organic layer was separated and evaporated to dryness. The residue was purified by column chromatography on silica gel using EtOAc/hexanes (1/1) to give the product (500 mg, 74%) as a tan solid. m/z=204 (M+H)$^+$.

Example 48

Synthesis of N2-(4-isopropyl-3-(1H-tetrazol-1-yl)phenyl)-5-fluoro-N4-(2,2,6,6-tetramethylpiperidin-4-yl)pyrimidine-2,4-diamine

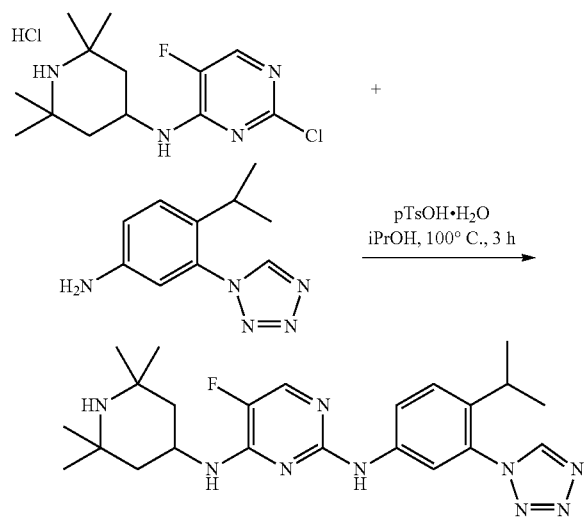

A mixture of 2-chloro-5-fluoro-N-(2,2,6,6-tetramethylpiperidin-4-yl)pyrimidin-4-amine hydrochloride (160 mg, 0.495 mmol, 1 equiv), 4-isopropyl-3-(1H-tetrazol-1-yl)benzenamine (121 mg, 0.594 mmol, 1.2 equiv), and para-toluenesulfonic acid monohydrate (75 mg, 0.396 mmol, 0.8 equiv) in IPA (3 mL) were heated to 100° C. for 3 hours. After cooling to ambient temperature, the crude mixture was quenched with 2M NH$_3$/MeOH followed by concentrating to dryness. The crude product was purified by flash chromatography and eluted with DCM:2M NH$_3$/MeOH (95:5) to provide the desired product (120 mg, 54%) as a white solid.

$^1$H NMR (DMSO-d$_6$, 300 MHz): δ 9.84 (s, 1H), 9.25 (br. s, 1H), 7.98-7.92 (m, 1H), 7.85 (d, J=2.1 Hz, 1H), 7.64 (br. s, 1H), 7.38 (d, J=8.7 Hz, 1H), 7.25-7.15 (m, 1H), 4.40-4.30 (m, 1H), 2.28-2.22 (m, 1H), 1.65-1.60 (m, 2H), 1.20-1.10 (m, 2H), 1.05 (d, J=6.6 Hz, 6H), 1.05-1.00 (m, 12H); m/z=454 (M+H)$^+$.

Example 49

Synthesis of 2-(4-isopropyl-3-(1H-tetrazol-1-yl)phenylamino)-4-(2,2,6,6-tetramethylpiperidin-4-ylamino)pyrimidino-5-carboxyamide

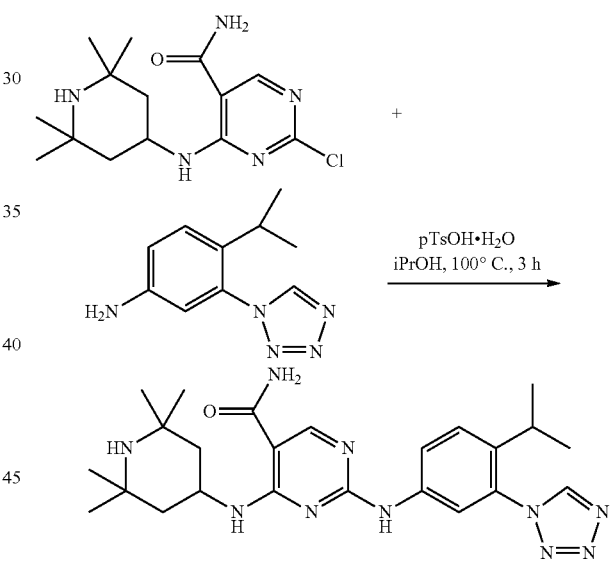

A mixture of 2-chloro-4-(2,2,6,6-tetramethylpiperidin-4-ylamino)pyrimidino-5-carboxyamide (160 mg, 0.513 mmol, 1 equiv), 4-isopropyl-3-(1H-tetrazol-1-yl)benzenamine (125 mg, 0.616 mmol, 1.2 equiv), and para-toluenesulfonic acid monohydrate (78 mg, 0.410 mmol, 0.8 equiv) in IPA (3 mL) were heated to 100° C. for 3 hours. The solid was filtered, washed with IPA and sonicated in 1N NaOH. The resulting solid was filtered, washed with water and dried to give the title compound (200 mg, 81%) as a pale white solid.

$^1$H NMR (DMSO-d$_6$, 300 MHz): δ 9.85 (s, 1H), 9.69 (br. s, 1H), 9.15 (br. s, 1H), 8.51 (s, 1H), 8.06 (br. s, 1H), 7.78 (br. s, 1H), 7.62 (br. s, 1H), 7.42 (d, J=9.0 Hz, 1H), 7.18 (br. s, 1H), 4.35-4.25 (m, 1H), 2.30-2.26 (m, 1H), 1.79-1.75 (m, 2H), 1.17-1.13 (m, 2H), 1.05 (d, J=6.9 Hz, 6H), 1.04 (s, 12H); m/z=479 (M+H)$^+$.

Example 50

Synthesis of 2-(4-isopropyl-3-(1H-tetrazol-1-yl)phenylamino)-4-(2,2,6,6-tetramethylpiperidin-4-ylamino)pyrimidino-5-carbonitrile

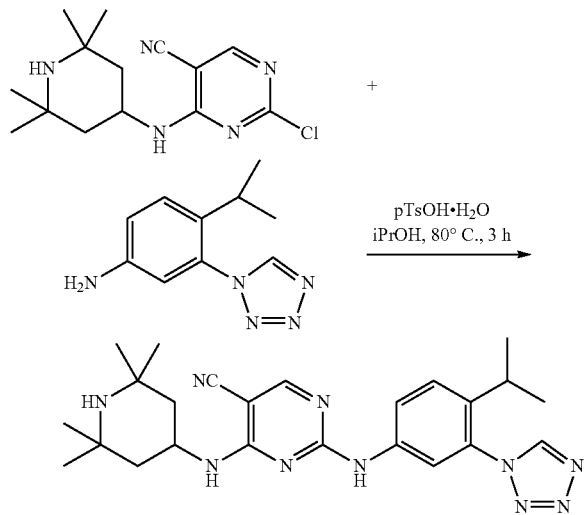

A mixture of 4-(2,2,6,6-tetramethylpiperidin-4-ylamino)-2-chloropyrimidine-5-carbonitrile (80 mg, 0.272 mmol, 1 equiv), 4-isopropyl-3-(1H-tetrazol-1-yl)benzenamine (66 mg, 0.326 mmol, 1.2 equiv), and para-toluenesulfonic acid monohydrate (41 mg, 0.218 mmol, 0.8 equiv) in IPA (2 mL) were heated to 80° C. for 3 hours. After cooling to ambient temperature, the crude mixture was quenched with 2M NH$_3$/MeOH followed by concentrating to dryness. The crude product was purified by flash chromatography and eluted with DCM:2M NH$_3$/MeOH (95:5) to provide the desired product (87 mg, 70%) as a white solid.

$^1$H NMR (DMSO-d$_6$, 300 MHz): δ 9.95 (br. s, 1H), 9.83 (s, 1H), 8.32 (s, 1H), 8.05 (br. s, 1H), 7.52 (br. s, 1H), 7.44 (d, J=8.1 Hz, 2H), 4.50-4.40 (m, 1H), 2.32-2.25 (m, 1H), 1.59-1.55 (m, 2H), 1.25-1.17 (m, 2H), 1.05 (d, J=6.6 Hz, 6H), 1.01 (s, 6H), 0.99 (s, 6H); m/z=461 (M+H)$^+$.

Synthesis of Compounds with Substituted Tetrazolyl Substituents

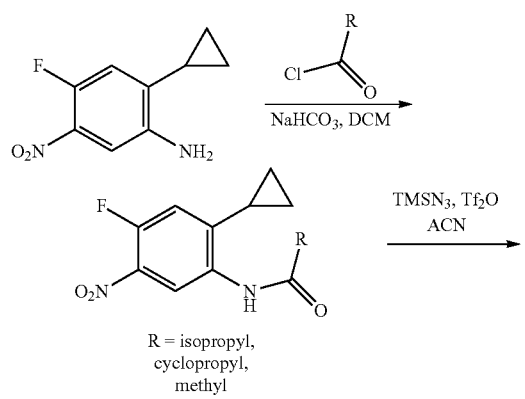

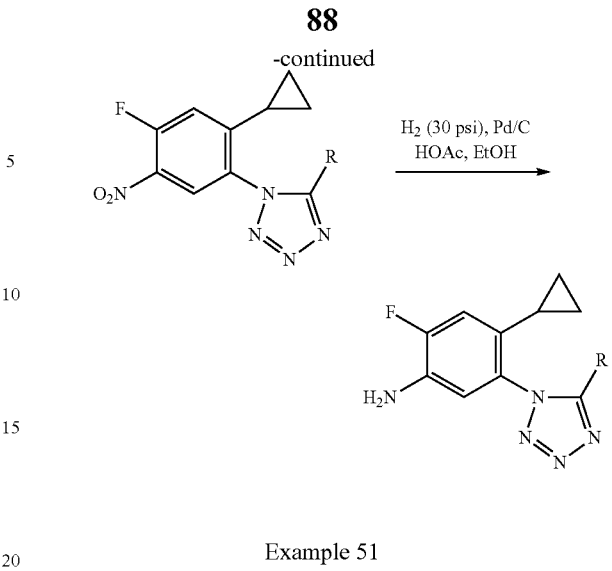

Example 51

Synthesis of N-(2-cyclopropyl-4-fluoro-5-nitrophenyl)isobutyramide

To a solution of 2-cyclopropyl-4-fluoro-5-nitrobenzenamine (as described in WO2011068898) (1.98 g, 10.09 mmol, 1 equiv) in dichloromethane (50 mL) at room temperature, was added NaHCO$_3$ (7.65 g, 90.84 mmol, 9 equiv), followed by 2-methylpropanoyl chloride (6.34 mL, 60.56 mmol, 6 equiv). The reaction mixture was stirred overnight. The reaction mixture was taken in water, and the layers were separated. The organic layer was washed with ice-cold 1N NaOH 2×, brine 1×, dried over Na$_2$SO$_4$, and concentrated to dryness. The crude product was absorbed onto silica gel and purified by flash chromatography and eluted with hex:EtOAc=100:0 to 50%-70% EtOAc using 10% EtOAc increments to afford N-(2-cyclopropyl-4-fluoro-5-nitrophenyl)isobutyramide (2.04 g, 84%) as a light-brown solid.

$^1$H NMR (DMSO d$_6$, 300 MHz): δ 9.63 (br. s, 1H), 8.17-8.19 (d, J=7.5 Hz, 1H), 7.05-7.10 (d, J=12.9 Hz, 1H), 2.66-2.75 (m, 1H), 2.02-2.11 (m, 1H), 1.04-1.12 (m, 8H), 0.78-0.83 (m, 2H); $^{19}$F NMR (282 MHz; d$_6$-DMSO) δ −122.0 (t); LCMS (m/z): 267 (MH$^+$).

Example 52

Synthesis of N-(2-cyclopropyl-4-fluoro-5-nitrophenyl)cyclopropane carboxamide

The general procedure described in Example 51 was followed. N-(2-cyclopropyl-4-fluoro-5-nitrophenyl)cyclopropane carboxamide (2.46 g, 92%) was obtained from 2-cyclopropyl-4-fluoro-5-nitrobenzenamine (described in WO2011068898) and cyclopropanecarboxyl chloride.

$^1$H NMR (DMSO d$_6$, 300 MHz): δ 9.94 (br. s, 1H), 8.27-8.30 (d, J=7.4 Hz, 1H), 7.04-7.09 (d, J=12.7 Hz, 1H), 2.11-2.20 (m, 1H), 1.90-1.98 (m, 1H), 1.07-1.14 (m, 2H), 0.81-0.86 (m, 6H); $^{19}$F NMR (282 MHz; d$_6$-DMSO) δ −123.0 (t); LCMS (m/z): 265 (MH$^+$).

Example 53

Synthesis of N-(2-cyclopropyl-4-fluoro-5-nitrophenyl)acetamide

The general procedure described in Example 51 was followed. N-(2-cyclopropyl-4-fluoro-5-nitrophenyl)acetamide (2.04 g, 84%) was obtained from 2-cyclopropyl-4-fluoro-5-nitrobenzenamine (described in WO2011068898) and acetyl chloride.

$^1$H NMR (DMSO d$_6$, 300 MHz): δ 9.71 (br. s, 1H), 8.23-8.26 (d, J=7.8 Hz, 1H), 7.03-7.07 (d, J=12.9 Hz, 1H), 2.08-2.16 (m, 4H), 1.05-1.12 (m, 2H), 0.80-0.85 (m, 2H); $^{19}$F NMR (282 MHz; d$_6$-DMSO) δ −123.0 (t); LCMS (m/z): 239 (MH$^+$).

Example 54

Synthesis of 1-(2-cyclopropyl-4-fluoro-5-nitrophenyl)-5-isopropyl-1H-tetrazole N-(2-cyclopropyl-4-fluoro-5-nitrophenyl)isobutyramide (1.90 g, 7.14 mmol, 1 equiv) was dissolved in acetonitrile (40 mL) under argon and cooled to −5° C. (external temperature). While maintaining the temperature at −5° C., trifluoromethanesulfonic anhydride (2.40 mL, 4.03 g, 14.27 mmol, 2 equiv) was added slowly dropwise and stirred for 1-2 minutes. Then trimethylsilyl azide (3.75 mL, 28.54 mmol, 4 equiv) was added slowly dropwise while maintaining the temperature at −5° C. TLC, LCMS indicated the reaction was complete in less than 1 minute. While maintaining the temperature at −5° C., the reaction was slowly quenched with ice-cold saturated NaHCO$_3$ and diluted with EtOAc. The layers were separated, and the organic layer was washed with brine 1×, dried over Na$_2$SO$_4$, and concentrated to dryness. The crude product was absorbed onto silica gel and purified by flash chromatography and eluted with hex:EtOAc=100:0 to 25%-30% EtOAc using 5% EtOAc increments to afford 1-(2-cyclopropyl-4-fluoro-5-nitrophenyl)-5-isopropyl-1H-tetrazole (1.69 g, 78%) as a yellow solid.

$^1$H NMR (DMSO d$_6$, 300 MHz): δ 8.59-8.63 (m, 1H), 7.35-7.40 (m, 1H), 2.96-3.08 (m, 1H), 0.96-1.24 (m, 11H); $^{19}$F NMR (282 MHz; d$_6$-DMSO) δ −114.0 (t); LCMS (m/z): 292 (MH$^+$).

Example 55

Synthesis of 5-cyclopropyl-1-(2-cyclopropyl-4-fluoro-5-nitrophenyl)-1H-tetrazole The general procedure described in Example 54 was followed. 5-cyclopropyl-1-(2-cyclopropyl-4-fluoro-5-nitrophenyl)-1H-tetrazole (2.14 g, 89%) was obtained from reaction of N-(2-cyclopropyl-4-fluoro-5-nitrophenyl)cyclopropanecarboxamide at −20° C. for 1 hour.

$^1$H NMR (DMSO d$_6$, 300 MHz): δ 8.56-8.59 (d, J=7.2 Hz, 1H), 7.41-7.45 (d, J=12.6 Hz, 1H), 1.81-1.90 (m, 1H), 1.23-1.32 (m, 1H), 0.93-1.15 (m, 8H); $^{19}$F NMR (282 MHz; d$_6$-DMSO) δ −114.0 (t); LCMS (m/z): 290 (MH$^+$).

Example 56

Synthesis of 1-(2-cyclopropyl-4-fluoro-5-nitrophenyl)-5-methyl-1H-tetrazole

The general procedure described in Example 54 was followed. 1-(2-cyclopropyl-4-fluoro-5-nitrophenyl)-5-methyl-1H-tetrazole (1.95 g, 92%) was obtained from reaction of N-(2-cyclopropyl-4-fluoro-5-nitrophenyl)acetamide at −78° C. to room temperature for overnight.

$^1$H NMR (DMSO d$_6$, 300 MHz): δ 8.52-8.54 (d, J=7.3 Hz, 1H), 7.39-7.44 (d, J=12.7 Hz, 1H), 2.43 (s, 3H), 1.21-1.30 (m, 1H), 0.92-1.04 (m, 4H); $^{19}$F NMR (282 MHz; d$_6$-DMSO) δ −114.0 (t); LCMS (m/z): 264 (MH$^+$).

Example 57

Synthesis of 4-cyclopropyl-2-fluoro-5-(5-isopropyl-1H-tetrazol-1-yl)benzenamine A Parr vessel was charged with 1-(2-cyclopropyl-4-fluoro-5-nitrophenyl)-5-isopropyl-1H-tetrazole (1.69 g, 5.80 mmol), EtOH (60 mL), AcOH (900 uL), and 10% Pd/C (50% in water, Degussa type E101; 340 mg, 20% by weight of the starting nitro compound) giving a suspension. The vessel was sealed, degassed, and back-filled with H$_2$ (×3). The vessel was then charged with 30 psi H$_2$ and allowed to shake until LCMS analysis indicated conversion. For this reaction, LCMS analysis indicated conversion at 2 days. The reaction mixture was filtered through a pad of Celite, and the pad of Celite was rinsed with MeOH. The filtrate was evaporated to dryness. The crude product was partitioned between EtOAc and H$_2$O which had been adjusted to ca. pH 12-14 with 3N NaOH. The aqueous and organic layers were partitioned, and the organic layer washed with 3N NaOH 1×. The aqueous layer was extracted with EtOAc 3×. The combined organic extracts were dried (Na$_2$SO$_4$), filtered, and the solvent removed in vacuo to give 4-cyclopropyl-2-fluoro-5-(5-isopropyl-1H-tetrazol-1-yl)benzenamine (1.08 g, 71%) off-white solid.

$^1$H NMR (DMSO d$_6$, 300 MHz): δ 6.74-6.77 (m, 1H), 6.81-6.86 (m, 1H), 5.42 (br. s, 2H), 2.92-3.01 (m, 1H), 1.21-1.24 (m, 6H), 0.94-1.04 (m, 1H), 0.63-0.67 (m, 2H), 0.44-0.57 (m, 2H); $^{19}$F NMR (282 MHz; d$_6$-DMSO) δ −130.0 (t); LCMS (m/z): 262 (MH$^+$).

Example 58

Synthesis of 4-cyclopropyl-5-(5-cyclopropyl-1H-tetrazol-1-yl)-2-fluorobenzenamine The general procedure described in Example 57 was followed. 4-cyclopropyl-5-(5-cyclopropyl-1H-tetrazol-1-yl)-2-fluorobenzenamine (205 mg, 97%) was obtained from reaction of 5-cyclopropyl-1-(2-cyclopropyl-4-fluoro-5-nitrophenyl)-1H-tetrazole for 2 hours.

$^1$H NMR (DMSO d$_6$, 300 MHz): δ 6.87-6.91 (d, J=12.6 Hz, 1H), 6.77-6.80 (d, J=8.70 Hz, 1H), 5.45 (br. s, 2H), 1.72-1.81 (m, 1H), 1.03-1.21 (m, 5H), 0.61-0.67 (m, 2H), 0.48-0.54 (m, 2H); $^{19}$F NMR (282 MHz; d$_6$-DMSO) δ −130.0 (t); LCMS (m/z): 260 (MH$^+$).

Example 59

Synthesis of 4-cyclopropyl-2-fluoro-5-(5-methyl-1H-tetrazol-1-yl)benzenamine The general procedure described in Example 57 was followed. 4-cyclopropyl-2-fluoro-5-(5-methyl-1H-tetrazol-1-yl)benzenamine (1.68 g, 97%) was obtained from reaction of 1-(2-cyclopropyl-4-fluoro-5-nitrophenyl)-5-methyl-H-tetrazole for 5 hours.

$^1$H NMR (DMSO d$_6$, 300 MHz): δ 6.84-6.89 (d, J=12.4 Hz, 1H), 6.73-6.76 (d, J=8.80 Hz, 1H), 5.42 (br. s, 2H), 2.38 (s,

3H), 1.05-1.14 (m, 1H), 0.60-0.66 (m, 2H), 0.47-0.52 (m, 2H); $^{19}$F NMR (282 MHz; d$_6$-DMSO) δ −130.0 (t); LCMS (m/z): 234 (MH$^+$).

Example 60

Synthesis of N2-(4-cyclopropyl-2-fluoro-5-(5-isopropyl-1H-tetrazol-1-yl)phenyl)-5-fluoro-N4-(2,2,6,6-tetramethylpiperidin-4-yl)pyrimidine-2,4-diamine

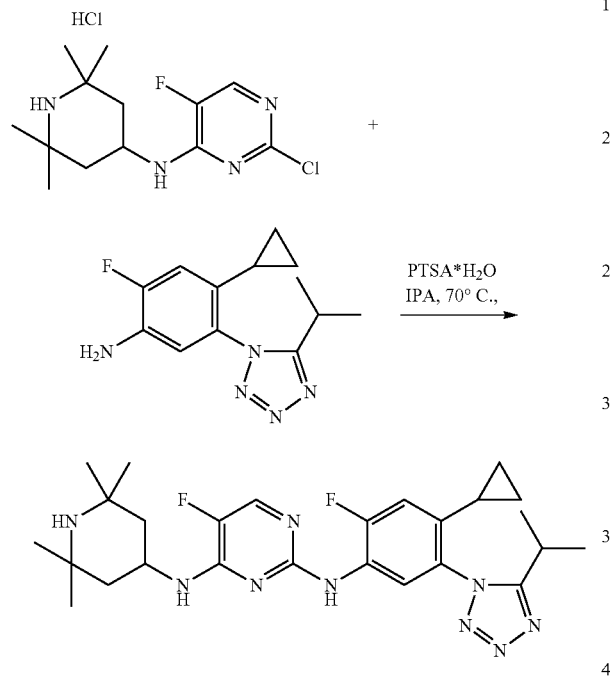

A mixture of 2-chloro-5-fluoro-N-(2,2,6,6-tetramethylpiperidin-4-yl)pyrimidin-4-amine hydrochloride (300 mg, 0.928 mmol, 1 equiv), 4-cyclopropyl-2-fluoro-5-(5-isopropyl-1H-tetrazol-1-yl)benzenamine (291 mg, 1.11 mmol, 1.2 equiv), and PTSA monohydrate (191 mg, 0.742 mmol, 0.8 equiv) in isopropyl alcohol (10 mL) were heated to 70° C. for 7 days. After cooling to ambient temperature, the crude reaction mixture was concentrated to dryness and taken in water, EtOAc, and 1N NaOH. The layers were separated. The organic layer was washed with 1N NaOH 2×, dried over Na$_2$SO$_4$, filtered, and concentrated to dryness. The crude product was purified by flash chromatography and eluted with DCM:2M NH$_3$/MeOH=100:0 to 96:4 using 1% 2M NH$_3$/MeOH increments to give compound N2-(4-cyclopropyl-2-fluoro-5-(5-isopropyl-1H-tetrazol-1-yl)phenyl)-5-fluoro-N4-(2,2,6,6-tetramethylpiperidin-4-yl)pyrimidine-2,4-diamine (245 mg, 52%) as a solid.

$^1$H NMR (DMSO d$_6$, 300 MHz): δ 8.55 (s, 1H), 7.71-7.82 (m, 2H), 7.12-7.19 (m, 1H), 6.96-7.00 (d, J=11.1 Hz, 1H), 4.01-4.39 (m, 1H), 2.91-2.99 (m, 1H), 1.52-1.59 (m, 2H), 0.98-1.24 (m, 22H), 0.78-0.81 (m, 2H), 0.60-0.69 (m, 2H); $^{19}$F NMR (282 MHz; d$_6$-DMSO) δ −117 (s), 167 (s); LCMS (m/z): 512 (MH$^+$).

Example 61

Synthesis of N2-(4-cyclopropyl-5-(5-cyclopropyl-1H-tetrazol-1-yl)-2-fluorophenyl)-5-fluoro-N4-(2,2,6,6-tetramethylpiperidin-4-yl)pyrimidine-2,4-diamine

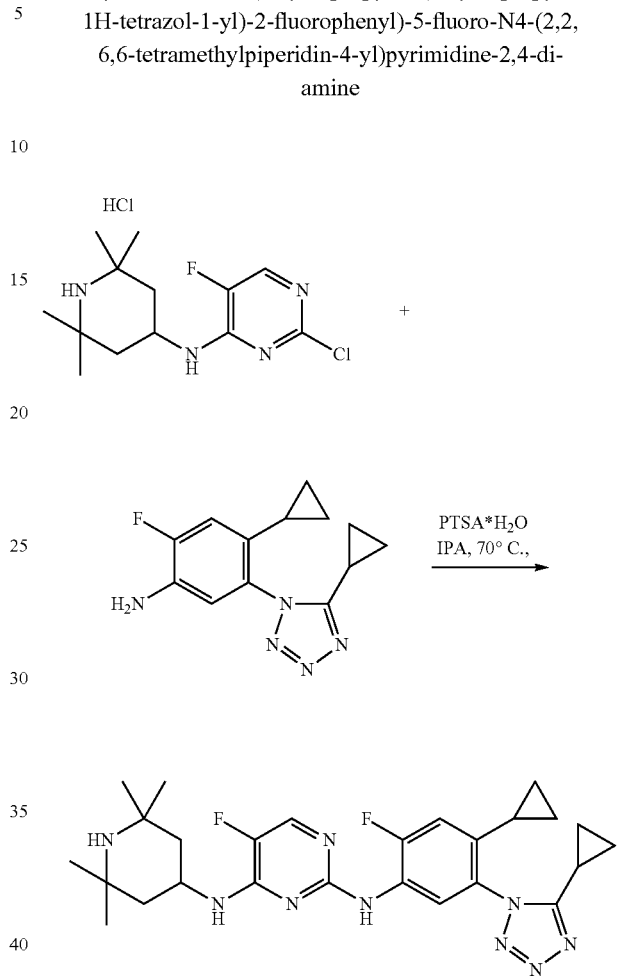

A mixture of 2-chloro-5-fluoro-N-(2,2,6,6-tetramethylpiperidin-4-yl)pyrimidin-4-amine hydrochloride (256 mg, 0.791 mmol, 1 equiv), 4-cyclopropyl-5-(5-cyclopropyl-1H-tetrazol-1-yl)-2-fluorobenzenamine (205 mg, 0.791 mmol, 1 equiv), and PTSA monohydrate (120 mg, 0.633 mmol, 0.8 equiv) in IPA (8 mL) were heated to 70° C. for 8 days. After cooling to ambient temperature, the crude mixture was concentrated to dryness and taken in water, EtOAc, and 1N NaOH. The layers were separated. The organic layer was washed with 1N NaOH 2×, dried over Na$_2$SO$_4$, filtered, and concentrated to dryness. The crude product was purified by trituration from EtOAc:hexane to give compound N2-(4-cyclopropyl-5-(5-cyclopropyl-1H-tetrazol-1-yl)-2-fluorophenyl)-5-fluoro-N4-(2,2,6,6-tetramethylpiperidin-4-yl)pyrimidine-2,4-diamine (276 mg, 68%) as a solid.

$^1$H NMR (DMSO d$_6$, 300 MHz): δ 8.52 (s, 1H), 7.81-7.88 (m, 2H), 7.16-7.20 (m, 1H), 7.02-7.06 (d, J=12.0 Hz, 1H), 4.01-4.39 (m, 1H), 1.69-1.81 (m, 1H), 1.52-1.59 (m, 2H), 0.94-1.24 (m, 20H), 0.75-0.79 (m, 2H), 0.60-0.68 (m, 2H); $^{19}$F NMR (282 MHz; d$_6$-DMSO) δ −118 (s), 166 (s); LCMS (m/z): 510 (MH$^+$).

Example 62

Synthesis of N2-(4-cyclopropyl-2-fluoro-5-(5-methyl-1H-tetrazol-1-yl)phenyl)-5-fluoro-N4-(2,2,6,6-tetramethylpiperidin-4-yl)pyrimidine-2,4-diamine

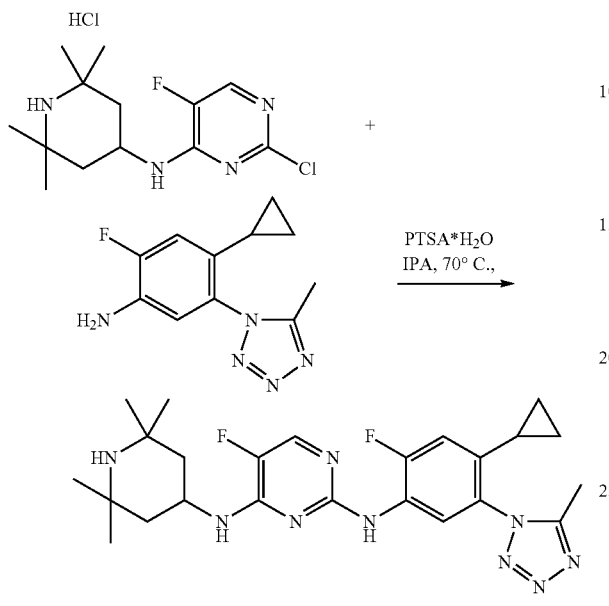

A mixture of 2-chloro-5-fluoro-N-(2,2,6,6-tetramethylpiperidin-4-yl)pyrimidin-4-amine hydrochloride (416 mg, 1.29 mmol, 1 equiv), 4-cyclopropyl-2-fluoro-5-(5-methyl-1H-tetrazol-1-yl)benzenamine (300 mg, 1.29 mmol, 1 equiv), and PTSA monohydrate (196 mg, 1.03 mmol, 0.8 equiv) in IPA (13 mL) were heated to 70° C. for 6 days. After cooling to ambient temperature, the crude mixture was concentrated to dryness and taken in water, EtOAc, and 1N NaOH. The layers were separated. The organic layer was washed with 1N NaOH 2×, dried over $Na_2SO_4$, filtered, and concentrated to dryness. The crude product was purified by trituration from EtOAc: hexane to give compound N2-(4-cyclopropyl-2-fluoro-5-(5-methyl-1H-tetrazol-1-yl)phenyl)-5-fluoro-N4-(2,2,6,6-tetramethylpiperidin-4-yl)pyrimidine-2,4-diamine (361 mg, 58%) as a solid.

$^1$H NMR (DMSO $d_6$, 300 MHz): δ 8.52 (s, 1H), 7.74-7.81 (m, 2H), 7.14-7.19 (m, 1H), 6.98-7.08 (d, J=12.0 Hz, 1H), 4.01-4.35 (m, 1H), 2.39 (s, 3H), 1.52-1.59 (m, 2H), 0.95-1.14 (m, 16H), 0.74-0.78 (m, 2H), 0.61-0.67 (m, 2H); $^{19}$F NMR (282 MHz; $d_6$-DMSO) δ −118 (s), 167 (s); LCMS (m/z): 484 (MH$^+$).

Example 63

Synthesis of N2-(4-cyclopropyl-2-fluoro-5-(5-(trifluoromethyl)-1H-tetrazol-1-yl)phenyl)-5-fluoro-N4-(2,2,6,6-tetramethylpiperidin-4-yl)pyrimidine-2,4-diamine

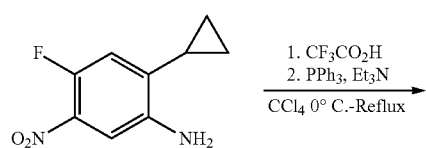

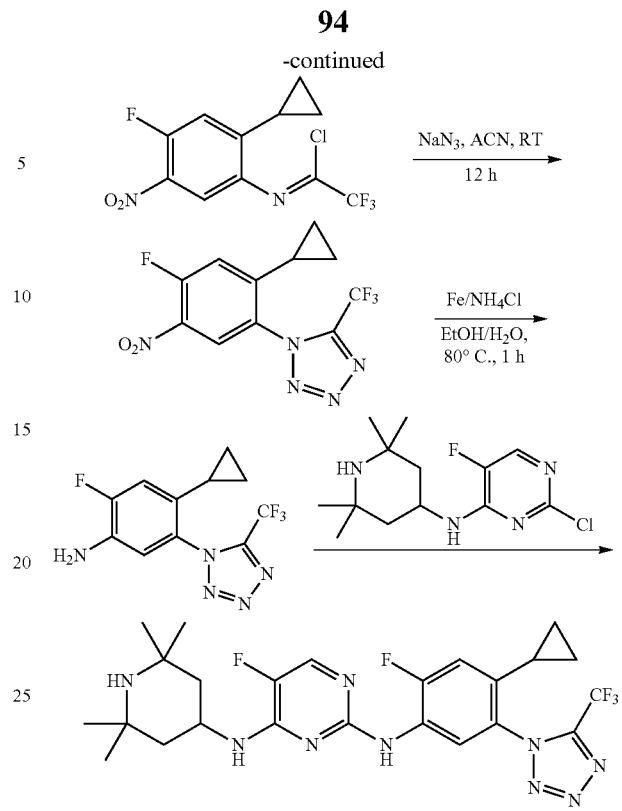

The general procedures described in Examples 40 and 41 were followed.

Characterization data of title compound: $^1$H NMR (DMSO) δ: 8.53 (s, 1H), 7.79-7.82 (m, 2H), 7.17 (d, 1H), 7.01 (d, 1H), 4.32 (br. m, 1H), 1.61 (d, 2H), 1.09-1.17 (m, 4H), 0.99 (s, 12H), 0.67 (d, 2H), 0.52 (m, 2H); $^{19}$F NMR (DMSO) δ: −165.9, −119.1, −60.7; LCMS (m/z): 538 (MH$^+$).

Example 64

Synthesis of $N^2$-(4-cyclopropyl-2-fluoro-5-(5-(fluoromethyl)-1H-tetrazol-1-yl)phenyl)-5-fluro-$N^4$-(2,2,6,6-tetramethylpiperidin-4-yl)pyrimidin-2,4-diamine

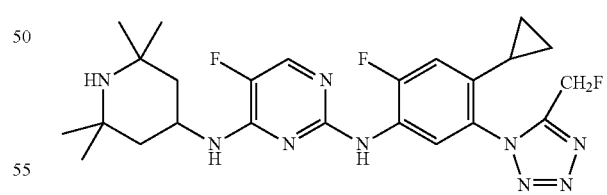

The general procedure described in Example 51 was followed where the last reduction step was performed with conditions from Example 41.

$^1$H NMR (300 MHz; $d_6$-DMSO) δ 8.62 (s, 1H), 8.26 (s, 1H), 7.84 (br. s, 1H), 7.26 (d, 1H), 7.06 (d, 1H), 5.67 (d, J=47.4 Hz, 2H), 4.30-4.20 (m, 1H), 2.31-2.25 (m, 1H), 1.68-1.64 (m, 2H), 1.24-1.20 (m, 2H), 1.11 (s, 6H), 1.05 (s, 6H), 0.74 (m, 2H), 0.62 (m, 2H); m/z=502.4 (M+H)$^+$; m/z=500.3 (M−H)$^+$.

Synthesis of trans-5-fluoro-$N^2$-(2-fluoro-4-(2-trifluoromethyl)cyclopropyl)-5-(1H-tetrazol-1-yl)phenyl)-$N^4$-(2,2,6,6-tetramethylpiperidin-4-yl)pyrimidine-2,4-diamine

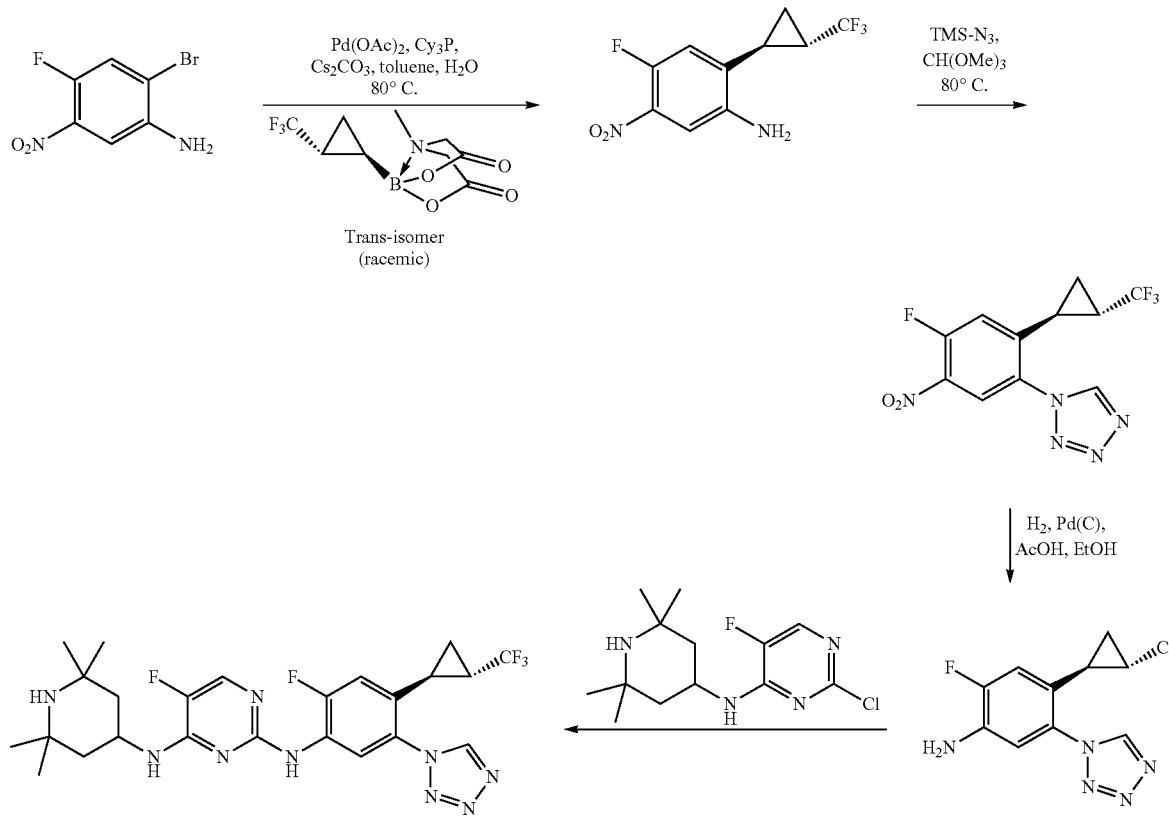

Example 65

Preparation of trans-2-(trifluoromethyl)cyclopropylboronic Acid MIDA Ester

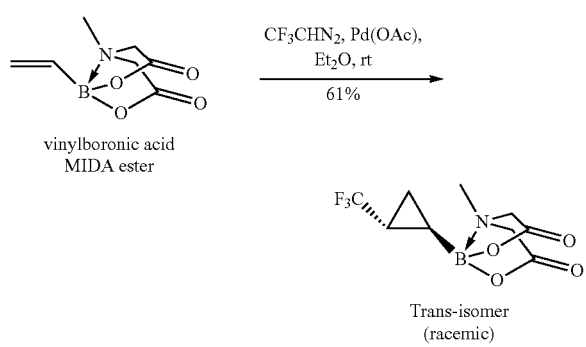

Step 1: Preparation of Trifluoromethyl Diazomethane

Sodium nitrite (4.6 g, 66 mmol) in water (10 mL) was added in one portion to a stirred solution of 2,2,2-trifluoroethylamine hydrochloride (8.1 g, 60 mmol) in water (25 mL) and ether (45 mL) at 0° C. The reaction vessel was sealed with a teflon stopper and the mixture stirred from 0° C. to room temperature and stirred at room temperature for approximately 3 hours. The mixture was then partitioned in a separating funnel and the ether layer containing the product was used directly in the next step without further purification. The yield of the trifluoromethyl diazomethane product was assumed to be approximately 50% based on literature citation herein (=3.32 g).

A safety notice for the procedure: Diazo compounds are potentially explosive. The reaction was performed behind a blast shield in glassware free from cracks or prominent scratches and glassware was inspected prior to use. Reference for the procedure is made to J. Am. Chem. Soc. 1943, 65, 1458, which is hereby incorporated by reference in its entirety.

Step 2: Preparation of trans-2-(trifluoromethyl)cyclopropylboronic Acid MIDA Ester A mixture of trifluoromethyl diazomethane (3.32 g, 30 mmol) in Et$_2$O (45 mL) was added dropwise to a stirred suspension of vinylboronic acid MIDA ester (Sigma-Aldrich, St. Louis, Mo.; 1.65 g, 9.0 mmol) and Pd(OAc)$_2$ (50 mg) in Et$_2$O at room temperature. After adding for minutes (about a quarter of the trifluoromethyl diazomethane had been added at this stage), more Pd(OAc)$_2$ (50 mg) and Et$_2$O (100 mL) was added, and trifluoromethyl diazomethane was added dropwise for another 20 minutes (approximately three quarters added after this time). EtOAc (50 mL) and Pd(OAc)$_2$ (50 mg) were added at this point and the remaining trifluoromethyl diazomethane was added dropwise over 10 minutes. After complete addition of the trifluoromethyl diazomethane the mixture was analysed by TLC which indicated complete reaction. The solvent was removed under vacuum and the residue was dry-loaded on to silica gel and purified by column chromatography on silica gel using EtOAc as eluent to give the product (1.45 g, 61%) as a solid. A sample was recrystallised from EtOAc, and then a small sample recrystallized again from 1,2-dichloroethane, to give crystals suitable for analysis by x-ray crystallography. X-ray studies indicated confirmed the material to be the trans-isomer. Note: product is trans-isomer but racemic.

Reference for the procedure is made to *Tetrahedron Letters* 2010, 51, 1009-1011, which is hereby incorporated by reference in its entirety. Reference for the procedure and procedures below is made to U.S. Provisional Patent Application Ser. No. 61/418,654, entitled 'cyclopropyl MIDA Boronate', filed Dec. 1, 2010, which is hereby incorporated in its entirety.

$^1$H NMR (DMSO-d$_6$, 300 MHz): δ 3.99-3.72 (m, 4H), 2.70 (s, 3H), 1.28 (m, 1H), 0.53 (m, 1H), 0.31 (m, 1H), 0.00 (m, 1H); $^{19}$F NMR (DMSO-d$_6$, 282 MHz): −65.4.

Example 66

Preparation of trans-4-fluoro-2-(2-trifluoromethyl) cyclopropyl)-5-nitrobenzeneamine

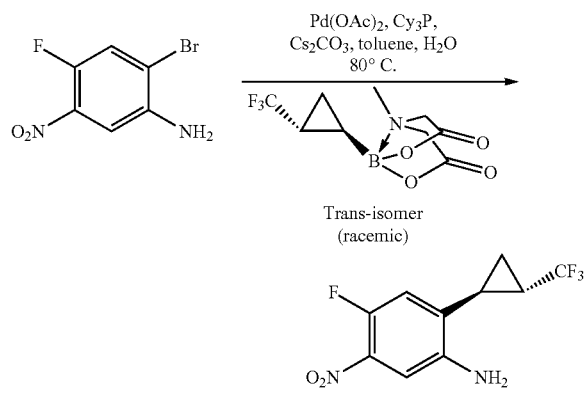

A mixture of 2-bromo-4-fluoro-5-nitroaniline (353 mg, 1.5 mmol), trans-2-(trifluoromethyl)cyclopropylboronic acid MIDA ester (477 mg, 1.8 mmol), Pd(OAc)$_2$ (51 mg, 0.23 mmol), Cy$_3$P (126 mg, 0.45 mmol) and Cs$_2$CO$_3$ (2.93 g, 9.0 mmol) in toluene (5 mL) and H$_2$O (1.5 mL) was de-gassed with N$_2$ for 15 minutes, then placed under a nitrogen atmosphere and heated to reflux for 3 hours. The temperature of the mixture was reduced to 100° C. (block temperature) and the mixture stirred overnight. After completion of the reaction, the mixture was cooled and EtOAc (100 mL) and H$_2$O (100 mL) were added. The mixture was filtered through Celite and the filter cake washed with H$_2$O (50 mL) and EtOAc (50 mL). The aqueous and organic layers of the filtrate were partitioned, and the aqueous layer was extracted with EtOAc (1×50 mL). The combined organic layers were washed with brine (1×50 mL), dried (MgSO$_4$), filtered and the solvent removed under vacuum to leave a crude residue. The residue was dry-loaded on to silica gel and purified by column chromatography on silica gel using EtOAc/hexane (2:8 to 3:7) as eluent to give the product (214 mg, 54%). Note: product is trans-isomer but racemic.

$^1$H NMR (300 MHz, d$_6$-DMSO): δ 7.32 (dd, J=6.8, 2.3 Hz, 1H), 7.03 (dd, J=12.6, 2.0 Hz, 1H), 5.60 (br. s, 2H), 2.49-2.41 (m, 1H), 2.36-2.29 (m, 1H), 1.42-1.35 (m, 1H), 1.16-1.11 (m, 1H); $^{19}$F NMR (282 MHz, d$_6$-DMSO): δ −135.7 (dd), −64.8 (d); m/z=265.87 (M+H); m/z=263.00 (M−H)$^+$.

Example 67

Preparation of trans-(4-fluoro-2-(2-trifluoromethyl) cyclopropyl)-5-nitrophenyl-1H-tetrazole

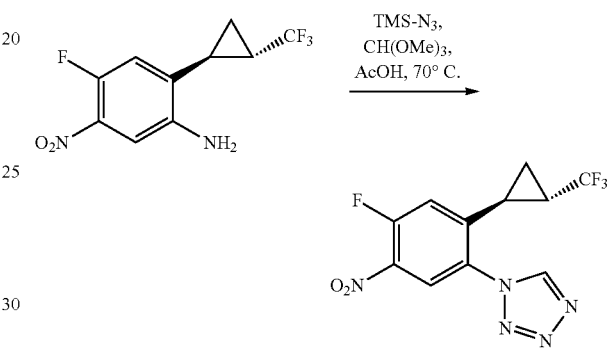

A mixture of trans-4-fluoro-2-(2-trifluoromethyl)cyclopropyl)-5-nitrobenzeneamine (200 mg, 0.76 mmol), trimethylorthoformate (0.83 mL, 7.6 mmol), trimethylsilyl azide (200 µL, 1.52 mmol) and AcOH (3 mL) were heated to 70° C. and stirred overnight. After cooling, the mixture was concentrated under vacuum. The residue was partitioned between EtOAc (75 mL0 and 1N NaOH (30 mL). The organic layer was dried (MgSO$_4$), filtered and the solvent removed under vacuum to leave a crude residue. The residue was purified by column chromatography on silica gel (residue dry-loaded on to silica gel) using EtOAc/hexane (3:7 to 4:6) as eluent to give the product (154 mg, 64%). Note: product is trans-isomer but racemic.

$^1$H NMR (300 MHz, d$_6$-DMSO): δ 9.85 (s, 1H), 8.57 (d, J=7.0 Hz, 1H), 7.69 (d, J=12.1 Hz, 1H), 2.52 (m, 1H), 2.19-2.20 (m, 1H), 1.55-1.49 (m, 1H), 1.38-1.30 (m, 1H); $^{19}$F NMR (282 MHz, d$_6$-DMSO): 6-114.6, −65.8 (d); m/z=359.10 (M+MeCN+H)$^+$; m/z=316.04 (M−H)$^+$.

Example 68

Preparation of trans-(2-fluoro-4-(2-trifluoromethyl) cyclopropyl)-5-(1H-tetrazol-1-yl)benzeneamine

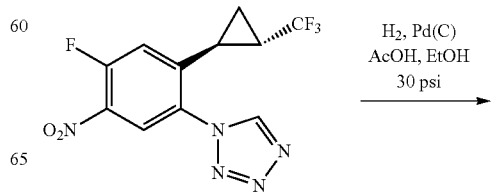

-continued

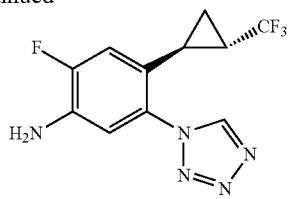

A mixture of trans-(4-fluoro-2-(2-trifluoromethyl)cyclopropyl)-5-nitrophenyl-1H-tetrazole (150 mg, 0.47 mmol) and palladium, 10% by weight on charcoal, Degussa grade E101 (30 mg), AcOH (75 μL) and EtOH (20 mL) were hydrogenated at 25-30 psi for 1 week (until LC/MS showed >95% conversion to product. Note: the reduction of a hydroxylamine intermediate to the aniline product is the slow step). The mixture was then filtered through Celite and the filter cake washed with EtOH (3×20 mL). The filtrate was concentrated under vacuum to leave a crude residue that was purified by column chromatography on silica gel (residue dry-loaded on to silica gel) using EtOAc/hexane (4:6) as eluent to give the product (94 mg, 69%) as a solid. Note: product is trans-isomer but racemic.

$^1$H NMR (300 MHz, d$_6$-DMSO): δ 9.79 (m, 1H), 7.07 (d, J=12.2 Hz, 1H), 6.81 (d, J=8.3 Hz, 1H), 5.65 (br. s, 2H), 2.07-1.95 (m, 2H), 1.17-1.11 (m, 1H), 1.08-1.01 (m, 1H); $^{19}$F NMR (282 MHz, d$_6$-DMSO): δ −131.5 (dd), 65.5 (d); m/z=329.15 (M+MeCN+H)$^+$; m/z=286.08 (M−H)$^+$.

Example 69

Preparation of trans-5-fluoro-N2-(2-fluoro-4-(2-trifluoromethyl)cyclopropyl)-5-(1H-tetrazol-1-yl)phenyl)-N-(2,2,6,6-tetramethylpiperidin-4-yl)pyrimidine-2,4-diamine

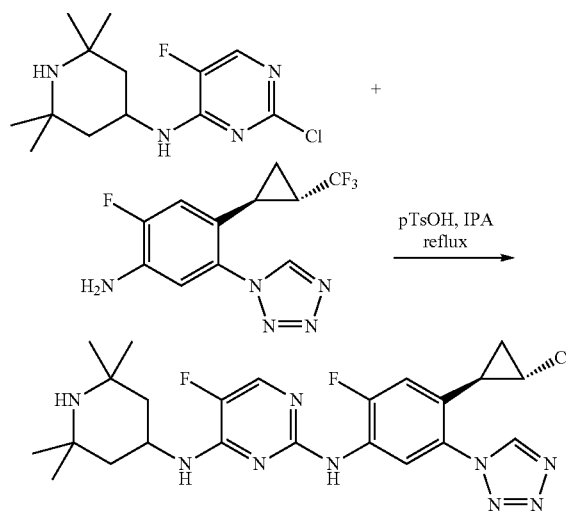

A mixture of trans-(2-fluoro-4-(2-trifluoromethyl)cyclopropyl)-5-(1H-tetrazol-1-yl)benzeneamine (90 mg, 0.31 mmol), 2-chloro-5-fluoro-N4-(2,2,6,6-tetramethylpiperidin-4-yl)-4-pyrimidineamine hydrochloride (85 mg, 0.26 mmol) and para-toluenesulfonic acid monohydrate (40 mg, 0.21 mmol) in isopropyl alcohol (2 mL) was heated to 70° C. and stirred over a weekend. More isopropyl alcohol (10 mL) was added and the mixture became homogenous after this reached 70° C. The mixture was allowed to cool to room temperature whereupon a precipitate emerged. The mixture was filtered and the filter cake was washed with isopropyl alcohol (2 mL) [Note: there is still a lot of product in the filtrate]. The filter cake was then suspended in EtOAc (50 mL) and 0.5 N NaOH (30 mL) was added. The aqueous and organic layers were partitioned and the organic layer was washed with brine (1×20 mL), dried (MgSO$_4$), filtered and the solvent removed under vacuum to leave the product (49 mg, 35%) as a solid. Note: product is trans-isomer but racemic.

$^1$H NMR (300 MHz, d$_6$-DMSO): δ 9.83 (d, J=1.5 Hz, 1H), 8.65 (br. s, 1H), 8.00 (d, J=7.3 Hz, 1H), 7.83 (d, J=3.8 Hz, 1H), 7.28 (d, J=11.7 Hz, 1H), 7.20 (br. d, J=7.7 Hz, 1H), 4.29-4.15 (m, 1H), 2.19-2.10 (m, 1H), 2.09-2.01 (m, 1H), 1.61-1.52 (m, 2H), 1.25-1.02 (m, 4H), 0.97 (s, 6H), 0.92 (s, 6H); $^{19}$F NMR (282 MHz, d$_6$-DMSO): δ −165.7, −119.6, −65.6; m/z=538.48 (M+H)$^+$; m/z=536.38 (M−H)$^+$.

Example 70

PKC Assay

The inhibition of PKC-alpha, PKC-beta, PKC-delta, PKC epsilon and PKC-theta activity was determined via ELISA as follows: NUNC MAXISORP (#436110) or Costar High Binding (#3922) plates were coated with 0.01 mg/mL Neutravidin (Pierce #PI-31000) in 1×PBS (100 μL/well) for 18-24 hours at 4° C. When ready to be used, plates were washed with 1×PBST and then blocked with 2% BSA in 1×PBST (100 μL/well) for a minimum of 1 hour at room temperature. The reactions were conducted in a volume of 60 μL/well. When ready to begin, the plates were washed with 1×PBST to remove the 2% BSA blocking solution. Reaction solution containing the necessary buffer components as well as the appropriate concentrations of ATP and peptide substrate was then added to each well (see Table 3). Appropriate concentrations of test compound was then added—with the volume added should taking into consideration the DMSO tolerance of the kinases being about 0.2%. The reaction was then initiated by the addition of kinase—the approximate final concentration of which is listed in Table 3 (note that this will vary depending on the batch to batch variability in the activity of enzymes). After allowing the reaction to stand at room temperature for 20 minutes, the plates were then washed with 1×PBST.

TABLE 3

| Kinase | Buffer components | [ATP] (uM) | [peptide] (uM) | Time (min) | 1° and 2° antibodies | Notes |
|---|---|---|---|---|---|---|
| PKCs α: ~8 ng/mL | 20 mM Hepes pH 7.4 | 1 μM | 1 (μM PKC peptide (biotin-RFARKGSLRQKNV) | 20 min | Rabbit pSer PKC substrate Ab (Cell Signaling #2261); | 0.15 mg/mL DAG (Sigma #00138) |

TABLE 3-continued

| Kinase | Buffer components | [ATP] (uM) | [peptide] (uM) | Time (min) | 1° and 2° antibodies | Notes |
|---|---|---|---|---|---|---|
| β: ~16 ng/mL<br>δ: ~13 ng/mL<br>ε: ~13 ng/mL<br>θ: ~8 ng/mL | 5 mM MgCl$_2$<br>0.2 mM CaCl$_2$<br>1 mM DTT<br>0.05% Chaps | | (Invitrogen #P2760) | | HRP-goat a-rabbit (Jackson Immunoresearch #111-035-003) | 0.75 mg/mL Phosphoserine (Sigma #P6641) DMSO tolerance ~0.2% |

After removal of the reaction mixture from the plate and washing with 1×PBST, an antibody developing solution containing a 1:10,000 dilution of the appropriate primary and secondary antibodies (Table 3) in a 0.1% BSA solution in 1×PBST was then added to each well (100 µL/well). This was then allowed to stand at room temperature for a minimum of 1 hour. After this time, the plates were once again washed with 1×PBST. The SuperSignal ELISA Pico Chemiluminescent substrate (Pierce #PI-37069) was then added (100 µL/well) and the plate was read on a luminescence plate reader Example 71

PKC Assay

Alternatively, the inhibition of PKC activity is measured by monitoring the production of phosphorylated peptide by fluorescence polarization at different concentrations of the inhibitor. Reactions are carried out in 96-well plate format with a total volume of 20 µL containing 20 mM HEPES, pH 7.4, 5 mM MgCl$_2$, 0.2 mM CaCl$_2$, 1 mM DTT, 0.02% Brij-35, 0.1 mg/mL phosphatidylserine, 0.02 mg/mL dioleoyl-sn-glycerol and 5 µM each of ATP and the peptide substrate. Compounds are first diluted serially in DMSO and then transferred to a solution containing the above concentrations of HEPES, MgCl$_2$, CaCl$_2$, DTT, and Brij-35 to yield 5× compound solutions in 2% DMSO, which is then added to the reaction solution. Reactions are initiated by the addition of PKC at a typical concentration as described in Table 4, and then allowed to incubate at room temperature for 20 min. At the end of this time, a combination of quench (EDTA) and detection (peptide tracer and antibody) reagents is added using the protocol of Invitrogen P2748. After a 30 min. period of incubation, the amount of phosphorylated peptide generated is measured by fluorescence polarization (Ex=485 nm, Em=535 nm) using a Tecan Polarian instrument.

Example 72

IL-2 ELISA, Human Primary T Cell, anti-CD3+ CD28+(Whole Cell Assay)

Human primary T cell isolation and culture: Human primary T cells were prepared as follows. Whole blood was obtained from a healthy volunteer, mixed 1:1 with PBS, layered on to Ficoll Hypaque (Amersham Pharmacia Biotech, Piscataway, N.J., Catalog #17-1440-03) in 2:1 blood/PBS: ficoll ratio and centrifuged for 30 min at 4° C. at 1750 rpm. The cells at the serum: ficoll interface were recovered and washed twice with 5 volumes of PBS. These freshly isolated human peripheral blood mononuclear cells were cultured in Yssel's medium containing U/mL IL2 in a flask pre-coated with 1 µg/mL αCD3 and 5 µg/mL αCD28 (Anti-Human CD3, BD Pharmingen Catalog #555336, Anti-Human CD28, Beckman Coulter Catalog #IM1376). The cells were stimulated for 3-4 days, then transferred to a fresh flask and maintained in RPMI (RPMI-1640 with L-Glutamine; Mediatech, Inc., Herndon Va., cat. #10-040-CM) with 10% FBS and 40 U/mL IL-2. The primary T-cells were then washed twice with PBS to remove the IL-2.

Primary T cell stimulation and IL2 ELISA: Human primary T cells (100,000 cells per well) were pre-incubated with or without test compound in Yssel's medium for 1 hr at 37° C. Cells were then stimulated by transferring them to round-bottom 96-well plates pre-coated with 1 µg/ml αCD3 and 5 µg/ml αCD28. For counter assay, cells were instead stimulated by adding 8× stock solutions of PMA and ionomycin in Yssels (for final concentrations of 0.5 ng/ml PMA and 0.1 µM ionomycin, both from Calbiochem). Cells were incubated at 37° C. for 24 hours before 100 µL supernatants were harvested for quantification of IL-2 by ELISA using Human IL-2 Duoset ELISA Kit from R and D Systems, Cat. #DY202E.

Table 5 shows the IC$_{50}$ values for compounds tested in the whole cell assay, in which "A" indicates an IC$_{50}$ in the indi-

TABLE 4

| | Peptide substrate | SEQ ID | Enzyme source | Typical enzyme concentration |
|---|---|---|---|---|
| PKC theta | RFARKGSLRQKNV | Seq ID No. 1 | Upstate Biotechnologies, Temecula, CA, cat. #14-444 | 40 ng/mL |
| PKC epsilon | RFARKGSLRQKNV | Seq ID No. 1 | Upstate Biotechnologies, Temecula, CA, cat. #14-518 | 50 ng/mL | cated assay of less than 0.25 µM; "B" is 0.25 to 0.5 µM; "C" is 0.5 to 1 µM; and "D" indicates that the $IC_{50}$ is greater than 1 µM.

TABLE 5

| Compound | Whole Cell assay |
|---|---|
| I-1 | A |
| I-2 | A |
| I-3 | C |
| I-4 | A |
| I-5 | A |
| I-6 | A |
| I-7 | A |
| I-8 | A |
| I-9 | A |
| I-10 | B |
| I-11 | A |
| I-12 | A |
| I-13 | A |
| I-14 | A |
| I-15 | A |
| I-16 | A |
| I-17 | A |
| I-18 | A |
| I-19 | A |
| I-20 | A |

Example 73

Calcium Influx

HEK-FLPTREX cells are stably transfected with pcDNA5/FRT/TO+hTRPV4a, rat TRPV1-HA or rTRPA1-HA are grown in Dulbecco's Modified Eagle's Medium (DMEM) containing 10% tetracycline-free fetal bovine serum, hygromycin (50 µg/ml) and blasticidin (10 µg/ml). Cells are treated with tetracycline (0.1 µg/ml, 20 h) to induce TRP expression. DRG from thoracic and lumbar spinal cord of rats or mice are minced in cold Hank's Balanced Salt Solution (HBSS) and incubated for 60 at 37° C. in DMEM containing 1 mg/ml of collagenase type IA and 0.1 mg/ml of DNAse type IV, pelleted and incubated with 0.25% trypsin for 30 min. Neurons are pelleted, suspended in DMEM containing 10% fetal bovine serum, 10% horse serum, 100 U/ml penicillin, 0.1 mg/ml streptomycin, 2 mM glutamine, dissociated by gentle trituration until the solution appears cloudy and homogeneous and plated on glass coverslips coated with PolyOnitine/laminin. Neurons are cultured for 3-4 days before the experiment.

Cells grown on coverslips or on a 96 multiwell plate are incubated in HBSS (pH 7.4) containing $Ca^{2+}$ and Mg2+, 20 mM HEPES buffer, 0.1% BSA, 100 U/ml penicillin, 100 µg/ml streptomycin, with 2.5-5 µM Fura-2AM (Invitrogen) for 20-45 min at 37° C. Cells are washed and fluorescence is measured at 340 nm and 380 nm excitation and 510 nm emission in a F-2500 spectrophotometer, or in a Flexstation 3 Microplate Reader III (for the measurement of the calcium in the cell population) or using a Zeiss Axiovert microscope, an ICCD video camera and a video microscopy acquisition program (for the measurement of the calcium influx in the single neurons). Substances are injected directly into the chamber (20 ml into 2 ml, for the spectrophotometer; 20 ml in 200 ml for the Flexstation, 50 ml in 350 ml in the chamber for the single cells).

Example 74

In Vivo Hyperplasia

Mechanical pain is quantified as the number of times the hind paw is withdrawn in response to 5 applications of a 0.173 mN von Frey hair. Responses are expressed as a percentage (e.g. 3 withdrawals out of 5 are recorded as 60%) and mechanical hyperalgesia defined as increase in the percentage of withdrawal compared to basal measurement. 2) Mechanical pain is quantified using the 'up-down paradigm', determining the 50% response threshold to the von Frey filaments applied to the mid-plantar surface for 5 s or until a withdrawal response occurred. Von Frey filaments are in this range of intensities: 1.65, 2.44, 2.83, 3.22, 3.61, 3.84, 4.08.

Thermal hyperalgesia is assessed in mice using a plantar test apparatus and quantified as the latency of paw withdrawal to a radiant heat. Thermal hyperalgesia is defined as a decrease in the withdrawal latency compared to the basal measurement. After measuring basal level mice, under light halothane anesthesia (5%), are injected with testing compound into the left or right paws (5-10 µl intraplantar injection) and paw withdrawal measurements repeated at different time point. To assess PAR2 TRPV1, TRPV4 and TRPA1 mediated hyperalgesia and potentiation of TRPV-mediated responses, mice are treated with PAR2-AP for 15 min followed by capsaicin, 4αPDD or HNE. To assess the role of protein kinases, the antagonists or the corresponding vehicles are injected 20-30 minutes before the challenge with agonists. The effects induced by the different treatments are evaluated within the same rat comparing the responses recorded in the right paw (receiving for example saline, or vehicle) with the responses obtained in the left paw (receiving for example PAR2-AP or 4αPDD).

Formalin induced hyperalgesia is assessed using 5% solution of formalin administered by intradermal injection into the dorsal surface of the mouse or rat forepaw to induce a painful behavior. Pain is accessed on a four-level scale related to posture: 0, normal posture; 1, with the injected paw remaining on the ground but not supporting the animal; 2, with the injected paw clearly raised; and 3, with the injected paw being licked, nibbled, or shaken. Animals are observed and scored for behavior at 3 minutes after the injection (defined as initial phase that results from the direct stimulation of nociceptors), and then at 30-60 minutes after the injection (defined as second phase that involves a period of sensitization during which inflammatory phenomena occur). The nociceptive behavioral score for each 3-min interval is calculated as the weighted average of the number of seconds spent in each behavior. 2.5% solution of formalin is administered by intraplantar injection and thermal and mechanical pain measured as described above after 30-60 min. To assess the role of protein kinases, antagonists or their vehicles (control) are injected into the right paws 20-30 minutes before formalin. Nociceptive behavior will be scored for each rats and compared to control.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of the formula:

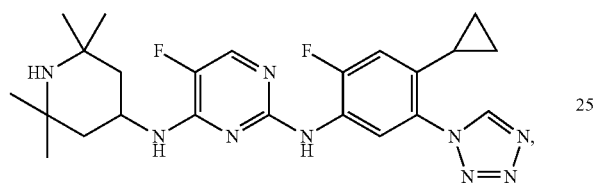

N2-(4-Cyclopropyl-2-fluoro-5-tetrazol-1-yl-phenyl)-5-fluoro-N4-(2,2,6,6-tetramethyl-piperidin-4-yl)-pyrimidine-2,4-diamine (I-12), or a pharmaceutically acceptable salt or stereoisomer thereof.

2. The compound of claim 1, wherein the pharmaceutically acceptable salt is a formate salt.

* * * * *